(12) United States Patent
Suominen et al.

(10) Patent No.: US 8,097,448 B2
(45) Date of Patent: Jan. 17, 2012

(54) **GENETICALLY MODIFIED YEAST OF THE SPECIES *ISSATCHENKIA ORIENTALIS* AND CLOSELY RELATES SPECIES, AND FERMENTATION PROCESSES USING SAME**

(75) Inventors: Pirkko Suominen, Maple Grove, MN (US); Aristos Aristidou, Highland Ranch, CO (US); Merja Pentilla, Helsinki (FI); Marja Ilmen, Helsinki (FI); Laura Ruohonen, Helsinki (FI); Kari Koivuranta, Vantaa (FI); Kevin Roberg-Perez, Minneapolis, MN (US)

(73) Assignee: Cargill Inc., Wayzata, MN (US)

( * ) Notice: Subject to any disclaimer, the term of this patent is extended or adjusted under 35 U.S.C. 154(b) by 193 days.

(21) Appl. No.: 11/921,161

(22) PCT Filed: May 30, 2006

(86) PCT No.: PCT/US2006/020782
§ 371 (c)(1),
(2), (4) Date: Nov. 27, 2007

(87) PCT Pub. No.: WO2007/032792
PCT Pub. Date: Mar. 22, 2007

(65) Prior Publication Data
US 2009/0226989 A1    Sep. 10, 2009

(51) Int. Cl.
*C12N 1/00* (2006.01)
*C12N 15/00* (2006.01)
*C12N 15/09* (2006.01)

(52) U.S. Cl. .............. 435/254.11; 435/137; 435/255.5; 435/255.4; 435/69.1

(58) Field of Classification Search .................... None
See application file for complete search history.

(56) References Cited

U.S. PATENT DOCUMENTS

| 2003/0190630 A1 | 10/2003 | Rajgarhia et al. |
| 2005/0080277 A1 | 4/2005 | Nishiyama et al. |
| 2006/0110810 A1* | 5/2006 | Rajgarhia et al. ............. 435/139 |
| 2006/0234364 A1 | 10/2006 | Rajgarhia |
| 2007/0092956 A1 | 4/2007 | Rajgarhia |

FOREIGN PATENT DOCUMENTS

| WO | 9914335 A | 3/1995 |
| WO | 9513362 A | 5/1995 |
| WO | 9954477 A | 10/1999 |
| WO | 0071738 A | 11/2000 |
| WO | 02/42471 A | 5/2002 |
| WO | 03049525 A | 6/2003 |
| WO | WO 03/049525 | 6/2003 |
| WO | 03062430 A | 7/2003 |
| WO | 03102152 A | 12/2003 |
| WO | 03102201 A | 12/2003 |
| WO | 2004099381 A | 4/2004 |

OTHER PUBLICATIONS

Kurtzman et al., 'Identification and Phylogony of Ascomycetous Yeasts . . . , Antonie van Leeuwenhoek 73:331-371 (1998).
Traff et al, "Deletion of the GRE3 Aldose Reductase Gene . . . ", Environmental Microbiology vol. 67, pp. 5668-5674 (Dec. 2001).

* cited by examiner

*Primary Examiner* — Maria Marvich
(74) *Attorney, Agent, or Firm* — Gary C Cohn PLLC

(57) ABSTRACT

Cells of the species *Issatchenkia orientalis* and closely related yeast species are transformed with a vector to introduce an exogenous lactate dehydrogenase gene. The cells produce lactic acid efficiently and are resistant at low pH, high lactate titer conditions.

2 Claims, 21 Drawing Sheets

Figure 1:
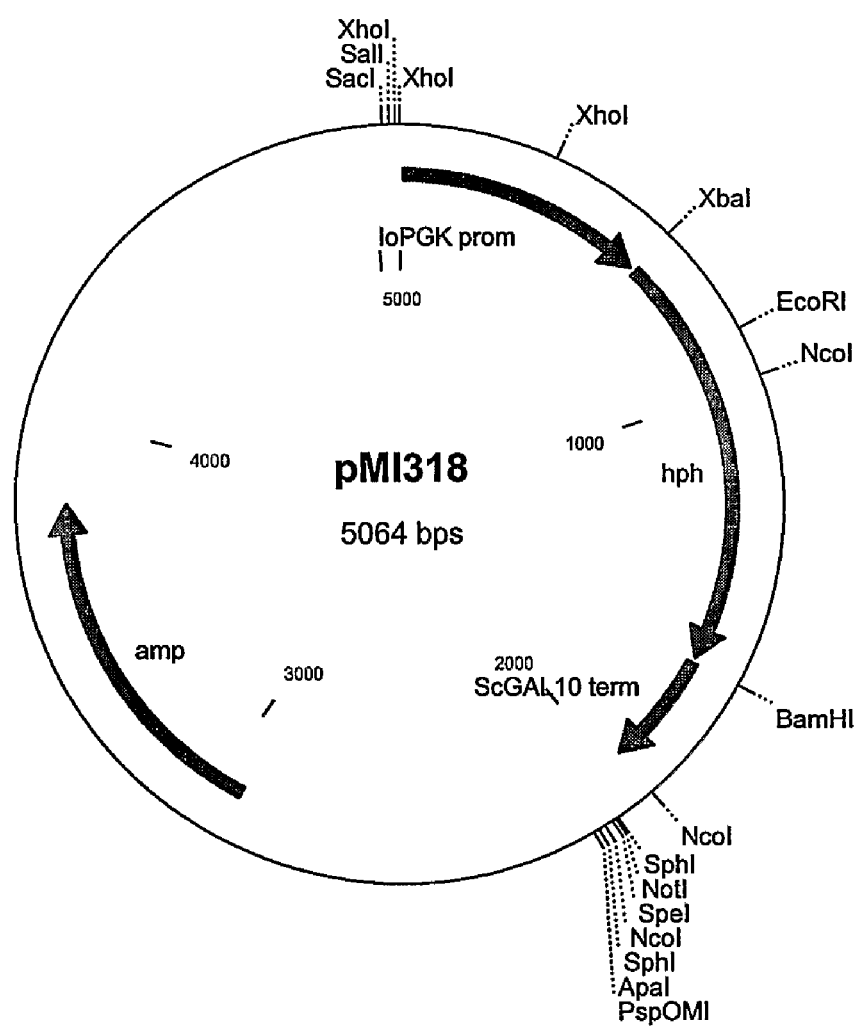

SEQUENCE LISTING

```
<160> NUMBER OF SEQ ID NOS: 97

<210> SEQ ID NO 1
<211> LENGTH: 23
<212> TYPE: DNA
<213> ORGANISM: Artificial Sequence
<220> FEATURE:
<223> OTHER INFORMATION: PGK  primer

<400> SEQUENCE: 1
aaccaaagaa ttgttgctgc ttt                                          23

<210> SEQ ID NO 2
<211> LENGTH: 25
<212> TYPE: DNA
<213> ORGANISM: Artificial Sequence
<220> FEATURE:
<223> OTHER INFORMATION: PGK primer.

<400> SEQUENCE: 2
ttcgaaaaca cctggtggac cgttc                                        25

<210> SEQ ID NO 3
<211> LENGTH: 25
<212> TYPE: DNA
<213> ORGANISM: Artificial Sequence
<220> FEATURE:
<223> OTHER INFORMATION: Linking primer

<400> SEQUENCE: 3
gcggtgaccc gggagatctg aattc                                        25

<210> SEQ ID NO 4
<211> LENGTH: 12
<212> TYPE: DNA
<213> ORGANISM: Artificial Sequence
<220> FEATURE:
<223> OTHER INFORMATION: Linking primer

<400> SEQUENCE: 4
gaattcagat ct                                                      12

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
gcggtgaccc gggagatctg aattc                                        25
```

```
<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
ccaattctgc agcaactggc tttaacg                                27

<210> SEQ ID NO 7
<211> LENGTH: 25
<212> TYPE: DNA
<213> ORGANISM: Artificial Sequence
<220> FEATURE:
<223> OTHER INFORMATION: Nested PCR Primer

<400> SEQUENCE: 7
gcggtgaccc gggagatctg aattc                                 25

<210> SEQ ID NO 8
<211> LENGTH: 21
<212> TYPE: DNA
<213> ORGANISM: Artificial Sequence
<220> FEATURE:
<223> OTHER INFORMATION: Nested PCR Primer

<400> SEQUENCE: 8
gcctcaccat ttggtctgcc c                                     21

<210> SEQ ID NO 9
<211> LENGTH: 25
<212> TYPE: DNA
<213> ORGANISM: Artificial Sequence
<220> FEATURE:
<223> OTHER INFORMATION: Nested PCR primer

<400> SEQUENCE: 9
gactccccgg agtgtcgaaa tatga                                 25

<210> SEQ ID NO 10
<211> LENGTH: 24
<212> TYPE: DNA
<213> ORGANISM: Artificial Sequence
<220> FEATURE:
<223> OTHER INFORMATION: Nested PCR primer

<400> SEQUENCE: 10
gtgatagcgg gtcctttcgc tacc                                  24

<210> SEQ ID NO 11
<211> LENGTH: 25
<212> TYPE: DNA
<213> ORGANISM: Artificial Sequence
<220> FEATURE:
<223> OTHER INFORMATION: Ligation-mediated PCR primer

<400> SEQUENCE: 11
gcggtgaccc gggagatctg aattc                                 25

<210> SEQ ID NO 12
<211> LENGTH: 12
<212> TYPE: DNA
<213> ORGANISM: Artificial Sequence
<220> FEATURE:
<223> OTHER INFORMATION: Ligation mediated PCR primer

<400> SEQUENCE: 12
```

```
gaattcagat ct                                                          12

<210> SEQ ID NO 13
<211> LENGTH: 36
<212> TYPE: DNA
<213> ORGANISM: Artificial Sequence
<220> FEATURE:
<223> OTHER INFORMATION: PGK 1 promoter amplification primer

<400> SEQUENCE: 13
gcgatctcga gatttgctgc aacggcaaca tcaatg                                36

<210> SEQ ID NO 14
<211> LENGTH: 36
<212> TYPE: DNA
<213> ORGANISM: Artificial Sequence
<220> FEATURE:
<223> OTHER INFORMATION: PGK 1 promotor amplification primer

<400> SEQUENCE: 14
ctagcatctg attgttgttg tcgttgtttt tgtttt                                36

<210> SEQ ID NO 15
<211> LENGTH: 36
<212> TYPE: DNA
<213> ORGANISM: Artificial Sequence
<220> FEATURE:
<223> OTHER INFORMATION: PGK1 amplification primer

<400> SEQUENCE: 15
gcgatctcga gatttgctgc aacggcaaca tcaatg                                36

<210> SEQ ID NO 16
<211> LENGTH: 36
<212> TYPE: DNA
<213> ORGANISM: Artificial Sequence
<220> FEATURE:
<223> OTHER INFORMATION: PGK1 amplification primer

<400> SEQUENCE: 16
acttggccat ggttgttgtt gttgtcgttg tttttg                                36

<210> SEQ ID NO 17
<211> LENGTH: 44
<212> TYPE: DNA
<213> ORGANISM: Artificial Sequence
<220> FEATURE:
<223> OTHER INFORMATION: PDC amplification primer

<400> SEQUENCE: 17
ccggaattcg atatctgggc wggkaatgcc aaygarttra atgc                       44

<210> SEQ ID NO 18
<211> LENGTH: 44
<212> TYPE: DNA
<213> ORGANISM: Artificial Sequence
<220> FEATURE:
<223> OTHER INFORMATION: PDC amplification primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 18
```
cgcggattca ggcctcagta ngaraawgaa ccngtrttra artc                     44

<210> SEQ ID NO 19
<211> LENGTH: 36
<212> TYPE: DNA
<213> ORGANISM: Artificial Sequence
<220> FEATURE:
<223> OTHER INFORMATION: PDC amplification primer

<400> SEQUENCE: 19
actgtcgagc tcagtatatg gaattgacgg ctcatc                              36

<210> SEQ ID NO 20
<211> LENGTH: 38
<212> TYPE: DNA
<213> ORGANISM: Artificial Sequence
<220> FEATURE:
<223> OTHER INFORMATION: PDC amplification primer

<400> SEQUENCE: 20
actgacgcgt cgacgtatca tttgtagccc acgccacc                            38

<210> SEQ ID NO 21
<211> LENGTH: 35
<212> TYPE: DNA
<213> ORGANISM: Artificial Sequence
<220> FEATURE:
<223> OTHER INFORMATION: PDC 3' flank amplification primer

<400> SEQUENCE: 21
cctcccccgg gctgatagaa gggtgatatg taatt                               35

<210> SEQ ID NO 22
<211> LENGTH: 24
<212> TYPE: DNA
<213> ORGANISM: Artificial Sequence
<220> FEATURE:
<223> OTHER INFORMATION: PDC 3' flank amplification primer

<400> SEQUENCE: 22
ccaagagtta tggggcccca gttg                                           24

<210> SEQ ID NO 23
<211> LENGTH: 49
<212> TYPE: DNA
<213> ORGANISM: Artificial Sequence
<220> FEATURE:
<223> OTHER INFORMATION: PDC 3' flank amplification primer

<400> SEQUENCE: 23
actgacgccc cgggtagtta gatagttggc tacccactta ccaagagat                49

<210> SEQ ID NO 24
<211> LENGTH: 35
<212> TYPE: DNA
<213> ORGANISM: Artificial Sequence
<220> FEATURE:
<223> OTHER INFORMATION: PDC 3' flank amplification primer

<400> SEQUENCE: 24
gggacgggcc caatagagag tgacctatcc aagct                               35

<210> SEQ ID NO 25
<211> LENGTH: 36
<212> TYPE: DNA
<213> ORGANISM: Artificial Sequence
<220> FEATURE:
<223> OTHER INFORMATION: PGK promoter amplification primer

<400> SEQUENCE: 25
gcgatctcga gatttgctgc aacggcaaca tcaatg    36

<210> SEQ ID NO 26
<211> LENGTH: 69
<212> TYPE: DNA
<213> ORGANISM: Artificial Sequence
<220> FEATURE:
<223> OTHER INFORMATION: PGK promoter amplification primer

<400> SEQUENCE: 26
tggactagta catgcatgcg gtgagaaagt agaaagcaaa cattgttgtt gttgttgtcg    60
ttgttttg    69

<210> SEQ ID NO 27
<211> LENGTH: 32
<212> TYPE: DNA
<213> ORGANISM: Artificial Sequence
<220> FEATURE:
<223> OTHER INFORMATION: Amplification primer for CYB2 gene

<400> SEQUENCE: 27
tccccggtcg accggaactt agcttactcg tc    32

<210> SEQ ID NO 28
<211> LENGTH: 32
<212> TYPE: DNA
<213> ORGANISM: Artificial Sequence
<220> FEATURE:
<223> OTHER INFORMATION: Amplification primer for CYB2 gene

<400> SEQUENCE: 28
ttgcgaggat cctgagtgca gtagctgtac ac    32

<210> SEQ ID NO 29
<211> LENGTH: 706
<212> TYPE: DNA
<213> ORGANISM: Kluyveromyces thermotolerans

<400> SEQUENCE: 29
cactcgcaag ctgtgccatc gcccaacggt taattataag aaatcaacat cagccaacaa    60 ctatttcgt cccctcttt tcagtggtaa cgagcaatta cattagtaag agactatttt    120
cttcagtgat ttgtaatttt ttttcagtga tttgtaattc tttctcgaaa tatgcgggct    180
waamtaatcc ggacattcac tacatgcaag gaaaaacgag aaccgcggag atttcctcag    240
taagtaacaa tgatgatctt tttacgcttc atcatcactt tccaaagttc taagctataa    300
gttcaagcct agatacgctg aaaaactcct gaccaacaat gtaaagaaaa caattacaat    360
tgtaaggttg aaaacatcta aaaatgaaat attttattgt acatgcacac cctgatagtc    420
attctcttac ttcatccctg aaagacgtgg ctgtacaaga gttggaatcg caaggtcatg    480
aggttaaagt tagtgatctt tatgctcaaa agtggaaggc ctcaatagac cgtgacgacw    540
wmaaaaaama aamrmaagaa gagaggttaa aaatacccca agcttcttat gaagcgtatg    600
ccagaggagc attaacaaaa gacgtaaatc aggaacagga aaaacttatt tgggcggact    660
ttgtcatttt gtcgtttcct atatggtggt cttctatgcc ggctag    706

<210> SEQ ID NO 30
<211> LENGTH: 30

```
<212> TYPE: DNA
<213> ORGANISM: Artificial Sequence
<220> FEATURE:
<223> OTHER INFORMATION: Amplification primer for K. thermotolerans
      sequence

<400> SEQUENCE: 30
tgtcagcatg cactcgcaag ctgtgccatc                                     30

<210> SEQ ID NO 31
<211> LENGTH: 33
<212> TYPE: DNA
<213> ORGANISM: Artificial Sequence
<220> FEATURE:
<223> OTHER INFORMATION: Amplification primer for K. thermotolerans
      sequence.

<400> SEQUENCE: 31
aaccttgtcg actagccggc atagaagacc acc                                 33

<210> SEQ ID NO 32
<211> LENGTH: 30
<212> TYPE: DNA
<213> ORGANISM: Artificial Sequence
<220> FEATURE:
<223> OTHER INFORMATION: Amplification primer for K. thermotolerans
      sequence

<400> SEQUENCE: 32
tgtcaggatc cactcgcaag ctgtgccatc                                     30

<210> SEQ ID NO 33
<211> LENGTH: 33
<212> TYPE: DNA
<213> ORGANISM: Artificial Sequence
<220> FEATURE:
<223> OTHER INFORMATION: Amplification primer for K. thermotolerans
      sequence

<400> SEQUENCE: 33
aaccttcccg ggtagccggc atagaagacc acc                                 33

<210> SEQ ID NO 34
<211> LENGTH: 20
<212> TYPE: DNA
<213> ORGANISM: Artificial Sequence
<220> FEATURE:
<223> OTHER INFORMATION: Amplification primer for CYB2 gene

<400> SEQUENCE: 34
ctggatctac agcgattctc                                                20

<210> SEQ ID NO 35
<211> LENGTH: 20
<212> TYPE: DNA
<213> ORGANISM: Artificial Sequence
<220> FEATURE:
<223> OTHER INFORMATION: Amplification primer for CYB2 gene

<400> SEQUENCE: 35
tgtaccggct gtccttaaac                                                20

<210> SEQ ID NO 36
<211> LENGTH: 4160
<212> TYPE: DNA
<213> ORGANISM: Issatchenkia orientalis
<220> FEATURE:
<221> NAME/KEY: misc_feature
```

```
<222> LOCATION: (609)..(609)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (1592)..(1592)
<223> OTHER INFORMATION: n is a, c, g, or t
<220> FEATURE:
<221> NAME/KEY: misc_feature
<222> LOCATION: (3716)..(3716)
<223> OTHER INFORMATION: n is a, c, g, or t
<220> FEATURE:
<221> NAME/KEY: misc_feature
<222> LOCATION: (3849)..(3849)
<223> OTHER INFORMATION: n is a, c, g, or t
<220> FEATURE:
<221> NAME/KEY: misc_feature
<222> LOCATION: (3903)..(3903)
<223> OTHER INFORMATION: n is a, c, g, or t

<400> SEQUENCE: 36
tcaaatagta tctcattgta tactaagata gtttgtattt gtgtgtgtgt gtcagtgtaa      60
gtgttagtat acttgttttc ctctttcccc tagagttggt ggtgtgtttt gttggaacgt     120
acattagatg cataatgcgt gacaccgcca tgatggttgt attctaccaa tgagacatgg     180
ccgctgatcc tgttgtgtgg gtcatgggac atcacctctt ggggggggatt ctcctataat     240 tggcaccgtg tatgcctcaa ccactaactt ccaccctata actgaatata ttacataagc     300
aaatctactt tttgtttgtg ttgatcgcca tcgttgaaat tcgcgcaact tctggtggct     360
caacgctgct gttctatcgg tatcctaaga gatgtctttg ccctgagtct agggtaaact     420
atccaccttc gttgctgttt gactagacag ctactaactt tacggtagta aatgaataac     480
ggctcgctct catgatcact tctctacatc accctaacaa gtgtattatt ttttttttcag     540 gtgggtgttg ctgttggtgc tagccttagt gccctcgtta atagttgaac aaacactggc     600
atttggagna taatgaaaag ggatcactac ccccgcttc ctgttccgct ctcccttcc     660 ggaaaaacca cccacccttt cttttccccc actaatgtat gaattttcc gttcccaggg     720 gaatggccca cttggttctc tgttaaccca cacaattttg acgcatcccn cacaccttt     780 ttttttcata ccccacactt tcccttgaaa atctccaatt tgaactggca atttcacccc     840
cccaccactt gcattcatta gtgagtcaat ccatcccgc ggtcggagat tcggaatcca     900
cctactggta atctgtaatc tatattcccg ctgaccctt ataaatganc tattgtcgtc     960
aattgcggta gtgctccaac aaattgtaag gaccttcttt aaccttttcg attcaatcca    1020
tctccacata aacctagttg cacacaatgt tactcgatc actaaactct tctgctcgtt    1080
gtgtcaaaca aacaaccaga acaaaggtta ggtatctcag ccacgtcagt ggtgcaagca    1140
tggcgaaacc tacattgaag aacaactcga gagaatccaa caaatccaga aactatctaa    1200
ttgctgctgt gacagcattg gctgtatcaa cctcaattgg agttgccgta catgtgaagg    1260 acccccttgta taacgatgct accggcagtg attctccgag aagtatatct gttgacgagt    1320
ttgtcaagca taattcacaa aacgactgtt ggattgcaat caatggcaag gtttatgatt    1380
tcactgattt tattccaaac catccaggtg gggtacctcc attagttaat catgctggtt    1440
atgatggtac taaacttat gagaaattgc atccaaaagg tacaattgag aaattcttgc    1500
caaaggataa gtttctgggt gtgttagatg gtgaagcgcc aaaattggaa gcagactatt    1560
```

```
tggttgacga tgatgaacaa gagcgactgg antatttggg caacttacct cctttgtcat  1620
ctattcagaa tgtttatgat ttcgaatact tggccaagaa gattttacct aaagatgcct  1680
gggcatatta ttcttgtggt gccgatgatg aaatcacaat gagagaaaac cattatgctt  1740
atcaaagagt ttatttcaga ccaagaattt gtgttgatgt caaggaagtt gatacttctt  1800
atgaaatgtt aggcactaaa acctctgttc ctttttatgt atctgccacc gctttggcta  1860
aattaggcca tcctgatggt gaatgctcaa ttgctagagg cgctggtaag gaaggtgtcg  1920
ttcaaatgat ttcgaccctt tcctcaatgt cattagatga aattgccgct gctagaattc  1980
caggtgcaac ccaatggttc caattataca ttaatgagga tagaaatgtc gctaaaggtc  2040
tggtcaaaca tgcagaagac ttgggtatga aggctatctt tataactgtt gatgctcctt  2100
ctctaggtaa cagagaaaag gataaaagat taaagtttgt taatgacacc gatgtcgatt  2160
tgggtgattc cgcagatcga acagtggtg cttcaaaggc actatcttcg ttcattgatg  2220
cttctgtctc ttggaatgac gtcaaagcgg tcaagtcgtg gactaaattg cctgtcttag  2280
ttaaaggtgt tcaaacagtt gaagacgtta ttgaagctta cgatgctggt tgtcaaggtg  2340
ttgttttgtc aaaccacggt ggtaggcaac tagatactgc tcctcctcca atcgaattat  2400
tagctgaaac tgttccaact ttgaagagat tgggtaaatt aagaccagat tttgaaattt  2460
taattgacgg tggtgtcaaa agaggtaccg atattttgaa agcagtcgca atcggtggcc  2520
aagatgtcag agtttcagtt ggtatgggta gaccttctt atatgccaac tcttgctatg  2580
gtgaagcagg tgttagaaaa ttaattcaaa atctaaagga tgaattagaa atggatatga  2640
gattgttggg tgtcactaaa atggaccagc tatcttcgaa acatgtcgat actaaacgtt  2700
tgattggtag agatgcgatc aactattgt atgataatgt atacagccca atcgaaaccg  2760
ttaaattcaa caatgaagat tgattgttgg aaatatatta ttcataaagg cgaaaacatt  2820
cccttggtat tttattccaa atttatgata catagacgta ttttttatat ataaagttat  2880
attattaatg attcaagaaa aagttcaaat aaactaatgg atcaacctat ttcgaccctt  2940
tcttcattgc tacttcttcc ttaagcaaca gatgattaag tagatactgt ttttttagcc  3000
aatagtatct cgccgaggag ttatacttga ctagctcttg ctcaagaatc ttcctaagac  3060
gtactagcct agcatagtaa tctgtttgtt tctgtattgt ttgttctaac tgttctacag  3120
tcattgaatc aatatctcca atgtcttcga cgttgacaac tttcccccc ttggcagcat  3180
tctcttttt gttggaatac gacattaaag attccttgat tttctgggta ccttcaatga  3240
ccattgaggg attaaatttg atttctttga ttttataatg gtcggctatt agctcttcca  3300
cttcgtcatc atgatcatca gatatgtcac gttgcctttt caatttatta aaattgttta  3360
tcagtttatt gtgatcttgt atcaattcat tgcgtactct tttctcaata tcaaaagcta  3420
ttttcttccc gctagactca aaatcaactc tgaagtcatt ttctcgctgg aattcatgta  3480
tttcatggat taattctcta ttgatattct catatgcatc ctgtaaactg ttgccgttga  3540
tattatgaac cgccttaaa tgtttcaata aggcatctgc tctagtaaat gccttcagac  3600
attcaggtaa taaacagtaa aatggcttct cggctgtatg cgtcctaata tgagacaata  3660
gcgcaaatct actgtgttgt ggagtaccat atcttggaca atttccccac ttacangaat  3720
ggtctgtgtt gggttgttta aaatgattag tattcatgtg attaaccatc tcatccattt  3780
ctctgaactg tgtcgagcag tcgtcccaac ggcaaatatg aatatctttg ggatccaatt  3840
ttgcctctnc ctccgaaata gtgtccttgt ctgattttag cctaaggcag tccatacttt  3900
tgnactcttg ttcgagatcc tcatcggtta tccgcctagc aaacactata tcacttgtca  3960
```

| | |
|---|---|
| tcagttctga tggtatgttc attcccaata agttgccgcc tttcctgtct aaacttcgtg | 4020 |
| tttcgttact tctcctacta tccctcatga aaataaagta ctcattcaca ttcattcccc | 4080 |
| tgttttgaa tttctgtgtt ttcttttcgc tcacaaaaat tctcaatttt tcacttaatt | 4140 |
| agtttctcaa atattgaacg | 4160 |

<210> SEQ ID NO 37
<211> LENGTH: 3840
<212> TYPE: DNA
<213> ORGANISM: Issatchenkia orientalis
<220> FEATURE:
<221> NAME/KEY: misc_feature
<222> LOCATION: (2042)..(2042)
<223> OTHER INFORMATION: n is a, c, g, or t
<220> FEATURE:
<221> NAME/KEY: misc_feature
<222> LOCATION: (2044)..(2044)
<223> OTHER INFORMATION: n is a, c, g, or t
<220> FEATURE:
<221> NAME/KEY: misc_feature
<222> LOCATION: (2970)..(2970)
<223> OTHER INFORMATION: n is a, c, g, or t
<220> FEATURE:
<221> NAME/KEY: misc_feature
<222> LOCATION: (3240)..(3240)
<223> OTHER INFORMATION: n is a, c, g, or t
<220> FEATURE:
<221> NAME/KEY: misc_feature
<222> LOCATION: (3654)..(3654)
<223> OTHER INFORMATION: n is a, c, g, or t

<400> SEQUENCE: 37

| | |
|---|---|
| gcattaaaaa acattaacat tcgccacatt cgacacattc gctgcattcg ccacaacgtc | 60 |
| acgtgaggca tcgtagtttt gagttttttt tttttgataa atctcgtttc ctgtgatatg | 120 |
| tttgccgtgc gcctggtcga ttttcacctt ctttgaaatc cgagttcggg aatgcaattg | 180 |
| ggaaaaagcc aaggagaaag aaaacaaaaa gagagttgcg tagaaactcg gaatgctcga | 240 |
| agaaaccaga cagttgatgg ctggtttccg ttttgaggac gcttggtgtg tgtaacttgg | 300 |
| atttgcacac tagagccgtc tctgcattgt attaaggtgt aaggacggtg aatcatcgcg | 360 |
| atggagcggg gttttttctt ttggcaggtt tttccgcgga aggcgagagg cggaagggg | 420 |
| gggggtgta tgtagttcat atttcggcat tactacaagg atgtttccgt acattgcatg | 480 |
| gtactggggt tctccttttc ttgcacatct ccataaacta aatatcaata gatgtatccg | 540 |
| tttggaatct catgactttt ggtgtgtggt ctgtgtcttc ccagttatct acttgagtga | 600 |
| ttatgaacca gttttcacca ttggttacat accaaacaga gaacttatac gcaccagaac | 660 |
| gccttttgtg tcttttgtt tctcaagtat ttctatcagt ttccttcatg tatcccggga | 720 |
| ctccattgtc ctcggtagtg cctaccaatt taatgtttga ctcctgcgtt ttctcctgtc | 780 |
| gcggacaaac ggtgcggctc ccccgatgat tcacgtaata agccggagtc aaccacagag | 840 |
| gtcccctatg actcaacaag gcctcgtaga aactcggctt tcggagaaa gagtctttc | 900 |
| tttttcactg gaaatatttt ttttttcct ttatattctt ttgaaccaaa atgtggctac | 960 |
| tataaaagtg cctttattcc ccagcttttc tagcatgatt gagtccacctt ccacaatgag | 1020 |
| tcttctttgt tgttagtatt gtgaatatta tccgtgcagt tttcaagaac gttaatcaac | 1080 |
| agcagtgata ataccttcaa aatgttaaga tcccagttca aaaacatttt gaaaaatgtt | 1140 |
| aacaagaacc attctctaag gagaactttt acttccagca cctcaaaggc tggaaaaaat | 1200 |
| gcttcataca atgccaagat tatatctgca accgtgccct cgattgttgc agcagctggc | 1260 |
| tcttatatgt tggtccagcc ttcactagct aatgatgagg cacagtctgc taatccaact | 1320 |

```
aggaagatct ctgttgacga atttgttaaa cacaaccatg ccgatgattg ttggatcact   1380
gttaacggta acgtctatga cttgactgat ttcatttcaa tgcatccagg tggtactacc   1440
ccattgattc aaaatgcagg tcacgacgca actgaaattt acaacaagat tcatccaaag   1500
ggtacaatcg agaacttctt accaaaggaa aagcaattgg gtgttttgga tggtgaagct   1560
cctaaaatcg aagttgtgct tgacgaaaag gagaaacaca gattggagtt gttgaatcat   1620
ctccctgctc tttccagaat tcaaaacatt tatgatttcg aacatattgc ttctagagtt   1680
ttgagcgacc aagcatggaa ctactattca tgtggtgccg aagatgaaat caccttgagg   1740
gaaaatcatt atgcttacca agaatctac tttaagccaa aatgttgtgt caatgttgca   1800
gaagttgata cctctcatga aattttaggt acaaaagctt ctgttccttt ctacgtttcc   1860
gcagccgctt ctgcaaagtt ggggcacgag gatggtgaat gttccattgc tagaggtgca   1920
ggtaaggaag gcgttattca aatgatttct tccttctctt ccaactcttt ggaggaaatt   1980
gcagaatcca gaattcctgg tgcaacacaa tggtttcaat tatacgttaa tgaagacaag   2040
gntnttgtga agaagacttt aaaaagggcc gaaaacttgg gtatgaaggc catctttgtc   2100
actgtggacg ctgctagtag aggtaataga gaaaaagaca ttacaatgag aattaccgaa   2160
gatacagatg agttaataga cgattcttct gttagagctg gttctacctc tggtgcattg   2220
ccagctttca ttgacaagag gctgacttgg gatgaagtta aggatatcat ttcatggacc   2280
aagttaccag ttttgctgaa gggtgttcaa agaactgatg atattgagaa ggcaattgat   2340
attggttgta agggtgttgt cttgtccaat catggtggta gacaattaga tacttctcct   2400
cctccaatag aagttatggc tgaatctgtt ccaatcctaa agcaaaaggg taaactggat   2460
ccaaatttca gtattttcgt tgatggtggt gttagaagag gtacagatat tttgaaagct   2520
ttggctattg gtggcagaga ctgtaaagtt gctgttggtc tgggtagacc tttcctttat   2580
gcaaatactg gttatggtga aaagggtgtc agaaaggccg tgcaaattct aagagaagaa   2640
ttaaaggctg acatgagaat gttgggcgtt acctctttga acgagctaga cgactcttac   2700
attgacacca gaagattact aggtagagat gctgttaacc acatatacaa caacaactac   2760
tacccaatgt ctaagattca attcaaaaac gaaaaataag tctgatattt gctaaattga   2820
aatgaacctt accatgccac atctatagac atcaaaacca ttttcaattt gtcgatatct   2880
tttgcatatc aaagtaatac caagcatgtt caaaaagaaa agaaagcata actttaatac   2940
tctattcgaa acactccgat ccacaacacn ttagtctttt tagacccgtt gttcatcttt   3000
ctattacttt attcctaact gtattttat aattccgggt ttataaaaga ttaaactaat   3060
atagcgcatt cttttggt acaaacatac ataacggagc tcattcatac atcgcttttc   3120
agttccgact ggtgtttcgg atgcctcttt ttctaaggag ctagattctg gccccacact   3180
agtctttgaa ctcgttgctc ccttaccacc cttaccacca gccttacttg taggtttttn   3240
agtagcatac tctgcgtgtt tgactaaatt cccttcctta actttgtgcc agcttggcca   3300
tatcattaaa tacccactga aacttctaac aactcttcga ccttcctgat gggcctttga   3360
aattgtatct accaaacctg ccttcaaggg atgttcttta tatcccctga cgtctttcat   3420
actttgaact tcctctggga cgtcttcctt tccatatttt tcccattggc ccggcttgtt   3480
tttagatttg tctatctcac ggaaaattga ggggttcata cttaatccac tcacaccaac   3540
cctgatgtta gaagacagtt ttgctaaatt atttacattc tgacttgtgt ttgtcgatat   3600
aactgaatca gatggtttca tcgatgattc tcgggagact ggttctgatg gcgntcaccg   3660
gggtctcaga tgctgctgga tttagcttta atttgagccg tttaataggt tcttcattta   3720
```

```
atgtttgttt tctttttttg tcgtagaaat gtgctgtgag atcaggaaat tgttcaagct    3780
gttcacgact tagttttagg gtgacatact tggttttttt aggtgccatt tctgtacaac    3840
```

<210> SEQ ID NO 38
<211> LENGTH: 33
<212> TYPE: DNA
<213> ORGANISM: Artificial Sequence
<220> FEATURE:
<223> OTHER INFORMATION: Amplification primer for MEL5 gene

<400> SEQUENCE: 38

```
aaaaaagtcg accgataaca agctcatgca aag                                 33
```

<210> SEQ ID NO 39
<211> LENGTH: 32
<212> TYPE: DNA
<213> ORGANISM: Artificial Sequence
<220> FEATURE:
<223> OTHER INFORMATION: Amplification primer for MEL5 gene

<400> SEQUENCE: 39

```
aaaaaaagat ctgcgtaacg aaataaatcc gc                                  32
```

<210> SEQ ID NO 40
<211> LENGTH: 32
<212> TYPE: DNA
<213> ORGANISM: Artificial Sequence
<220> FEATURE:
<223> OTHER INFORMATION: Amplification Primer for CYB2 3' flank

<400> SEQUENCE: 40

```
aaaaaacccg ggcttcctcc gctgcaggtt ca                                  32
```

<210> SEQ ID NO 41
<211> LENGTH: 32
<212> TYPE: DNA
<213> ORGANISM: Artificial Sequence
<220> FEATURE:
<223> OTHER INFORMATION: Amplification primer for CYB2 3' flank

<400> SEQUENCE: 41

```
aaaaaagagc tcgaagtctc tggatcctct tc                                  32
```

<210> SEQ ID NO 42
<211> LENGTH: 33
<212> TYPE: DNA
<213> ORGANISM: Artificial Sequence
<220> FEATURE:
<223> OTHER INFORMATION: Amplification Primer for CYB2 5' flank.

<400> SEQUENCE: 42

```
aaaaaagacg tcctggctcg atacttctta ttc                                 33
```

<210> SEQ ID NO 43
<211> LENGTH: 32
<212> TYPE: DNA
<213> ORGANISM: Artificial Sequence
<220> FEATURE:
<223> OTHER INFORMATION: Amplification Primer for CYB2 5' flank

<400> SEQUENCE: 43

```
aaaaaaggcg ccgctggcag atactagttc ag                                  32
```

<210> SEQ ID NO 44
<211> LENGTH: 34

```
<212> TYPE: DNA
<213> ORGANISM: Artificial Sequence
<220> FEATURE:
<223> OTHER INFORMATION: Amplification primer for K. thermotolerans
      sequence

<400> SEQUENCE: 44
tggactagtc actcgcaagc tgtgccatcg ccca                              34

<210> SEQ ID NO 45
<211> LENGTH: 37
<212> TYPE: DNA
<213> ORGANISM: Artificial Sequence
<220> FEATURE:
<223> OTHER INFORMATION: Amplification Primer for K. thermotolerans
      sequence

<400> SEQUENCE: 45
ggcccgcggc cgctagccgg catagaagac caccata                           37

<210> SEQ ID NO 46
<211> LENGTH: 39
<212> TYPE: DNA
<213> ORGANISM: Artificial Sequence
<220> FEATURE:
<223> OTHER INFORMATION: Amplification Primer for K. thermotolerans
      sequence

<400> SEQUENCE: 46
actgacgcgt cgaccactcg caagctgtgc catcgccca                         39

<210> SEQ ID NO 47
<211> LENGTH: 38
<212> TYPE: DNA
<213> ORGANISM: Artificial Sequence
<220> FEATURE:
<223> OTHER INFORMATION: Amplification Primer for K. thermotolerans
      sequence

<400> SEQUENCE: 47
actgacgcgt cgactagccg gcatagaaga ccaccata                          38

<210> SEQ ID NO 48
<211> LENGTH: 42
<212> TYPE: DNA
<213> ORGANISM: Artificial Sequence
<220> FEATURE:
<223> OTHER INFORMATION: Amplification primer for CYB2 3' flank

<400> SEQUENCE: 48
cctcccccgg ggatatcaaa gttatattat taatgattca ag                     42

<210> SEQ ID NO 49
<211> LENGTH: 43
<212> TYPE: DNA
<213> ORGANISM: Artificial Sequence
<220> FEATURE:
<223> OTHER INFORMATION: Amplification Primer for CYB2 3' flank

<400> SEQUENCE: 49
ggacgagagc tcgggcccat gacttcagag ttgattttga gtc                    43

<210> SEQ ID NO 50
<211> LENGTH: 20
<212> TYPE: DNA
<213> ORGANISM: Artificial Sequence
<220> FEATURE:
<223> OTHER INFORMATION: URA3 gene amplification primer
```

```
<400> SEQUENCE: 50
aagmaracha ayttrtgtgc                                                  20

<210> SEQ ID NO 51
<211> LENGTH: 19
<212> TYPE: DNA
<213> ORGANISM: Artificial Sequence
<220> FEATURE:
<223> OTHER INFORMATION: URA3 gene amplification primer

<400> SEQUENCE: 51
aaharkcctc tccaacaat                                                   19

<210> SEQ ID NO 52
<211> LENGTH: 2880
<212> TYPE: DNA
<213> ORGANISM: Issatchenkia orientalis
<220> FEATURE:
<221> NAME/KEY: misc_feature
<222> LOCATION: (2747)..(2747)
<223> OTHER INFORMATION: n is a, c, g, or t
<220> FEATURE:
<221> NAME/KEY: misc_feature
<222> LOCATION: (2866)..(2866)
<223> OTHER INFORMATION: n is a, c, g, or t

<400> SEQUENCE: 52
gaaggtaatt ccataagtgt gagtgtaccg cacaaccatc atggatatac aaaagatcaa       60
actaatgata atgaaggcaa aaggaaactt gatgatggag atgtagaaga ggcacgtgac      120
agcaaaatct tgaagaagcc aaaaacagag gaaacttcaa tcgtcgaaga agataagcca      180
caaattaggt tgaggaccag aagtatggtt aataatgaaa acacagtcaa aaaatttcag      240
caattatccc tacctatact aacaaatatt tcgtcgcatc gtatcgcttc aatgtttttg      300
acgccagtca atgctatgga agagcctgat tattttaaag taattaagaa accaattgac      360
ttgaagacta ataaaaaaa ggtcaggaac ttttctataa acaccctcga agagcttgaa       420
tttgaaatgc aactgatgtt cacgaatgcg ataatgtaca atacaagtga taagttgaa       480 ggaatatcgg atatgatgaa agaatggcaa gatctagtag taatattgaa agaaaatatg      540
taataggtat agtccgtcag ttatattgga agataataag aaaagaatat caaaactatt      600
taattagtta attgtataaa ctgtatgtca ttataaacag ggaaggttga cattgtctag      660
cggcaatcat tgtctcattt ggttcattaa cttttggttc tgttcttgga aacgggtacc      720
aactctctca gagtgcttca aaaatttttc agcacatttg gttagacatg aactttctct      780
gctggttaag gattcagagg tgaagtcttg aacacaatcg ttgaaacatc tgtccacaag      840
agatgtgtat agcctcatga aatcagccat ttgcttttgt tcaacgatct tttgaaattg      900
ttgttgttct tggtagttaa gttgatccat cttggcttat gttgtgtgta tgttgtagtt      960
attcttagta tattcctgtc ctgagtttag tgaaacataa tatcgccttg aaatgaaaat     1020
gctgaaattc gtcgacatac aattttttcaa actttttttt tttcttggtg cacggacatg     1080
tttttaaagg aagtactcta taccagttat tcttcacaaa tttaattgct ggagaataga     1140
tcttcaacgc tttaataaag tagtttgttt gtcaaggatg gcgtcataca aagaaagatc     1200
agaatcacac acttcccctg ttgctaggag acttttctcc atcatggagg aaaagaagtc     1260 taaccttgt gcatcattgg atattactga aactgaaaag cttctctcta ttttggacac      1320
tattggtcct tacatctgtc tagttaaaac acacatcgat attgtttctg attttacgta     1380
tgaaggaact gtgttgcctt tgaaggagct tgccaagaaa cataatttta tgattttga     1440
```

```
agatagaaaa tttgctgata ttggtaacac tgttaaaaat caatataaat ctggtgtctt    1500
ccgtattgcc gaatgggctg acatcactaa tgcacatggt gtaacgggtg caggtattgt    1560
ttctggcttg aaggaggccg cccaagaaac aaccagtgaa cctagaggtt tgctaatgct    1620
tgctgagtta tcatcaaagg gttctttagc atatggtgaa tatacagaaa aaacagtaga    1680
aattgctaaa tctgataaag agtttgtcat tggttttatt gcgcaacacg atatgggcgg    1740
tagagaagaa ggttttgact ggatcattat gactccaggg gttggtttag atgacaaagg    1800
tgatgcactt ggtcaacaat atagaactgt tgatgaagtt gtaaagactg gaacggatat    1860
cataattgtt ggtagaggtt tgtatggtca aggaagagat cctgtagagc aagctaaaag    1920
ataccaacaa gctggttgga atgcttattt aaacagattt aaatgattct tacacaaaga    1980
tttgatacat gtacactagt ttaaataagc atgaaaagaa ttacacaagc aaaaaaaaat    2040
taaatgaggt actttacgtt cacctacaac caaaaaaact agatagagta aaatcttatg    2100
atttagaaaa agttgtttaa caaaggcttt agtatgtgaa ttttaatgt agcaaagcga     2160 taactaataa acataaacaa aagtatggtt ttctttatca gtcaaatcat tatcgattga    2220
ttgttccgcg tattctaagt gttttatatc attcatagtt aacgattgct tttgtttatt    2280
ctgtattctc agcataagat agtaaaggat accggtgaac gccataattg aaaaggaagc    2340
ttccatggca tgtatcccca tcggatactt tggtgcttga gaacctttga aaaaatatgg    2400
accgataatg ttaccaactg cataccaaac tgcaacagaa acatacatga acgtcttctt    2460
ggtagatcct gaggtgtttg aagataccaa cgccaacatt aatgtccatg cacattgta    2520 gaatcccatc aaataaattc cagctaatgc agcatgtcga ttttcgtgtg atcaatctt    2580 atttaccata atagcccccag ctaaagcagg tagacacgtt aatacccaca ataaacacct   2640
aatattatga atccacatgc agattgctgt tatcagcata ccacctccca aggcaactgc    2700
tgcctgagga gacgccataa gtgttgtttt gagagcagaa aacccanaac ctttgattat    2760
aagaggattg aaatttgtta gtcccgaatt acagatggac tgacatataa taaatgcaac    2820
aacaatataa tatttgggat ccaacaaagc ctcccagatt tgatanattt tcaatttgtg    2880
```

<210> SEQ ID NO 53
<211> LENGTH: 262
<212> TYPE: PRT
<213> ORGANISM: Issatchenkia orientalis

<400> SEQUENCE: 53

```
Met Ala Ser Tyr Lys Glu Arg Ser Glu Ser His Thr Ser Pro Val Ala
1               5                   10                  15

Arg Arg Leu Phe Ser Ile Met Glu Glu Lys Lys Ser Asn Leu Cys Ala
            20                  25                  30

Ser Leu Asp Ile Thr Glu Thr Glu Lys Leu Leu Ser Ile Leu Asp Thr
        35                  40                  45

Ile Gly Pro Tyr Ile Cys Leu Val Lys Thr His Ile Asp Ile Val Ser
    50                  55                  60

Asp Phe Thr Tyr Glu Gly Thr Val Leu Pro Leu Lys Glu Leu Ala Lys
65                  70                  75                  80

Lys His Asn Phe Met Ile Phe Glu Asp Arg Lys Phe Ala Asp Ile Gly
                85                  90                  95

Asn Thr Val Lys Asn Gln Tyr Lys Ser Gly Val Phe Arg Ile Ala Glu
            100                 105                 110

Trp Ala Asp Ile Thr Asn Ala His Gly Val Thr Gly Ala Gly Ile Val
        115                 120                 125
```

Ser Gly Leu Lys Glu Ala Ala Gln Glu Thr Thr Ser Glu Pro Arg Gly
    130                 135                 140

Leu Leu Met Leu Ala Glu Leu Ser Ser Lys Gly Ser Leu Ala Tyr Gly
145                 150                 155                 160

Glu Tyr Thr Glu Lys Thr Val Glu Ile Ala Lys Ser Asp Lys Glu Phe
                165                 170                 175

Val Ile Gly Phe Ile Ala Gln His Asp Met Gly Gly Arg Glu Glu Gly
            180                 185                 190

Phe Asp Trp Ile Ile Met Thr Pro Gly Val Gly Leu Asp Asp Lys Gly
        195                 200                 205

Asp Ala Leu Gly Gln Gln Tyr Arg Thr Val Asp Glu Val Val Lys Thr
    210                 215                 220

Gly Thr Asp Ile Ile Ile Val Gly Arg Gly Leu Tyr Gly Gln Gly Arg
225                 230                 235                 240

Asp Pro Val Glu Gln Ala Lys Arg Tyr Gln Gln Ala Gly Trp Asn Ala
                245                 250                 255

Tyr Leu Asn Arg Phe Lys
            260

<210> SEQ ID NO 54
<211> LENGTH: 34
<212> TYPE: DNA
<213> ORGANISM: Artificial Sequence
<220> FEATURE:
<223> OTHER INFORMATION: Amplifciation primer for URA3 3' flank

<400> SEQUENCE: 54
ctcccccggg caacaaagcc tcccagattt gata                        34

<210> SEQ ID NO 55
<211> LENGTH: 34
<212> TYPE: DNA
<213> ORGANISM: Artificial Sequence
<220> FEATURE:
<223> OTHER INFORMATION: Amplification Primer for URA3 3' flank

<400> SEQUENCE: 55
ggacgggccc cctaggtatt gcggctgttt atac                        34

<210> SEQ ID NO 56
<211> LENGTH: 43
<212> TYPE: DNA
<213> ORGANISM: Artificial Sequence
<220> FEATURE:
<223> OTHER INFORMATION: Amplification Primer for URA3 5' flank

<400> SEQUENCE: 56
ggacatgcat gcgagctctc aaaactattt aattagttaa ttg              43

<210> SEQ ID NO 57
<211> LENGTH: 52
<212> TYPE: DNA
<213> ORGANISM: Artificial Sequence
<220> FEATURE:
<223> OTHER INFORMATION: Amplification Primer for URA3 5' flank

<400> SEQUENCE: 57
ggacatgcat gctacgtacc ctgcagggtg aagaataact ggtatagagt ac    52

<210> SEQ ID NO 58
<211> LENGTH: 28
<212> TYPE: DNA

```
<213> ORGANISM: Artificial Sequence
<220> FEATURE:
<223> OTHER INFORMATION: URA 3 screening primer

<400> SEQUENCE: 58
gatatgatga aagaatggca agatctag                                28

<210> SEQ ID NO 59
<211> LENGTH: 26
<212> TYPE: DNA
<213> ORGANISM: Artificial Sequence
<220> FEATURE:
<223> OTHER INFORMATION: URA3 screening primer

<400> SEQUENCE: 59
sattgctcgt taccactgaa aagagg                                  26

<210> SEQ ID NO 60
<211> LENGTH: 21
<212> TYPE: DNA
<213> ORGANISM: artificial sequence
<220> FEATURE:
<223> OTHER INFORMATION: Degenerative primer

<400> SEQUENCE: 60
ggkgctaach tbgcymcmga r                                       21

<210> SEQ ID NO 61
<211> LENGTH: 21
<212> TYPE: DNA
<213> ORGANISM: artificial sequence
<220> FEATURE:
<223> OTHER INFORMATION: Degenerative primer

<400> SEQUENCE: 61
dgtratbara tcrgcvacac c                                       21

<210> SEQ ID NO 62
<211> LENGTH: 21
<212> TYPE: DNA
<213> ORGANISM: Artificial sequence
<220> FEATURE:
<223> OTHER INFORMATION: Degenerative oligo

<400> SEQUENCE: 62
krtygghycy ggtaactggg g                                       21

<210> SEQ ID NO 63
<211> LENGTH: 21
<212> TYPE: DNA
<213> ORGANISM: artificial sequence
<220> FEATURE:
<223> OTHER INFORMATION: Degenerative oligo

<400> SEQUENCE: 63
rtgraagtad ggtckgtgga a                                       21

<210> SEQ ID NO 64
<211> LENGTH: 27
<212> TYPE: DNA
<213> ORGANISM: Artificial Sequence
<220> FEATURE:
<223> OTHER INFORMATION: PCR forward primer

<400> SEQUENCE: 64
ccattgccgg tgcactcaag aatgtcg                                 27
```

<210> SEQ ID NO 65
<211> LENGTH: 27
<212> TYPE: DNA
<213> ORGANISM: Artificial Sequence
<220> FEATURE:
<223> OTHER INFORMATION: PCR reverse primer

<400> SEQUENCE: 65
cgacattctt gagtgcaccg gcaatgg                                27

<210> SEQ ID NO 66
<211> LENGTH: 27
<212> TYPE: DNA
<213> ORGANISM: Artificial Sequence
<220> FEATURE:
<223> OTHER INFORMATION: Nested PCR Primer

<400> SEQUENCE: 66
ggctgctgga tttgtcgaag gtttagg                                27

<210> SEQ ID NO 67
<211> LENGTH: 27
<212> TYPE: DNA
<213> ORGANISM: Artificial Sequence
<220> FEATURE:
<223> OTHER INFORMATION: Nested PCR Primer

<400> SEQUENCE: 67
ccttgccttt acctctgaaa tcgtccg                                27

<210> SEQ ID NO 68
<211> LENGTH: 42
<212> TYPE: DNA
<213> ORGANISM: Artificial Sequence
<220> FEATURE:
<223> OTHER INFORMATION: CYB2 3' flank PCR primer

<400> SEQUENCE: 68
cctcccccgg ggatatcaaa gttatattat taatgattca ag               42

<210> SEQ ID NO 69
<211> LENGTH: 43
<212> TYPE: DNA
<213> ORGANISM: Artificial Sequence
<220> FEATURE:
<223> OTHER INFORMATION: CYB2 3' flank PCR primer

<400> SEQUENCE: 69
ggacgagagc tcgggcccat gacttcagag ttgattttga gtc              43

<210> SEQ ID NO 70
<211> LENGTH: 44
<212> TYPE: DNA
<213> ORGANISM: Artificial Sequence
<220> FEATURE:
<223> OTHER INFORMATION: CYB2 5' flank primer

<400> SEQUENCE: 70
ggacatgcat gcgagctcaa tgcgtgacac cgccatgatg gttg             44

<210> SEQ ID NO 71
<211> LENGTH: 52
<212> TYPE: DNA
<213> ORGANISM: Artificial Sequence
<220> FEATURE:
<223> OTHER INFORMATION: CYB2 5' flank primer

```
<400> SEQUENCE: 71
ggacatgcat gctacgtacc ctgcagggca ccaacagcaa cacccacctg aa          52

<210> SEQ ID NO 72
<211> LENGTH: 43
<212> TYPE: DNA
<213> ORGANISM: Artificial Sequence
<220> FEATURE:
<223> OTHER INFORMATION: CYB2 5' flank primer

<400> SEQUENCE: 72
ggacatgcat gcgagctcat agttgaacaa acactggcat ttg                   43

<210> SEQ ID NO 73
<211> LENGTH: 52
<212> TYPE: DNA
<213> ORGANISM: Artificial Sequence
<220> FEATURE:
<223> OTHER INFORMATION: CYB2 5' flank primer

<400> SEQUENCE: 73
ggacatgcat gctacgtacc ctgcaggtgt gtgcaactag gtttatgtgg ag          52

<210> SEQ ID NO 74
<211> LENGTH: 53
<212> TYPE: DNA
<213> ORGANISM: Artificial Sequence
<220> FEATURE:
<223> OTHER INFORMATION: CYB2 3' flank primer

<400> SEQUENCE: 74
cctcccccgg ggatatctag ttagatagct cctcctccaa tcgaattatt agc         53

<210> SEQ ID NO 75
<211> LENGTH: 42
<212> TYPE: DNA
<213> ORGANISM: Artificial Sequence
<220> FEATURE:
<223> OTHER INFORMATION: CYB2 3' flank primer

<400> SEQUENCE: 75
ggacgagagc tcgggcccta cgtctatgta tcataaattt gg                    42

<210> SEQ ID NO 76
<211> LENGTH: 33
<212> TYPE: DNA
<213> ORGANISM: Artificial Sequence
<220> FEATURE:
<223> OTHER INFORMATION: GPD1 gene primer

<400> SEQUENCE: 76
aaaaaacata tggagatgtt aatatgtggg tct                              33

<210> SEQ ID NO 77
<211> LENGTH: 33
<212> TYPE: DNA
<213> ORGANISM: Artificial Sequence
<220> FEATURE:
<223> OTHER INFORMATION: GPD1 primer

<400> SEQUENCE: 77 tttttttcctg caggtcagta ataacagtgg aga                             33

<210> SEQ ID NO 78
<211> LENGTH: 30
<212> TYPE: DNA
```

```
<213> ORGANISM: Artificial Sequence
<220> FEATURE:
<223> OTHER INFORMATION: GPD1 gene primer

<400> SEQUENCE: 78
aaaaaacccg gggtgcctta tcaggtgcta                                       30

<210> SEQ ID NO 79
<211> LENGTH: 30
<212> TYPE: DNA
<213> ORGANISM: Artificial Sequence
<220> FEATURE:
<223> OTHER INFORMATION: GPD1 primer

<400> SEQUENCE: 79 tttttttgaat tcaaggttgc agcatgacag                                      30

<210> SEQ ID NO 80
<211> LENGTH: 20
<212> TYPE: DNA
<213> ORGANISM: Artificial Sequence
<220> FEATURE:
<223> OTHER INFORMATION: GPD1 primer

<400> SEQUENCE: 80
gagttcaccc gtccagatag                                                  20

<210> SEQ ID NO 81
<211> LENGTH: 22
<212> TYPE: DNA
<213> ORGANISM: Artificial Sequence
<220> FEATURE:
<223> OTHER INFORMATION: GPD1 primer

<400> SEQUENCE: 81
ggacaacgta catggacgat tc                                               22

<210> SEQ ID NO 82
<211> LENGTH: 20
<212> TYPE: DNA
<213> ORGANISM: Artificial Sequence
<220> FEATURE:
<223> OTHER INFORMATION: GPD1 primer

<400> SEQUENCE: 82
ctatctggac gggtgaactc                                                  20

<210> SEQ ID NO 83
<211> LENGTH: 18
<212> TYPE: DNA
<213> ORGANISM: Artificial Sequence
<220> FEATURE:
<223> OTHER INFORMATION: GPD1 primer

<400> SEQUENCE: 83
ggactggggg tgtacaat                                                    18

<210> SEQ ID NO 84
<211> LENGTH: 20
<212> TYPE: DNA
<213> ORGANISM: Artificial Sequence
<220> FEATURE:
<223> OTHER INFORMATION: GPD1 primer

<400> SEQUENCE: 84
cttgtgcagg ctcagacttg                                                  20
```

```
<210> SEQ ID NO 85
<211> LENGTH: 20
<212> TYPE: DNA
<213> ORGANISM: Artificial Sequence
<220> FEATURE:
<223> OTHER INFORMATION: GPD1 primer

<400> SEQUENCE: 85
caaggcattc tggcagcttc                                              20

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
cggcttccaa agcggactta cc                                           22

<210> SEQ ID NO 87
<211> LENGTH: 22
<212> TYPE: DNA
<213> ORGANISM: Artificial Sequence
<220> FEATURE:
<223> OTHER INFORMATION: GPD1 primer

<400> SEQUENCE: 87
aaggccgaca gcccattcaa gg                                           22

<210> SEQ ID NO 88
<211> LENGTH: 44
<212> TYPE: DNA
<213> ORGANISM: Artificial Sequence
<220> FEATURE:
<223> OTHER INFORMATION: PDC1 primer

<400> SEQUENCE: 88
ccggaattcg atatctgggc wggkaatgcc aaygarttra atgc                   44

<210> SEQ ID NO 89
<211> LENGTH: 44
<212> TYPE: DNA
<213> ORGANISM: Artificial Sequence
<220> FEATURE:
<223> OTHER INFORMATION: PDC1 primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 89
cgcggattca ggcctcagta ngaraawgaa ccngtrttra artc                   44

<210> SEQ ID NO 90
<211> LENGTH: 28
<212> TYPE: DNA
<213> ORGANISM: Artificial Sequence
<220> FEATURE:
<223> OTHER INFORMATION: PDC1 sequencing primer

<400> SEQUENCE: 90
atggcaagag aggaaaaacc tcgtaaag                                     28
```

<210> SEQ ID NO 91
<211> LENGTH: 27
<212> TYPE: DNA
<213> ORGANISM: Artificial Sequence
<220> FEATURE:
<223> OTHER INFORMATION: PDC1 sequencing primer

<400> SEQUENCE: 91
ccacgaagag tcattgacga accttaa         27

<210> SEQ ID NO 92
<211> LENGTH: 714
<212> TYPE: DNA
<213> ORGANISM: Pichia membranifaciens

<400> SEQUENCE: 92
gggtatgaag ctgatggata ctccagagtc aacggctttg catgcctggt taccaccttc         60
ggtgtcggcg aattgtctgc tgtcaacgcc gttgcaggtg cgtatgcaga gcacattcca        120
ttaatccacg tggtcggtat gccttccatc tccgccgaga agcaaaagct tctacttcac        180
cacacgttag gtgattcgag gttcgatgat tttaccgcaa tgtcccagaa gatcagcatc        240
aagctcaagg ttatcactga gtttgacgat gcaccaaagg ttataaacga cttgattgaa        300
acagccatac tcaccaagag accggtttat ctcggttttcc caagtaactt ttcagaggca        360
ttgataccag cctccgattt gacaaagtac aagcttaagt tgtctttgcc tccaaacaat        420
gaagagtctg aaaatgagtt tgtggaaaac gttattcagc tgatggagaa ggctaagaac        480
cctgtgattt tggttgatgc ctgtgcttcc cgtcatgctg tcattgaaca agttgaagaa        540
gttgctagac ttacaaagtt cccagttttt accactccaa tgggtaaagg ctctttcaac        600
gaagacaata gcgaatatta cggtatgtac attggtgctt tatctgctcc tgatgttaag        660
gagatcgtcg agtccacaga ctgtatcatc tctatcggtg ggttattatc agat              714

<210> SEQ ID NO 93
<211> LENGTH: 957
<212> TYPE: DNA
<213> ORGANISM: Bacillus megaterium

<400> SEQUENCE: 93
atgaaaacac aatttacacc aaaaacacga aaagttgccg ttatcggaac tggttttgtt         60
ggctcaagct acgcttttttc aatggtgaat caaggtattg ccaatgaatt agtgttaatc        120
gatatgaaca agaaaaagc agaaggtgaa gcacgtgata tcaatcatgg aatgccatttt        180 gccacaccga tgaaaatctg gctggagat tataaagact gtgctgacgc tgatttagca        240
gttattacag cgggcgctaa tcaagctcca ggggaaacac gcttagatct agttgaaaaa        300
aacgttaaaa ttttcgaatg cattgtaaaa gatattatga acagcggatt tgacggcatc        360 atttagtgg caacaaatcc agttgatatt ctcgcacacg ttacacaaaa agtatcagga        420
ttaccaaacg gacgggtaat tggttcagga acgattcttg acacagctcg cttccgctac        480
ttgttaagcg actatttcga agtagattct cgcaacgtcc acgcttatat tatgggggaa        540
catggagata cggaatttcc tgtttggagc cacgcgcaaa ttggcggtgt gaagctcgaa        600
cattttatca atactgccgc tattgaaaaa gaaccggata tgcagcatct attcgaacaa        660
acccgcgatg cggcttacca tattattaat cgaaaaggag cgacttatta cggaattgca        720
atggggcttg tacgcattac caaggctatt ttagatgatg aaaattctat tttaacagta        780
tctgctttat tagaaggaca atacggtatt tctgatgtgt atatcggcgt accagctatc        840

```
attaataaaa acggcgtgcg tcaaattatt gaattgaatt taactcctca cgaacagcag    900
cagctcgagc actctgctag cattcttaag caaactcgcg acagagcttt tgtgtaa      957
```

<210> SEQ ID NO 94
<211> LENGTH: 972
<212> TYPE: DNA
<213> ORGANISM: Lactobacillus helveticus

<400> SEQUENCE: 94

```
atggcaagag aggaaaaacc tcgtaaagtt attttagtcg gtgatggtgc tgtaggttct    60
acctttgcat tttcaatggt acaacaaggt atcgctgaag aattaggtat tatcgatatc   120
gctaaggaac acgttgaagg tgacgcaatc gatttagctg acgcaactcc ttggacttct   180
ccaaagaaca tttacgcagc tgactaccca gattgtaagg atgctgactt agttgttatt   240
actgctggtg ctccacaaaa gccaggcgaa actcgtcttg atcttgttaa caagaacttg   300
aagattttat catcaatcgt tgaaccagtt gttgaatcag ttttgaagg tattttctta    360 gtagttgcta acccagttga tatcttaact cacgcaactt ggagaatgtc aggcttccct   420
aaggatcgtg ttatcggttc aggtacttca cttgatactg tcgtcttca aaaagttatt    480 ggtaaaatgg aaaacgttga cccaagttca gttaatgcat acatgcttgg tgaacacggt   540
gatactgaat cccagcatg gagctacaac aatgttgctg gcgtaaaggt tgctgactgg   600
gttaaggctc acaacatgcc tgaatctaag cttgaagaca tccaccaaga agttaaggac   660
atggcttacg acattattaa caagaaaggt gctaccttct acggtatcgg tactgcttca   720
gcaatgatcg ctaaggctat cttgaacgat gaacaccgtg tacttccact ttcagtacca   780
atggatggtg aatatggttt acacgatctt cacatcggta ctcctgcagt tgttggccgc   840
aagggtcttg aacaagttat cgaaatgcca ttaagcgata aggaacaaga attaatgact   900
gcttcagcag atcaattaaa gaaggttatg gacaaggcct tcaaagaaac tggcgttaag   960
gttcgtcaat aa                                                       972
```

<210> SEQ ID NO 95
<211> LENGTH: 318
<212> TYPE: PRT
<213> ORGANISM: Bacillus megaterium

<400> SEQUENCE: 95

```
Met Lys Thr Gln Phe Thr Pro Lys Thr Arg Lys Val Ala Val Ile Gly
  1               5                  10                  15

Thr Gly Phe Val Gly Ser Ser Tyr Ala Phe Ser Met Val Asn Gln Gly
             20                  25                  30

Ile Ala Asn Glu Leu Val Leu Ile Asp Met Asn Lys Glu Lys Ala Glu
         35                  40                  45

Gly Glu Ala Arg Asp Ile Asn His Gly Met Pro Phe Ala Thr Pro Met
     50                  55                  60

Lys Ile Trp Ala Gly Asp Tyr Lys Asp Cys Ala Asp Ala Asp Leu Ala
 65                  70                  75                  80

Val Ile Thr Ala Gly Ala Asn Gln Ala Pro Gly Glu Thr Arg Leu Asp
                 85                  90                  95

Leu Val Glu Lys Asn Val Lys Ile Phe Glu Cys Ile Val Lys Asp Ile
            100                 105                 110

Met Asn Ser Gly Phe Asp Gly Ile Ile Leu Val Ala Thr Asn Pro Val
        115                 120                 125

Asp Ile Leu Ala His Val Thr Gln Lys Val Ser Gly Leu Pro Asn Gly
    130                 135                 140
```

```
Arg Val Ile Gly Ser Gly Thr Ile Leu Asp Thr Ala Arg Phe Arg Tyr
145                 150                 155                 160

Leu Leu Ser Asp Tyr Phe Glu Val Asp Ser Arg Asn Val His Ala Tyr
                165                 170                 175

Ile Met Gly Glu His Gly Asp Thr Glu Phe Pro Val Trp Ser His Ala
            180                 185                 190

Gln Ile Gly Gly Val Lys Leu Glu His Phe Ile Asn Thr Ala Ala Ile
        195                 200                 205

Glu Lys Glu Pro Asp Met Gln His Leu Phe Glu Gln Thr Arg Asp Ala
210                 215                 220

Ala Tyr His Ile Ile Asn Arg Lys Gly Ala Thr Tyr Tyr Gly Ile Ala
225                 230                 235                 240

Met Gly Leu Val Arg Ile Thr Lys Ala Ile Leu Asp Asp Glu Asn Ser
                245                 250                 255

Ile Leu Thr Val Ser Ala Leu Leu Glu Gly Gln Tyr Gly Ile Ser Asp
            260                 265                 270

Val Tyr Ile Gly Val Pro Ala Ile Ile Asn Lys Asn Gly Val Arg Gln
        275                 280                 285

Ile Ile Glu Leu Asn Leu Thr Pro His Glu Gln Gln Gln Leu Glu His
290                 295                 300

Ser Ala Ser Ile Leu Lys Gln Thr Arg Asp Arg Ala Phe Val
305                 310                 315

<210> SEQ ID NO 96
<211> LENGTH: 323
<212> TYPE: PRT
<213> ORGANISM: Lactobacillus helveticus

<400> SEQUENCE: 96

Met Ala Arg Glu Glu Lys Pro Arg Lys Val Ile Leu Val Gly Asp Gly
1               5                   10                  15

Ala Val Gly Ser Thr Phe Ala Phe Ser Met Val Gln Gln Gly Ile Ala
                20                  25                  30

Glu Glu Leu Gly Ile Ile Asp Ile Ala Lys Glu His Val Glu Gly Asp
            35                  40                  45

Ala Ile Asp Leu Ala Asp Ala Thr Pro Trp Thr Ser Pro Lys Asn Ile
50                  55                  60

Tyr Ala Ala Asp Tyr Pro Asp Cys Lys Asp Ala Asp Leu Val Val Ile
65                  70                  75                  80

Thr Ala Gly Ala Pro Gln Lys Pro Gly Glu Thr Arg Leu Asp Leu Val
                85                  90                  95

Asn Lys Asn Leu Lys Ile Leu Ser Ser Ile Val Glu Pro Val Val Glu
            100                 105                 110

Ser Gly Phe Glu Gly Ile Phe Leu Val Val Ala Asn Pro Val Asp Ile
        115                 120                 125

Leu Thr His Ala Thr Trp Arg Met Ser Gly Phe Pro Lys Asp Arg Val
130                 135                 140

Ile Gly Ser Gly Thr Ser Leu Asp Thr Gly Arg Leu Gln Lys Val Ile
145                 150                 155                 160

Gly Lys Met Glu Asn Val Asp Pro Ser Ser Val Asn Ala Tyr Met Leu
                165                 170                 175

Gly Glu His Gly Asp Thr Glu Phe Pro Ala Trp Ser Tyr Asn Asn Val
            180                 185                 190

Ala Gly Val Lys Val Ala Asp Trp Val Lys Ala His Asn Met Pro Glu
        195                 200                 205
```

```
Ser Lys Leu Glu Asp Ile His Gln Glu Val Lys Asp Met Ala Tyr Asp
    210                 215                 220

Ile Ile Asn Lys Lys Gly Ala Thr Phe Tyr Gly Ile Gly Thr Ala Ser
225                 230                 235                 240

Ala Met Ile Ala Lys Ala Ile Leu Asn Asp Glu His Arg Val Leu Pro
                245                 250                 255

Leu Ser Val Pro Met Asp Gly Glu Tyr Gly Leu His Asp Leu His Ile
            260                 265                 270

Gly Thr Pro Ala Val Val Gly Arg Lys Gly Leu Glu Gln Val Ile Glu
        275                 280                 285

Met Pro Leu Ser Asp Lys Glu Gln Glu Leu Met Thr Ala Ser Ala Asp
    290                 295                 300

Gln Leu Lys Lys Val Met Asp Lys Ala Phe Lys Glu Thr Gly Val Lys
305                 310                 315                 320

Val Arg Gln

<210> SEQ ID NO 97
<211> LENGTH: 1728
<212> TYPE: DNA
<213> ORGANISM: Issatchenkia orientalis

<400> SEQUENCE: 97
atgactgaca aaatctccct aggtacttat ctgtttgaaa agttaaagga agcaggctct      60
tattccatct ttggtgttcc tggtgatttc aatttggcat tgttggacca cgtcaaggaa     120
gttgaaggca ttagatgggt cggtaacgct aacgagttga atgccggcta cgaagctgat     180
ggttatgcaa gaatcaatgg atttgcatcc ctaatcacca cctttggtgt cggtgaattg     240
tctgccgtca atgccattgc aggttcttat gctgaacacg tcccattgat ccatattgtt     300
ggtatgcctt cctcgtctgc tatgaagaac aacttgttgt acaccatacc cttgggtgac     360
acaagattcg acaacttcac cgaaatgtca agaaaaatca gtgcaaaggt tgaaattgtt     420
tacgatttgg aatcagctcc aaaattaatt aataacttga ttgaaaccgc ttatcacaca     480
aagagaccag tctacttggg acttccttcc aactttgctg atgaattggt tccagcggca     540
ttagttaagg aaaacaagtt acatttagaa gaacctctaa acaacccgt tgctgaagaa       600 gaattcattc ataacgttgt tgaaatggtc aagaaggcag aaaaaccaat cattctcgtt     660
gacgcttgtg ctgcaagaca taacattct aaggaagtga gagagttggc taaattgact     720 aaaattccctg tcttcaccac cccaatgggt aaatctactg ttgatgaaga tgatgaagaa     780
ttctttggct atacttggg ttctctatct gctccagatg ttaaggacat tgttggccca     840
accgattgta tcttatcctt aggtggttta ccttctgatt tcaacaccgg ttccttctca     900
tatggttaca ccactaagaa tgtcgttgaa ttccattcca actactgtaa attcaaatct     960
gcaacttatg aaaacttgat gatgaagggc gcagtccaaa gattgatcag cgaattgaag    1020
aatattaagt attccaatgt ctcaacttta tctccaccaa atctaaatt tgcttacgaa     1080 tctgcaaagg ttgctccaga aggtatcatc actcaagatt acctgtggaa gagattatct    1140
tacttcttaa agccaagaga tatcattgtc actgaaactg gtacttcctc ctttggtgtc    1200
ttggctaccc acttaccaag agattcaaag tctatctccc aagtcttatg ggttccatt     1260 ggtttctcct accagctgc agttggtgct gcatttgctg ctgaagatgc acacaaacaa     1320
actggcgaac aagaaagaag aactgttttg tttattggtg atggttcttt acaattgact     1380
gtccaatcaa tctcagatgc tgcaagatgg aacatcaagc catacatctt catcttaaac    1440
```

```
aacagaggtt acactatcga aaagttgatc cacggtcgtc atgaggacta caaccaaatt    1500
caaccatggg atcaccaatt gttattgaag ctctttgctg acaagaccca atatgaaaac    1560
catgttgtta aatccgctaa ggacttggac gctttgatga aggatgaagc attcaacaag    1620
gaagataaga ttagagtcat tgaattattc ttggatgaat tcgatgctcc agaaatcttg    1680
gttgctcaag ctaaattatc tgatgaaatc aactctaaag ccgcttaa                 1728
```

GENETICALLY MODIFIED YEAST OF THE SPECIES *ISSATCHENKIA ORIENTALIS* AND CLOSELY RELATES SPECIES, AND FERMENTATION PROCESSES USING SAME

This invention was made under contract no. DE-FC07-021D14349 with the United States Department of Energy. The United States Government has certain rights to this invention.

This application claims benefit of U.S. Provisional Patent Application 60/686,899, filed Jun. 2, 2005.

This invention relates to certain genetically modified yeast species.

Certain organic acids such as lactic acid are manufactured through an industrial fermentation process. The fermentation is conducted using various types of bacterial species, which consume sugars (principally glucose) and convert those sugars to the desired acid.

There are several reasons why it would be desirable to develop a yeast or fungal biocatalyst for producing organic acids from sugar substrates. Many bacteria are unable to synthesize some of the amino acids or proteins they need to grow and metabolize sugars efficiently. As a result, bacteria often must be fed a somewhat complex package of nutrients. This increases the direct expense required to operate the fermentation. The increased complexity of the broth makes it more difficult to recover the fermentation product in reasonably pure form, so increased operating and capital costs are incurred to recover the product. On the other hand, many yeast species can synthesize their needed amino acids or proteins from inorganic nitrogen compounds. They often grow and ferment well in so-called "defined" media, which are simplified, often less expensive and present fewer difficulties in product recovery operations.

Another reason that yeast are of interest as a biocatalyst for organic acid production has to do with the nature of the product itself. To have an economically viable process, a high concentration of the organic acid product must accumulate in the fermentation broth. In addition to the normal concerns about toxicity (the fermentation product may be toxic to the biocatalyst when present in high concentrations), an additional concern about acidity exists when the fermentation product is an acid. The media will become increasingly acidic as more of the organic acid is produced. Most bacteria that produce these organic acids do not perform well in strongly acidic environments—they either do not survive under those conditions or else produce the product so slowly as to be economically unviable.

For this reason, commercial acid fermentation processes are buffered by the addition of an agent which neutralizes the acid as it formed. This maintains the broth at or near a neutral pH and allows the bacteria to grow and produce efficiently. However, this converts the acid to a salt, which subsequently must be split to obtain the product in its desired acid form.

The most common buffering agent is a calcium compound, which neutralizes the organic acid to form the corresponding calcium salt. After the calcium salt is recovered from the fermentation broth, it is split by the addition of a mineral acid, typically sulphuric acid, to regenerate the organic acid and form an insoluble calcium salt of the mineral acid. This process therefore involves direct expense for the buffering agent and mineral acid, as well as costs for handling and disposing the unwanted calcium salt by-product. These costs could be reduced or eliminated if the biocatalyst could grow and produce efficiently under lower pH conditions.

Yeast species have been considered as candidates for such low pH fermentations. Many yeast species naturally ferment hexose sugars to ethanol, but few if any naturally produce desired organic acids such as lactic acid. Efforts have been made to genetically modify various yeast species to insert one or more genes that will enable the cell to produce lactic acid. In order to divert sugar metabolism from ethanol production to lactic acid production, these cells have also been genetically modified to disrupt or delete the native pyruvate decarboxylase (PDC) gene. This work is described, for example, in WO 99/14335, WO 00/71738 A1, WO 02/42471 A2, WO 03/049525 A2, WO 03/102152 A2 and WO 03/102201A2. Much of the efforts described in these various publications center on *Kluyveromyces* species, such as *K. marxianus*, and certain species classified under the genus *Candida*, such as *C. sonorensis* and *C. methanosorbosa*.

There remains a desire to provide even better biocatalysts for organic acid fermentation processes. A biocatalyst for these fermentation processes desirably can achieve high volumetric and specific productivities; a high yield of the desired organic acid from the fermentation substrate; the ability to grow and produce with reasonable efficiency under acidic conditions; and the ability to grow and produce with reasonable efficiency under microaerobic and especially anaerobic conditions. The biocatalyst preferably can achieve these results using a simplified defined media.

In one aspect, this invention is a genetically modified yeast cell of a species within the *Issatchenkia orientalis/Pichia fermentans* clade having at least one exogenous lactate dehydrogenase gene integrated into its genome.

This invention is also a fermentation process in which a genetically modified yeast cell of the first aspect is cultured under fermentation conditions in a fermentation broth that includes a fermentable sugar to produce lactic acid or a salt thereof.

This invention is in addition a fermentation process in which a genetically modified yeast cell of the first aspect is cultured under fermentation conditions in a fermentation broth that includes a fermentable sugar to produce lactic acid or a salt thereof, wherein the pH of the fermentation broth during at least a portion of the period of fermentation is in the range of from about 1.5 to about 4.5.

It has surprisingly been found that modified cells of the invention exhibit an excellent tolerance to moderately low pH, high lactic acid titer conditions, and can grow and produce lactic acid at good rates in an unbuffered medium, even under anaerobic or quasi-anaerobic conditions. In addition, the modified cells grow well on defined media.

Figure 2:
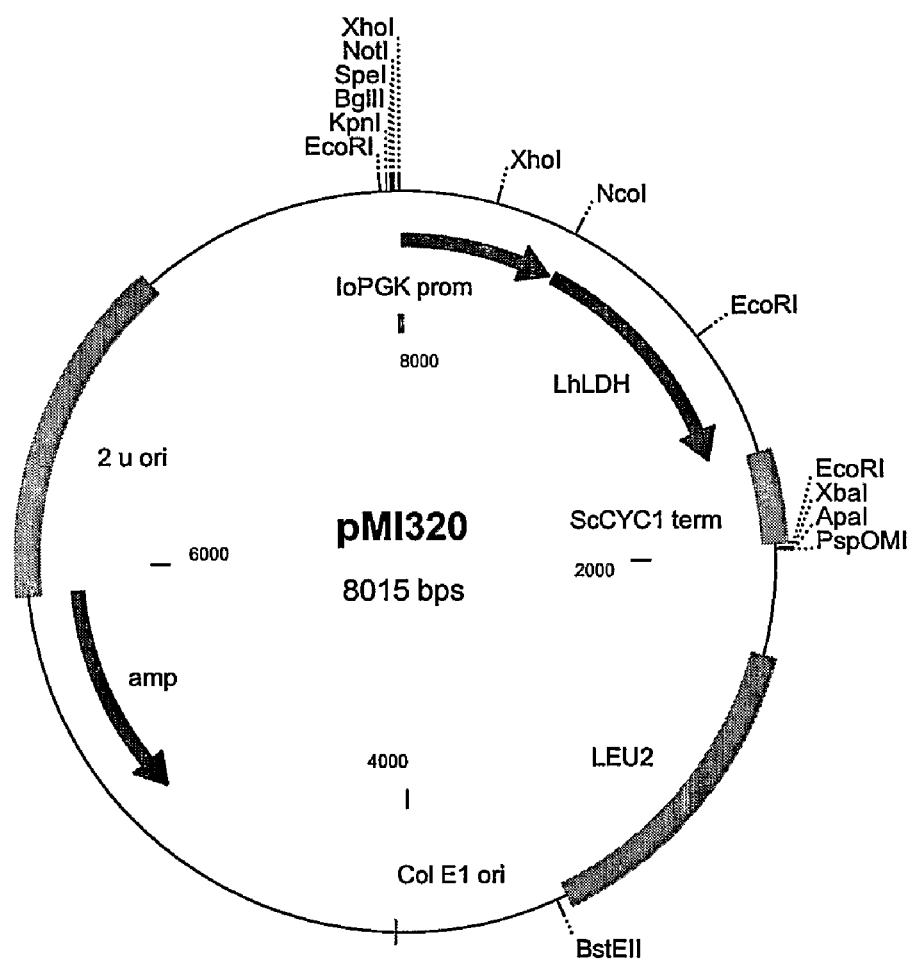
Figure 3:
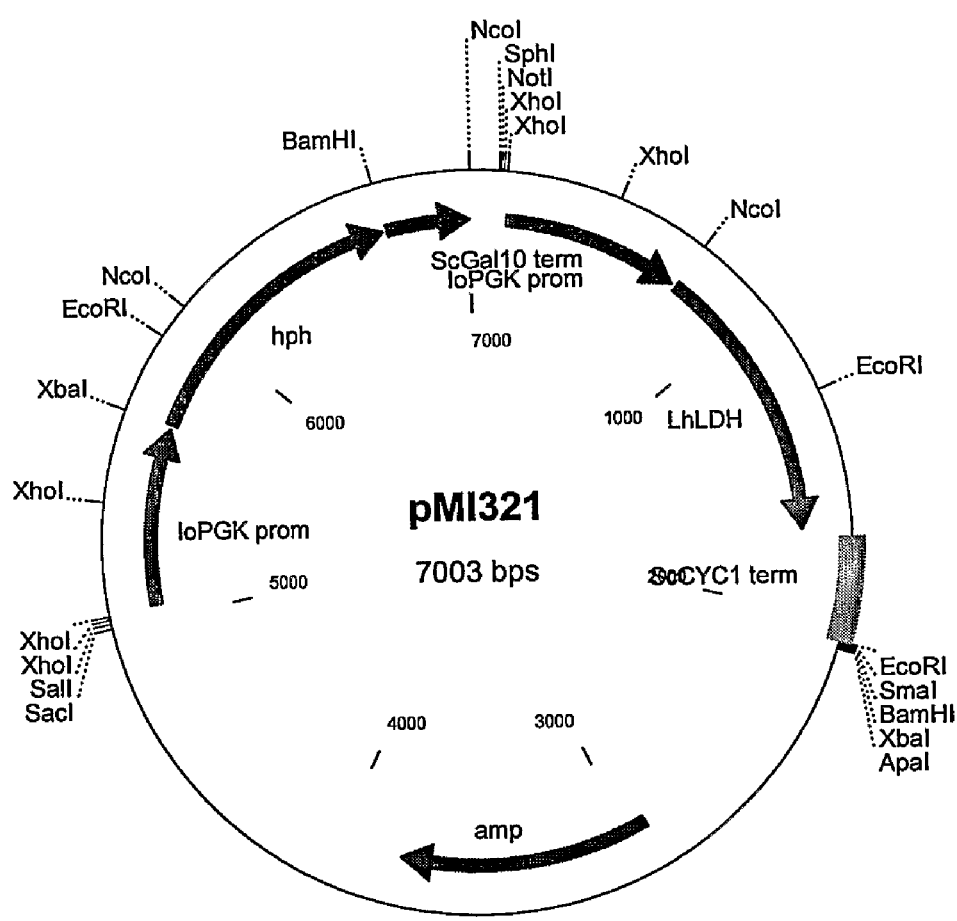
Figure 4:
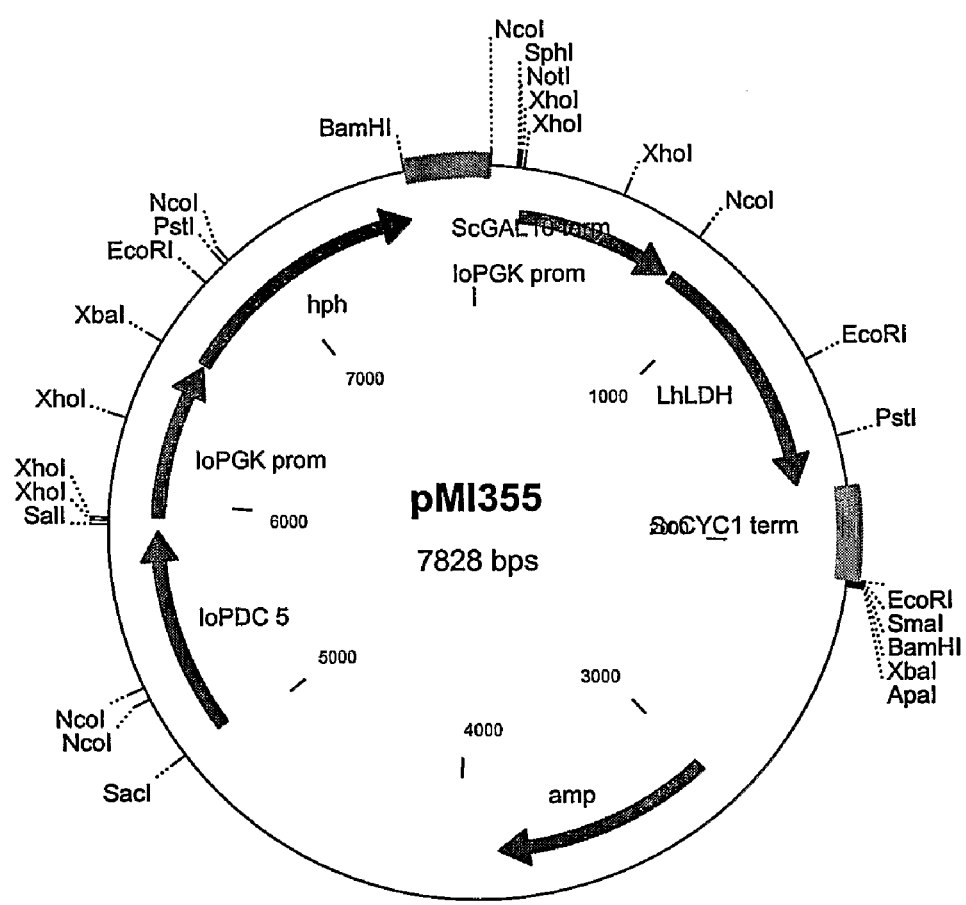
Figure 5:
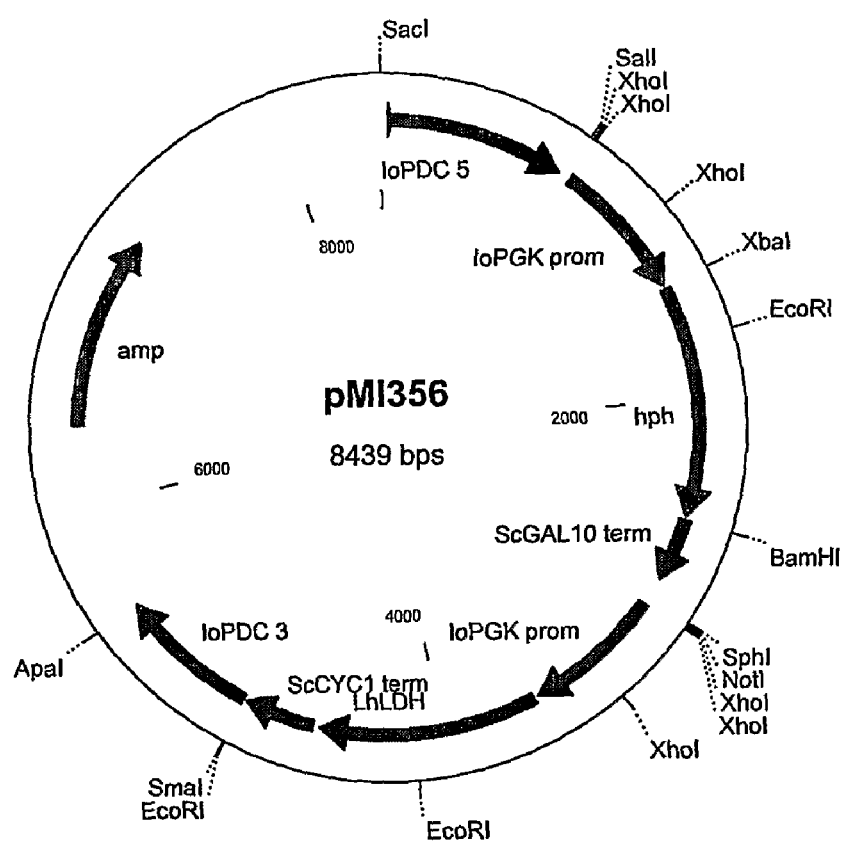
Figure 6:
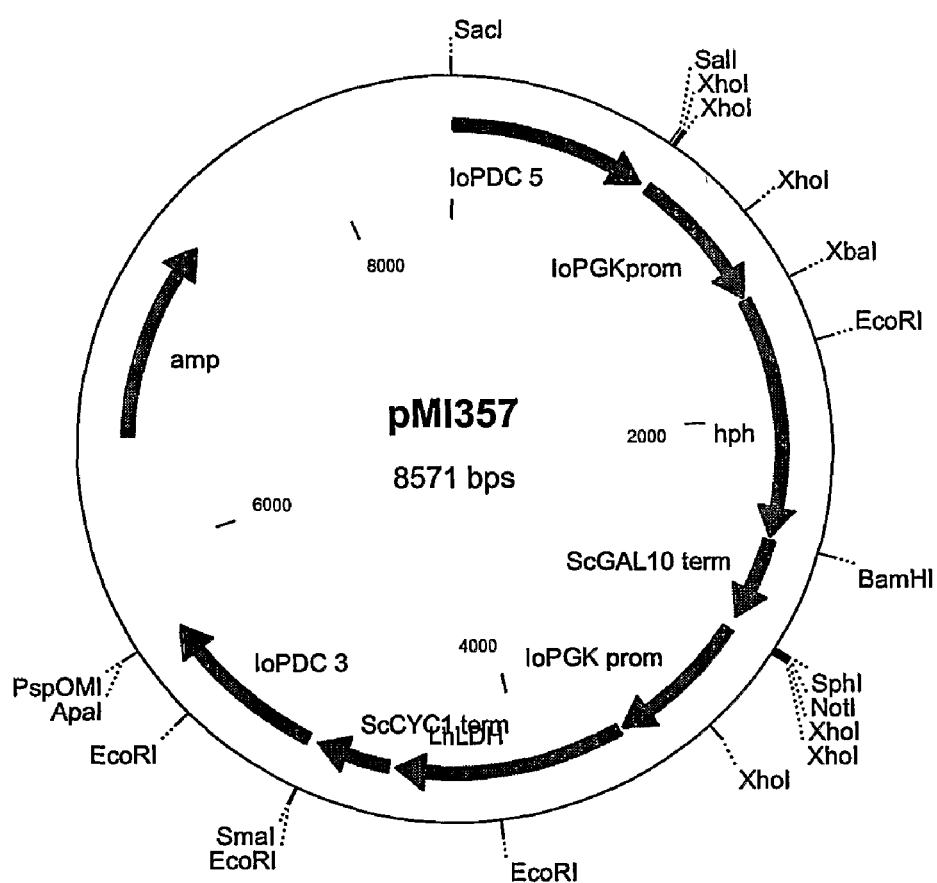
Figure 7:
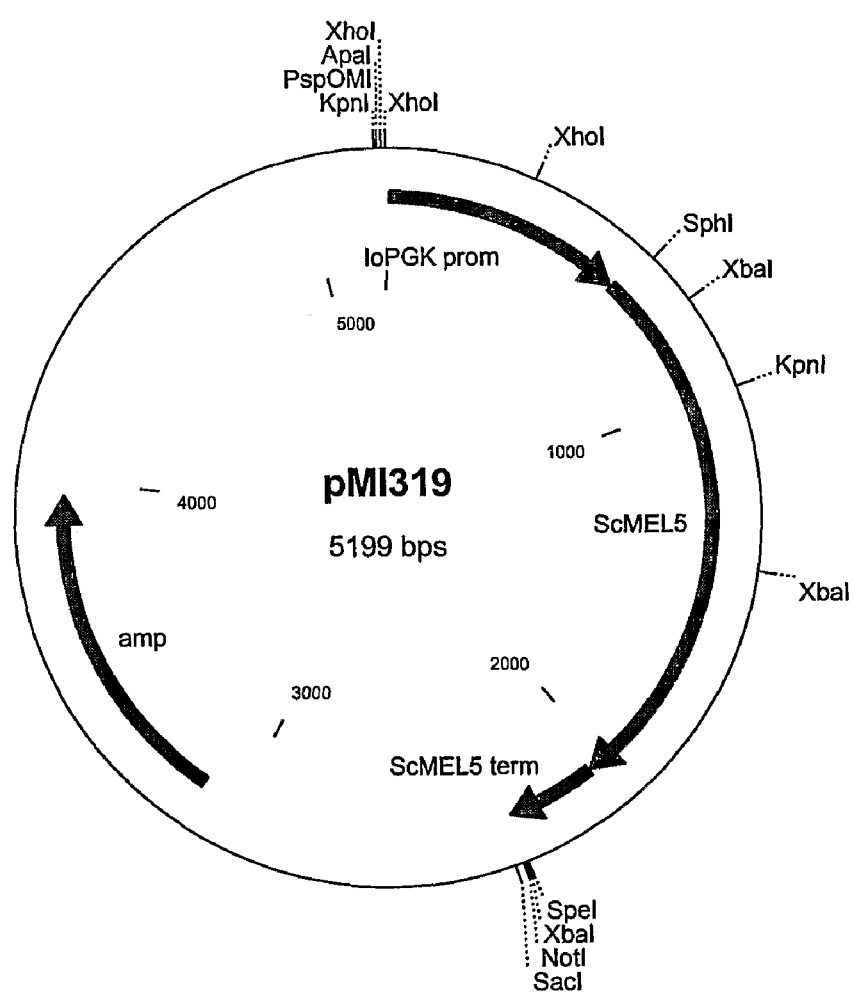
Figure 8:
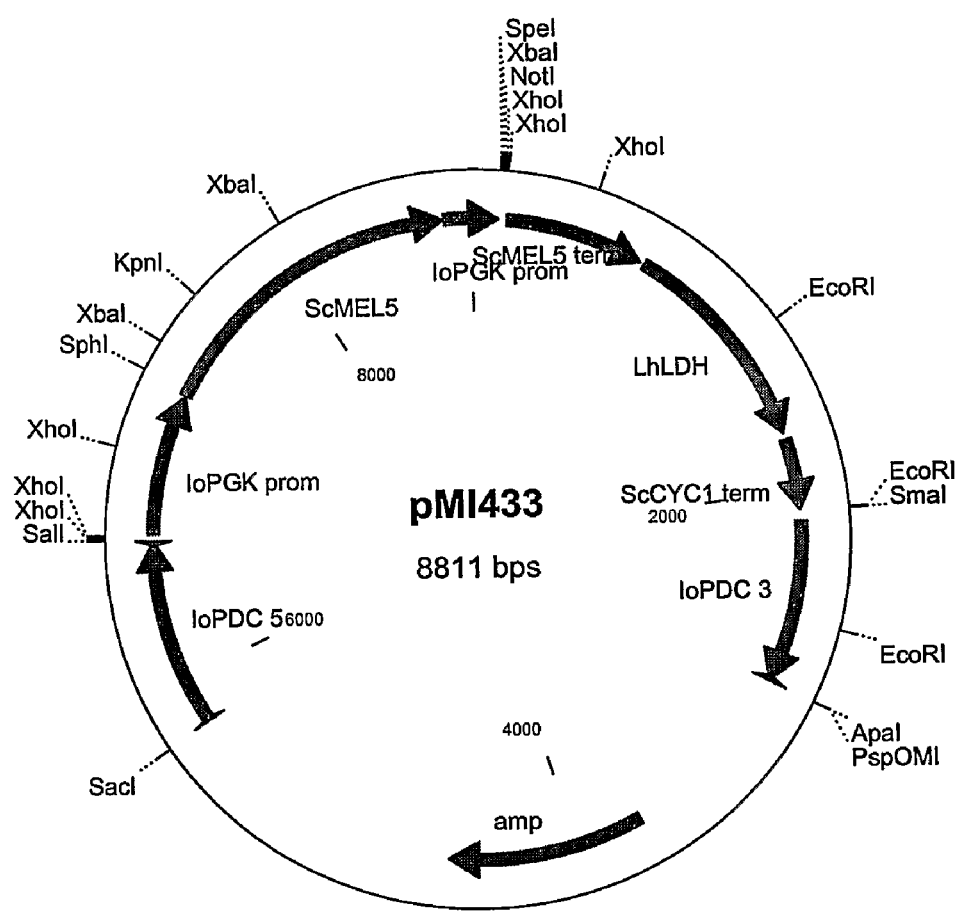
Figure 9:
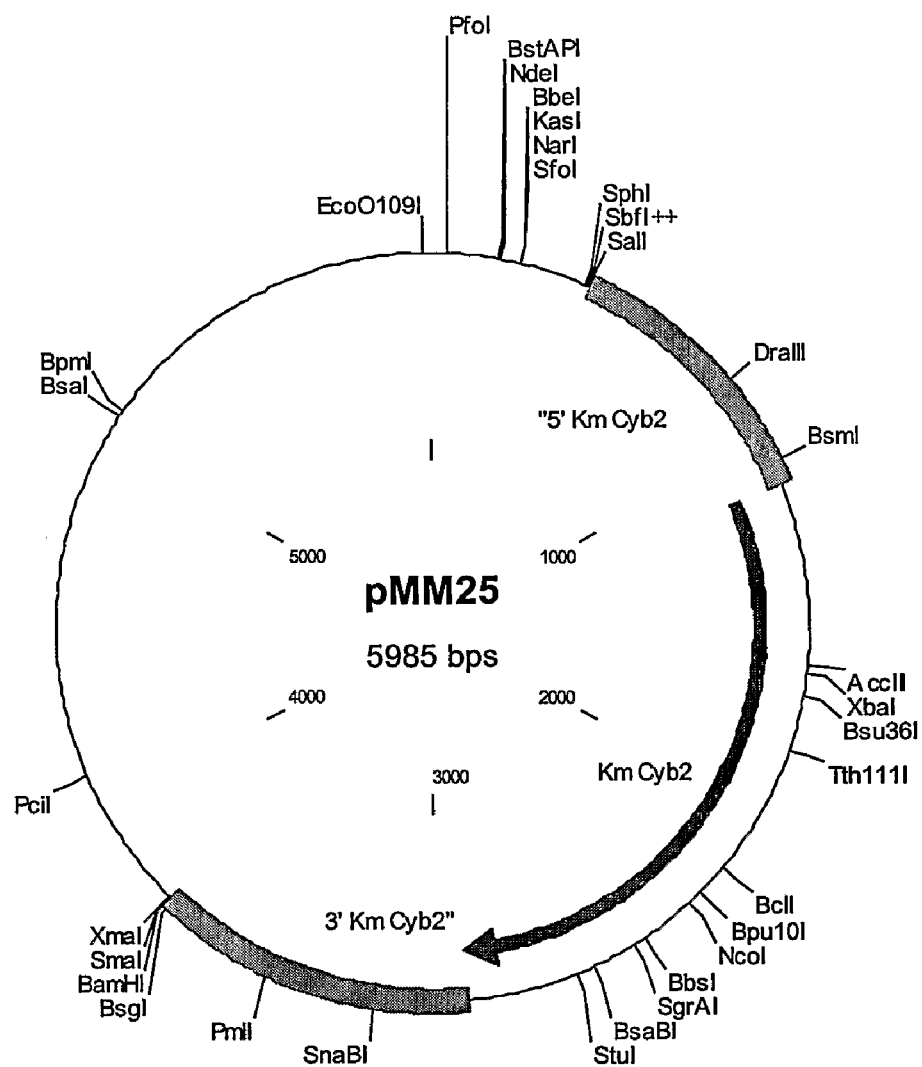
Figure 10:
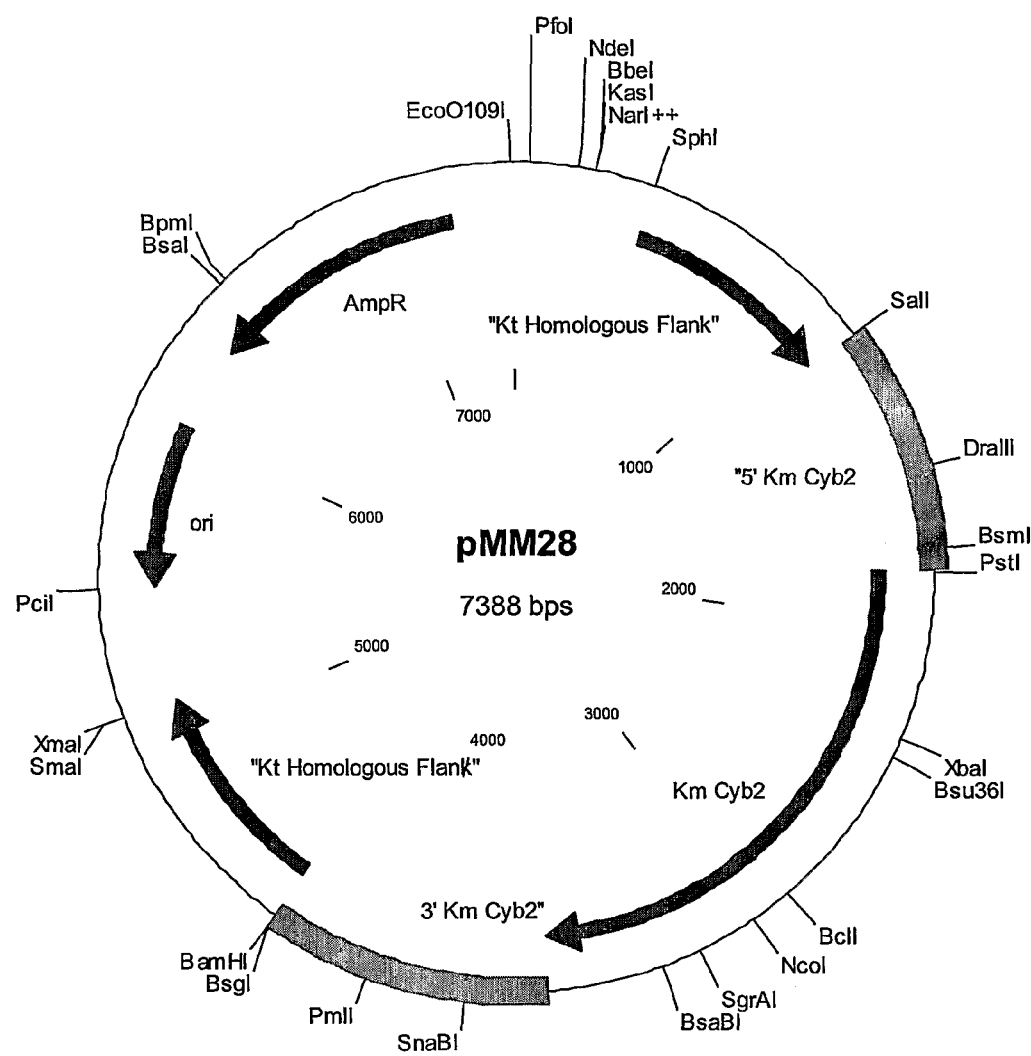
Figure 11:
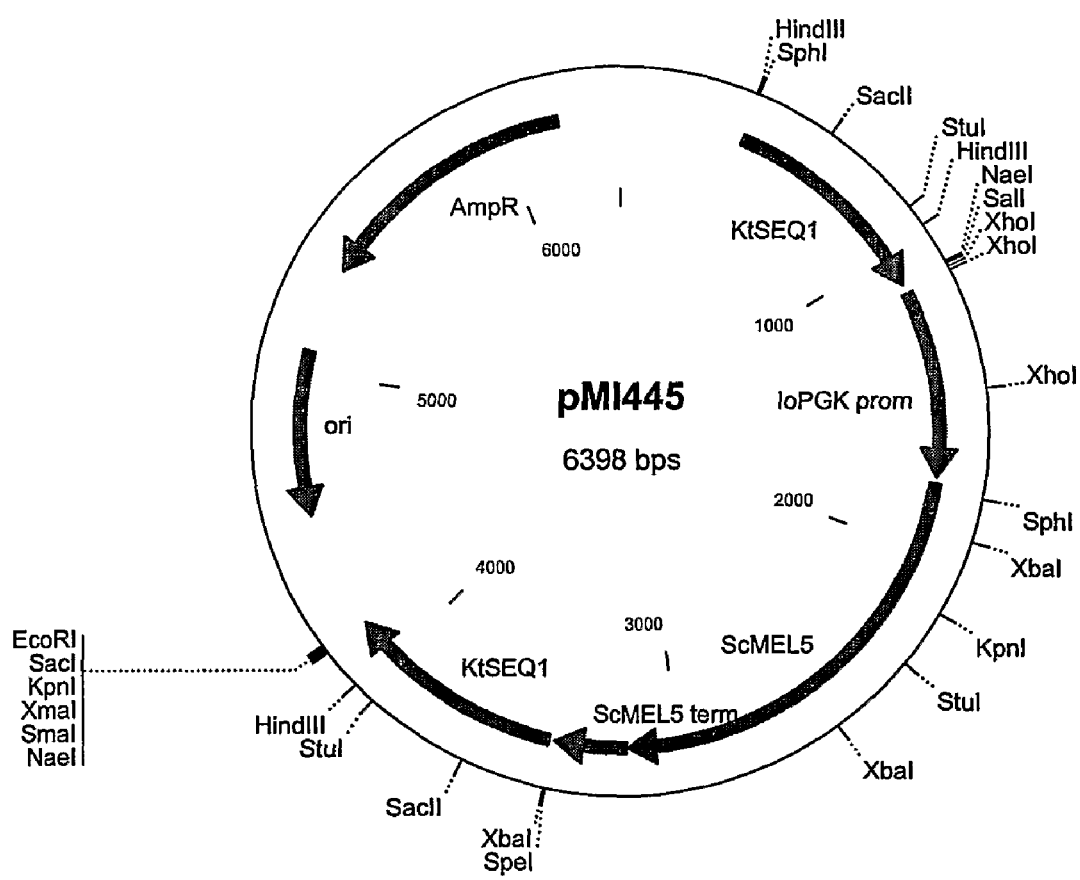
Figure 12:
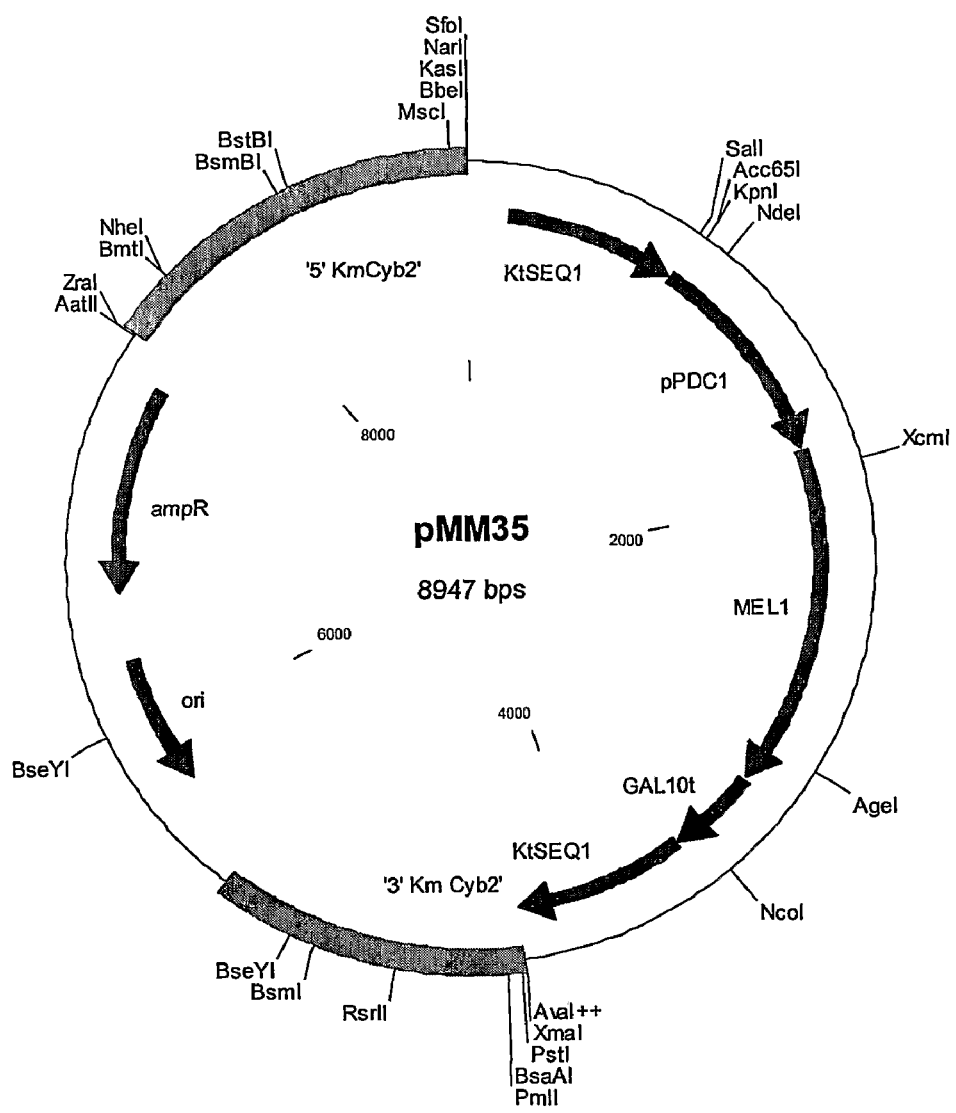
Figure 13:
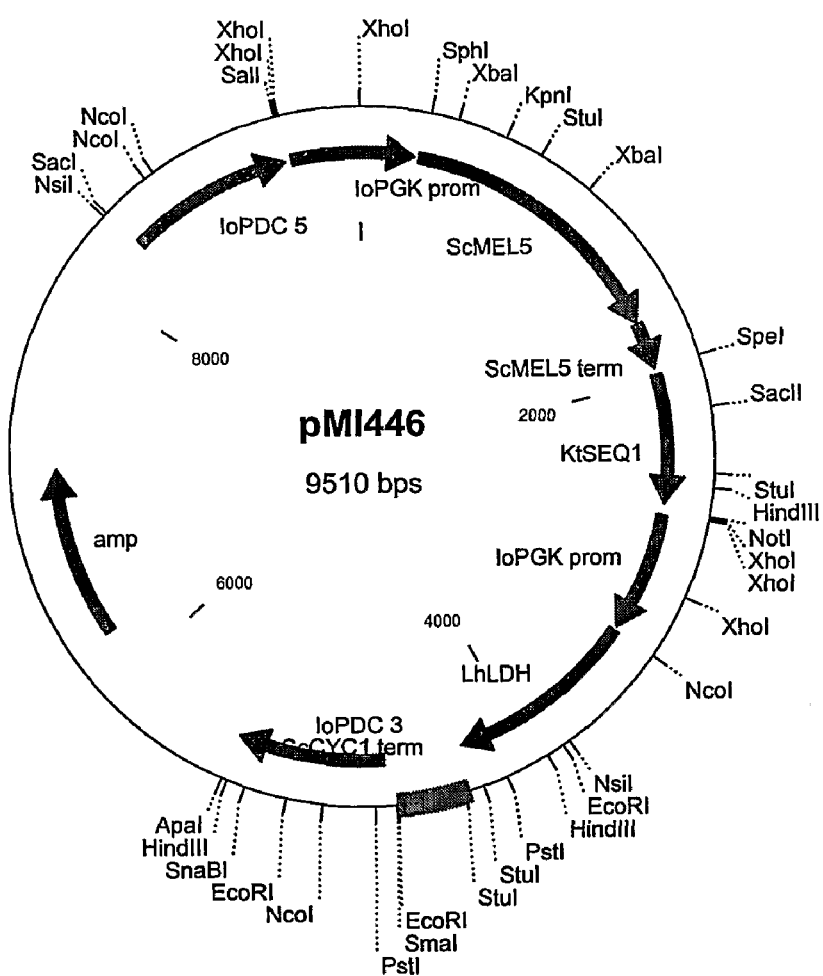
Figure 14:
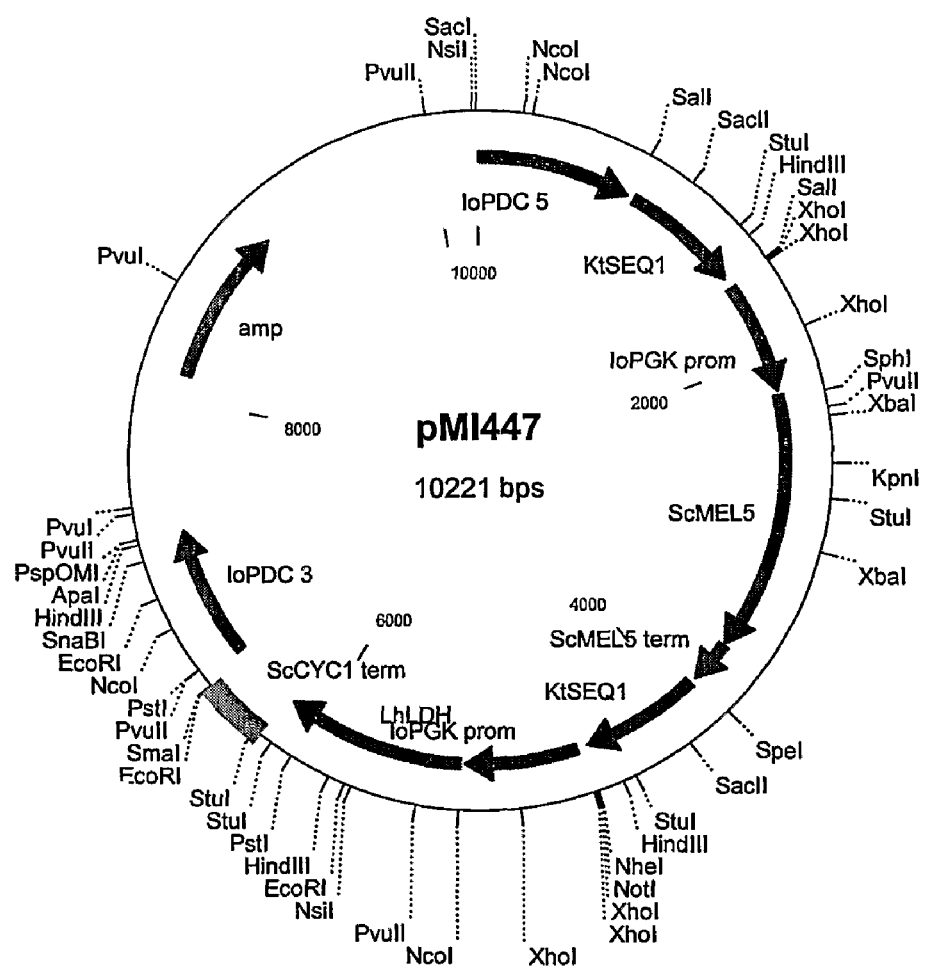
Figure 15:
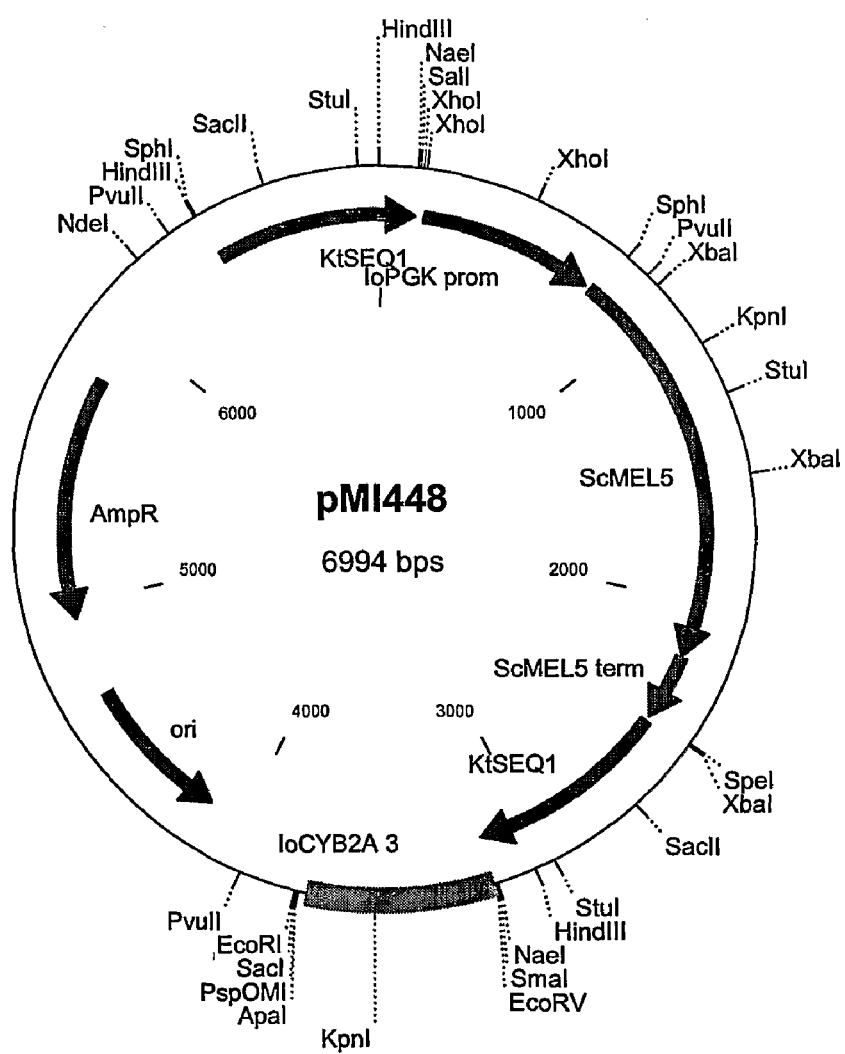
Figure 16:
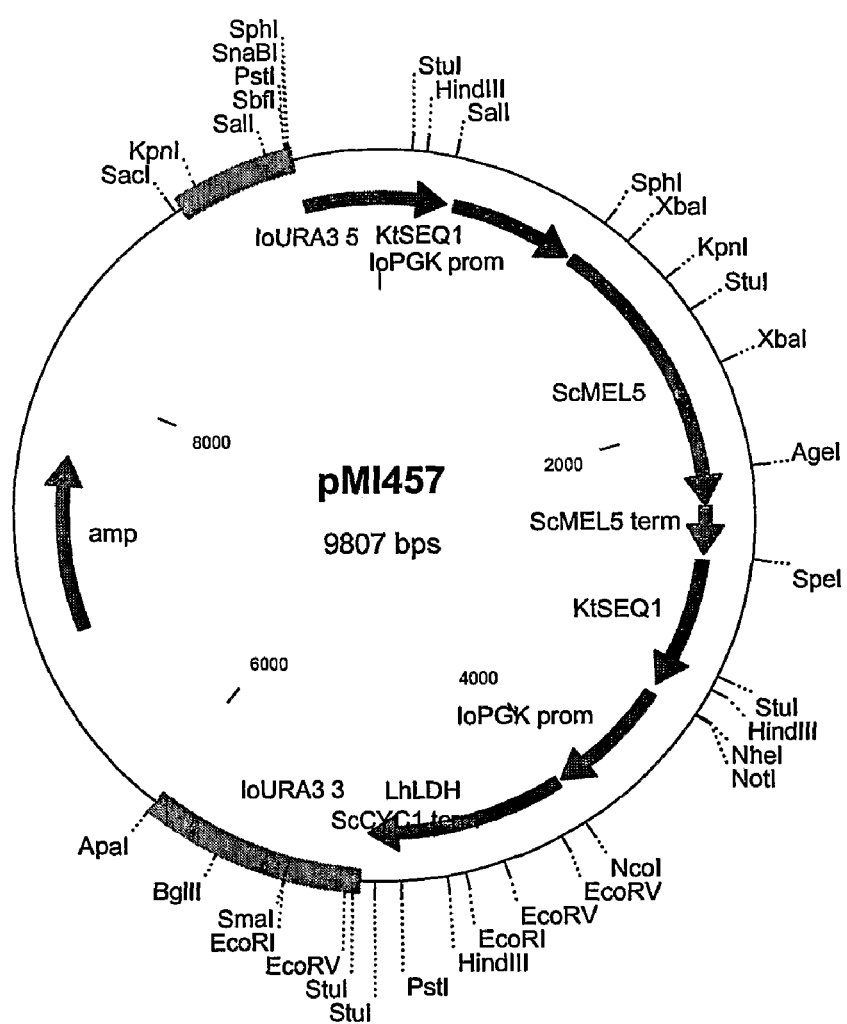
Figure 17:
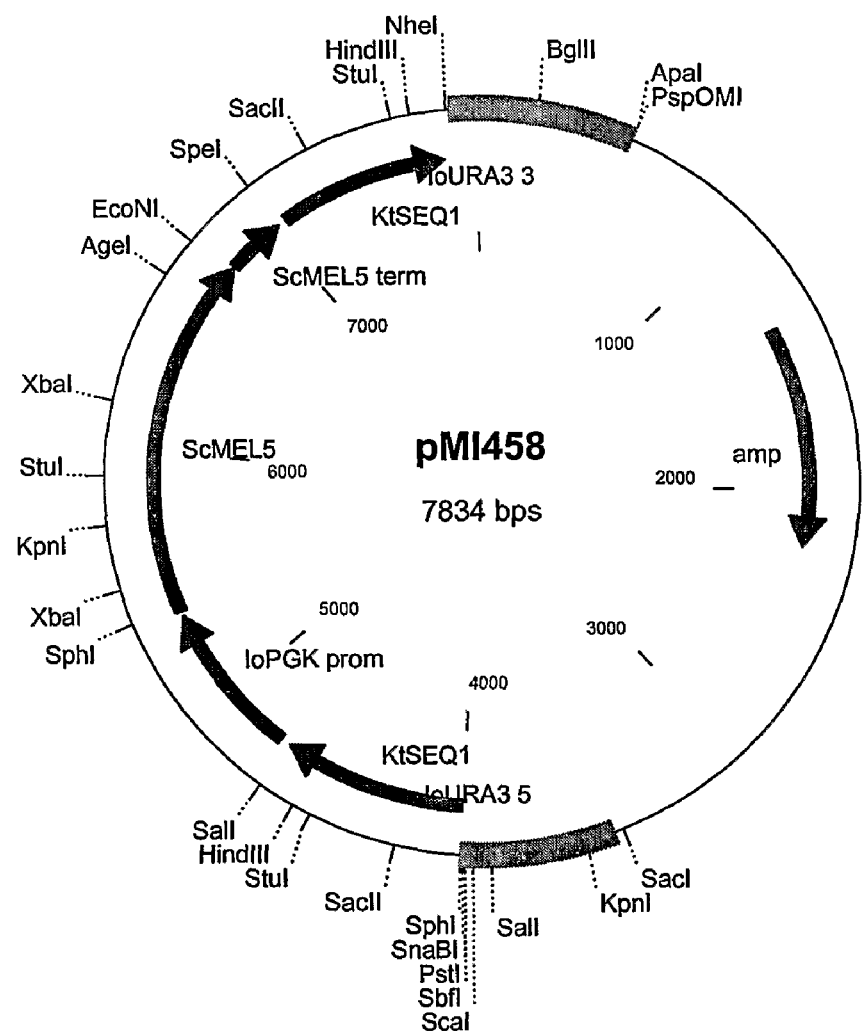
Figure 18:
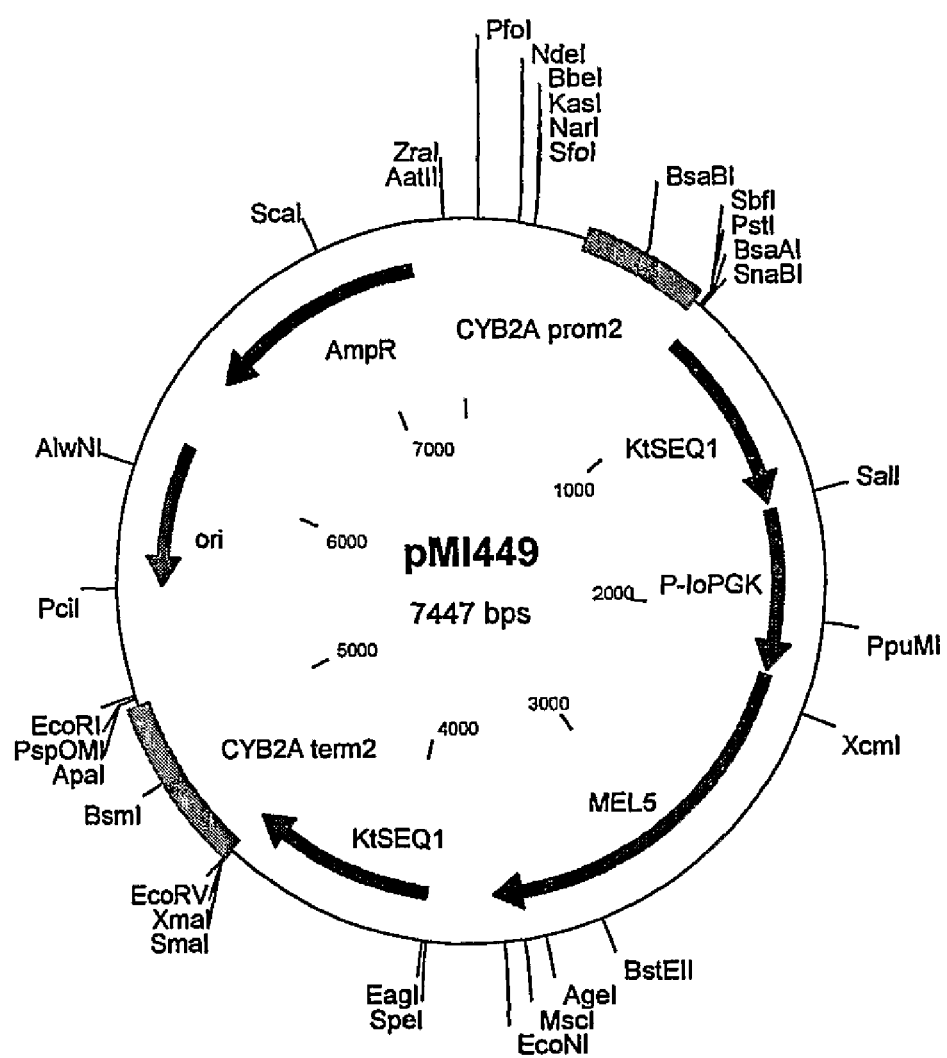
Figure 19:
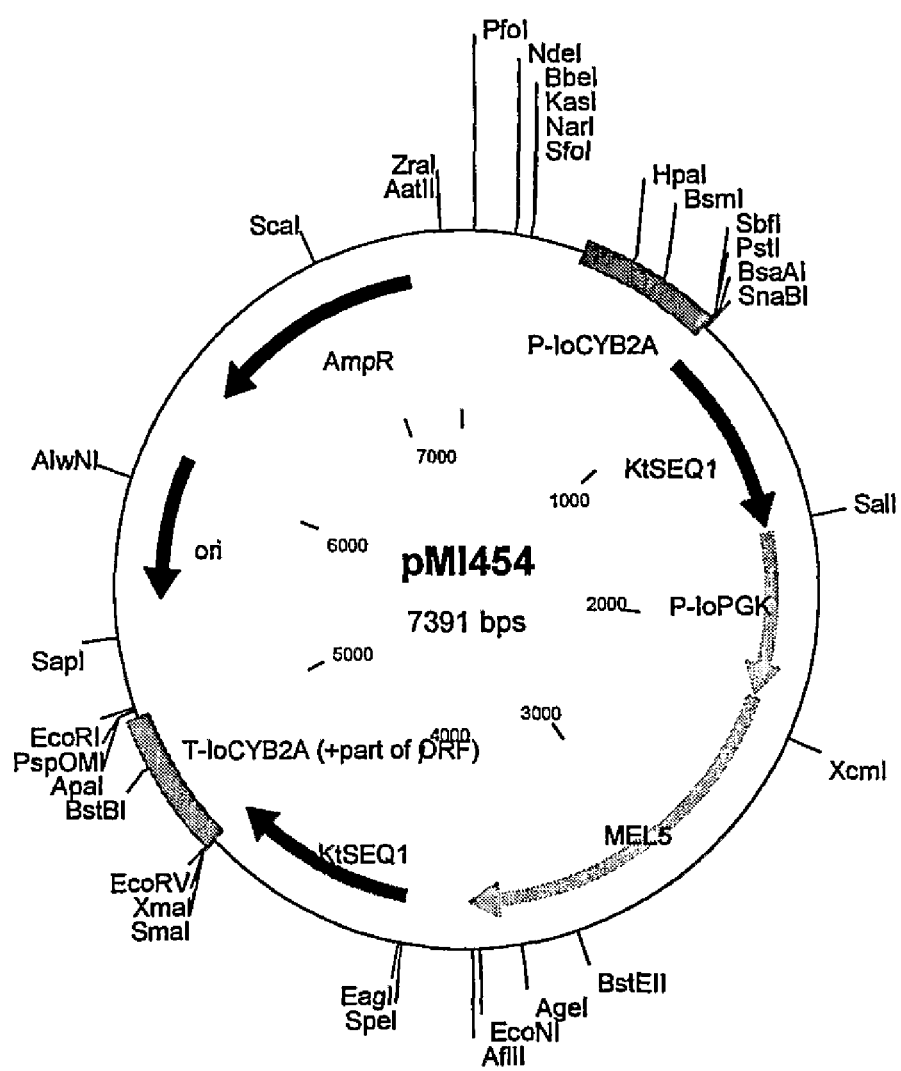
Figure 20:
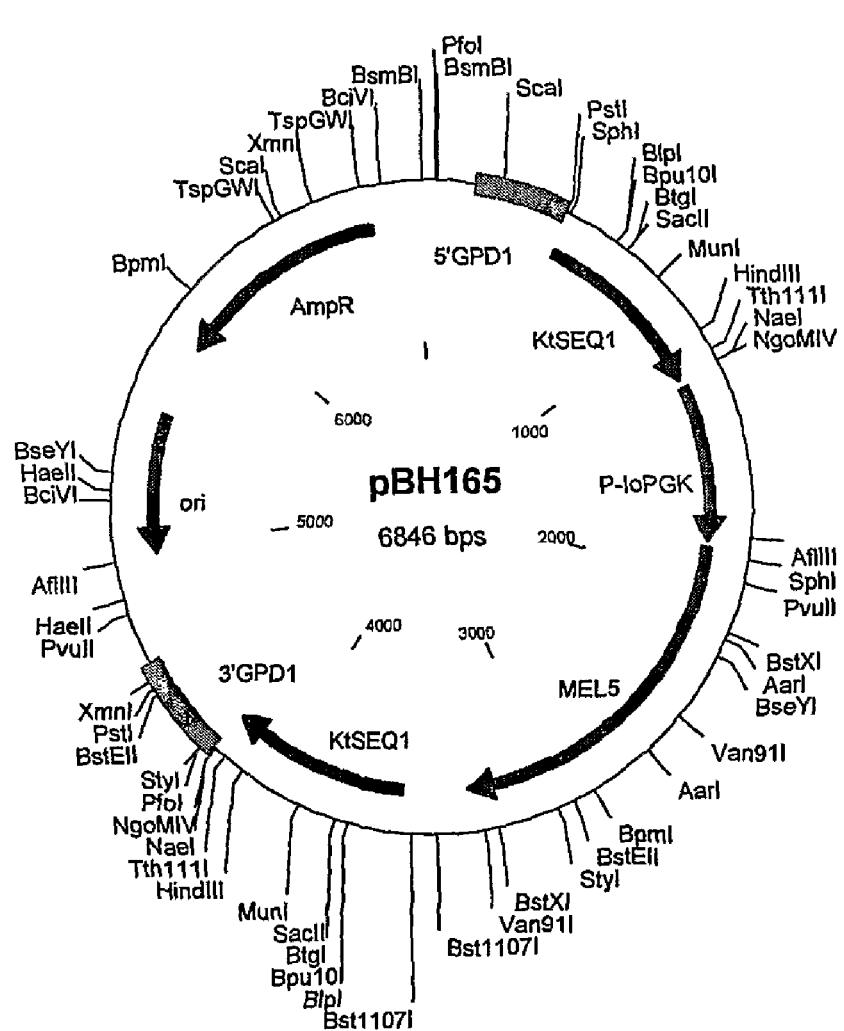
Figure 21:
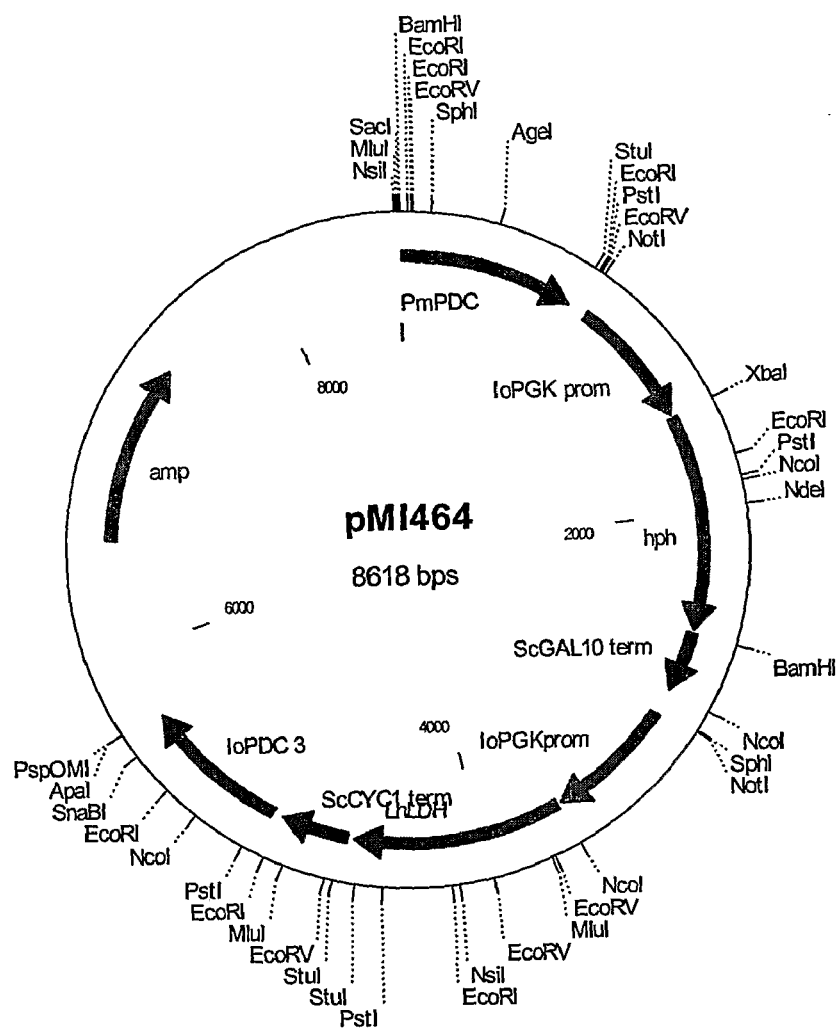

FIG. 1 is a diagram depicting the pMI318 plasmid.
FIG. 2 is a diagram depicting the pMI320 plasmid.
FIG. 3 is a diagram depicting the pMI321 plasmid.
FIG. 4 is a diagram depicting the pMI355 plasmid.
FIG. 5 is a diagram depicting the pMI356 plasmid.
FIG. 6 is a diagram depicting the pMI357 plasmid.
FIG. 7 is a diagram depicting the pMI319 plasmid.
FIG. 8 is a diagram depicting the pMI433 plasmid.
FIG. 9 is a diagram depicting the pMM25 plasmid.
FIG. 10 is a diagram depicting the pMM28 plasmid.
FIG. 11 is a diagram depicting the pMI445 plasmid.
FIG. 12 is a diagram depicting the pMM35 plasmid.
FIG. 13 is a diagram depicting the pMI446 plasmid.
FIG. 14 is a diagram depicting the pMI447 plasmid.
FIG. 15 is a diagram depicting the pMI448 plasmid.
FIG. 16 is a diagram depicting the pMI457 plasmid.
FIG. 17 is a diagram depicting the pMI458 plasmid.
FIG. 18 is a diagram depicting the pMI449 plasmid.
FIG. 19 is a diagram depicting the pMI454 plasmid.
FIG. 20 is a diagram depicting the pBH165 plasmid.
FIG. 21 is a diagram depicting the pMI464 plasmid.

The genetically modified yeast of the invention is made by performing certain genetic modifications to a host yeast cell. The host cell is of a species contained within the *I. orientalis/ P. fermentans* clade. This clade is the most terminal c that contains at least the species *Issatchenkia orientalis, Pichia galeiformis, Pichia* sp. YB-4149 (NRRL designation), *Candida ethanolica, P. deserticola, P. membranifaciens* and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences", *Antonie van Leeuwenhoek* 73:331-371, 1998, incorporated herein by reference. See especially p. 349. Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to that of other members of the clade than to that of yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

When first characterized, the species *I. orientalis* was assigned the name *Pichia kudriavzevii*. The anamorph (asexual form) of *I. orientalis* is known as *Candida krusei*.

A particularly suitable host cell is *I. orientalis* strain ATCC 32196. Another particularly suitable host cell is *I. orientalis* strain ATCC PTA-6658.

The cell of the invention contains at least one functional, exogenous lactate dehydrogenase (LDH) gene integrated into its genome. An LDH gene is any gene that encodes for a lactate dehydrogenase enzyme, i.e., one having lactate dehydrogenase activity. "Lactate dehydrogenase activity" refers to the ability of the protein to catalyze the reaction of pyruvate to lactate. Lactate dehydrogenase enzymes include (but are not limited to) those categorized by the Enzyme Commission numbers 1.1.1.27 and 1.1.1.28.

In this context, "exogenous" means that the genetic material under consideration (in this case, the LDH gene) is not native to the host strain. The term "native" is used herein with respect to genetic materials (e.g., a gene, promoter or terminator) that are found (apart from individual-to-individual mutations which do not affect function) within the genome of wild-type cells of the host cell.

The LDH gene may enable the modified cell to produce either the L- or D-lactic acid stereoisomer. It is possible that the modified cell of the invention contains both L- and D-LDH genes, and thus is capable of producing both lactic acid stereoisomers. However, it is preferred that only L- or only D-LDH genes are present, so the cell produces a more optically pure lactic acid product.

Suitable LDH genes include those obtained from bacterial, fungal, yeast or mammalian sources. Examples of specific L-LDH genes are those obtained from *Lactobacillus helveticus, L. casei, Bacillus megaterium, Pediococcus acidilactici, Rhizopus oryzae* and bovine sources such as *Bos taurus*. Examples of specific D-LDH genes are those obtained from *L. helveticus, L. johnsonii, L. bulgaricus, L. delbrueckii, L. plantarum, L. pentosus* and *P. acidilactici*. Functional genes that are identical to such L-LDH or D-LDH genes or which have an identities score of at least 35%, 60%, 70% or 80% relative to such genes at the amino acid level are suitable. The native genes obtained from any of these sources may be subjected to mutagenesis if necessary to provide a coding sequence starting with the usual eukaryotic starting codon (ATG), or for other purposes. A preferred L-LDH gene is that obtained from *L. helveticus* or one that has an identities score relative to such gene of at least 35%, 60%, 70%, 80%, 85%, 90% or 95%. Another preferred L-LDH gene is that obtained from *B. megaterium* or one that has an identities score of at least 35%, 60%, 70%, 80%, 85%, 90% or 95% compared with such gene. Another preferred L-LDH gene is that obtained from *Bos. taurus* or one that has an identities score of at least 35%, 60%, 70%, 80%, 85%, 90% or 95% compared with such gene. A preferred D-LDH gene is that obtained from *L. helveticus* or one that has an identities score of at least 45%, 60%, 70%, 80%, 85%, 90% or 95% compared with such gene.

Identities scores of amino acid sequences of DNA, RNA or proteins are, for purposes of this invention computed using BLAST version 2.2.1 software with default parameters.

Particularly suitable LDH genes include those that encode for an enzyme with an amino acid sequence that has an identities score of at least 60%, especially at least 80%, 85% or 95%, compared with the sequence identified as SEQ. ID. NO. 93 (which appears as SEQ. ID. NO. 45 in WO 03/049525) or compared with that identified as SEQ. ID. NO. 94 (which appears as SEQ. ID. NO. 49 in WO 03/049525). Particularly suitable LDH genes also include those that encode an enzyme having a protein sequence that has an identities score of at least 60%, 80%, 85% or 95% compared to SEQ. ID. NO. 95 or SEQ. ID. NO. 96 (which appear as SEQ ID. NO. 46 and 50, respectively, in WO 03/049525).

The transformed cell may contain a single LDH gene or multiple LDH genes, such as from 1-10 LDH genes, especially from 1-5 LDH genes. When the transformed cell contains multiple LDH genes, the individual genes may be copies of the same gene, or include copies of two or more different LDH genes. Multiple copies of the exogenous LDH gene may be integrated at a single locus (so they are adjacent to each other), or at several loci within the host cell's genome.

The exogenous LDH gene is under the transcriptional control of one or more promoters and one or more terminators, both of which are functional in the modified yeast cell. As used herein, the term "promoter" refers to an untranslated sequence located upstream (i.e., 5') to the translation start codon of a structural gene (generally within about 1 to 1000 bp, preferably 1-500 bp, especially 1-100 bp) and which controls the start of transcription of the structural gene. Similarly, the term "terminator" refers to an untranslated sequence located downstream (i.e., 3') to the translation finish codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene is such that the promoter or terminator, as the case may be, performs its transcriptional control function.

Promoters and terminator sequences may be native to *I. orientalis* or exogenous to the cell. Useful promoter and terminator sequences include those that are highly identical (i.e., have an identities score of 90% or more, especially 95% or more, most preferably 99% or more) in their functional portions compared to the functional portions of promoter and terminator sequences, respectively, that are native to the host cell, particularly when the insertion of the exogenous gene is targeted at a specific site in the cell's genome.

One suitable type of promoter has an identities score at least 90%, 95% or 99% relative to a promoter that is native to a yeast gene. A more suitable type of promoter has an identities score of at least 90%, 95% or 99% compared to a promoter for a gene that is native to the host cell. Particularly useful promoters include promoters for yeast pyruvate decarboxylase (PDC), phosphoglycerate kinase (PGK), and transcription elongation factor-1 (TEF-1) genes, especially from the respective *I. orientalis* genes. An especially useful promoter includes the functional portion of a promoter for an *I. orientalis* PGK gene.

One suitable type of terminator has an identities score of at least 90%, 95% or 99% compared to a terminator for a gene that is native to a yeast. The terminator may have an identities score at least 90%, 95% or 99% homologous to a terminator for a gene that is native to the host cell. Particularly useful terminators include terminators for yeast pyruvate decarboxylase (PDC), xylose reductase, (XR), xylitol dehydrogenase (XDH) or iso-2-cytochrome c (CYC) genes, or a terminator from the galactose family of genes in yeast, particularly the so-called GAL10 terminator. An especially preferred terminator includes a functional portion of a terminator for a PDC gene of the host cell.

The use of native (to the host cell) promoters and terminators, together with their respective upstream and downstream flanking regions, can permit the targeted integration of the LDH gene into specific loci of the host cell's genome, and for simultaneous integration the LDH gene and deletion of another native gene, such as, for example, a PDC gene.

It is possible for different exogenous LDH genes to be under the control of different types of promoters and/or terminators.

The exogenous LDH gene may be integrated randomly into the host cell's genome or inserted at one or more targeted locations. Examples of targeted locations include the loci of a gene that is desirably deleted or disrupted, such as a PDC gene. Integration at the PDC locus may be accomplished with or without deletion or disruption of the native PDC gene, but it is generally preferred to disrupt or delete the PDC gene, so the modified cell produces less ethanol.

The host cell may contain multiple PDC genes. Native *I. orientalis* cells, for example, contain two PDC genes, which are designated herein as IoPDC1A and IoPDC1B. In some strains, including ATCC PTA-6658, these are visualized as ~8 kbp and ~10 kbp HindIII bands, respectively, upon Southern analysis of the wild-type organism. Other *I. orientalis* strains, such as ATCC 32196, appear to have two alleles that produce bands of similar size. When the host cell contains multiple PDC genes, it is preferred to delete or disrupt at least one of them and more preferred to disrupt all of them, as this destroys the cell's ability to produce ethanol. Thus, in *I. orientalis*, it is preferred to disrupt the IoPDC1A or IoPDC1B genes and more preferred to delete or disrupt both the IoPDC1A and IoPDC1B genes.

By "delete or disrupt", it is meant that the entire coding region of the gene is eliminated (deletion), or the gene or its promoter and/or terminator region is modified (such as by deletion, insertion, or mutation) so that the gene no longer produces an active enzyme, or produces an enzyme with severely reduced activity. The deletion or disruption can be accomplished by genetic engineering methods, forced evolution or mutagenesis and/or selection or screening. A preferred way of accomplishing this is to replace the PDC gene with a cassette containing an LDH gene, as described more fully below.

Genetic modification of the host cell is accomplished in one or more steps via the design and construction of appropriate vectors and transformation of the host cell with those vectors. Electroporation and/or chemical (such as calcium chloride- or lithium acetate-based) transformation methods can be used. Methods for transforming yeast strains to insert an exogenous LDH gene are described in WO 99/14335, WO 00/71738, WO 02/42471, WO 03/102201, WO 03/102152 and WO 03/049525; these methods are generally applicable for transforming *I. orientalis* cells in accordance with this invention. The vectors can either be cut with particular restriction enzymes or used as circular DNA.

In general, a vector is prepared that contains the LDH gene and associated promoter and terminator sequences. The vector may contain restriction sites of various types for linearization or fragmentation. Vectors may further contain a backbone portion (such as for propagation in *E. coli*) many of which are conveniently obtained from commercially available yeast or bacterial vectors.

The vector preferably contains one or more selection marker gene cassettes. A "selection marker gene" is one that encodes a protein needed for the survival and/or growth of the transformed cell in a selective culture medium. Typical selection marker genes encode proteins that (a) confer resistance to antibiotics or other toxins such as zeocin (sh ble gene from *Streptoalloteichus hindustanus*), G418 (kanamycin resistance gene of Tn903), hygromycin (aminoglycoside antibiotic resistance gene from *E. coli*), ampicillin, tetracycline, or kanamycin), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3$^-$) cannot grow on media lacking uracil. Thus a functional URA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with *I. orientalis*, for example), an auxotrophic mutant having the deficiency must be made in order to use URA3 as a selection marker for the strain. Methods for accomplishing this are well known in the art.

Preferred selection makers include the zeocin resistance gene, G418 resistance gene, hygromycin resistance gene and MEL5 (melibiase gene). The selection marker cassette will further include a promoter and terminator sequence, operatively linked to the selection marker gene, and which are operable in *I. orientalis*. Suitable promoters include those described above with respect to the LDH gene, as well as others such as are described in WO 99/14335, WO 00/71738, WO 02/42471, WO 03/102201, WO 03/102152 and WO 03/049525. An especially preferred promoter is a PGK or PDC promoter (or functional portion thereof) of the host strain, or a sequence having an identities score of at least 80, 85, 90 or 95% compared to such a PGK or PDC promoter. Suitable terminators include those described above with respect to the LDH gene. Either the promoter or terminator (or both) may be the same as that used with the LDH gene.

Targeted integration can be accomplished by constructing a vector having regions that are highly identical to (i.e. identities score of 80% or more, preferably 95% or more and most preferably 100%) to the upstream (5'-) and downstream (3'-) flanks of the target gene. Either or both of these regions may include a portion of the coding region of the target gene as well as a portion or all of the respective promoter or terminator regions. The LDH cassette (including associated promoters and terminators if different from those of the target gene) and selection marker(s) (with associated promoters and terminators as may be needed) will reside on the vector between the regions that are highly identical to the upstream and downstream flanks of the target gene. As mentioned, a preferred target gene is the IoPDC1A or IoPDC1B gene (or both) as disruption or deletion of one or both of those genes is preferred. However, other native genes may serve as targets for insertion of the LDH gene cassette.

Successful transformants can be selected for in known manner, by taking advantage of the attributes contributed by the marker gene, or by other characteristics (such as ability to produce lactic acid, inability to produce ethanol, or ability to grow on specific substrates) contributed by the inserted genes. Screening can be performed by PCR or Southern analysis to confirm that the desired insertions and deletions have taken place, to confirm copy number and to identify the point of integration of genes into the host cell's genome. Activity of the enzyme encoded by the inserted gene and/or lack of activity of enzyme encoded by the deleted gene can be confirmed using known assay methods.

Deletion or disruption of the PDC genes can be accomplished in a variety of ways, including, for example, methods analogous to those described in WO 99/14335, WO 02/42471, WO 03/049525, WO 03/102152 and WO 03/102201. In a method of particular interest (with respect to transforming *I. orientalis*), (1) the 5' and 3' flanking regions of one of the *I. orientalis* PDC genes are cloned, optionally together with a portion of the functional PDC gene; (2) a vector containing the 5' and 3' flanking regions is produced, and (3) the *I. orientalis* cell is transformed with the vector. A homologous recombination event results in a deletion of the functional PDC gene. It has been found that the 5' and 3' flanking regions for IoPDC1A can be used in the vector to delete or disrupt both IoPDC1A and IoPDC1B. Analogous methods may be used to disrupt or delete one or more PDC genes in other host cells useful in the invention.

The PDC deletion or disruption vector may include one or more functional structural genes, notably an LDH gene as described above, inserted between the 5' and 3' flanking portions of one of the PDC genes of the host cell. The functional gene preferably includes functional promoter and terminator sequences operatively linked to the structural gene. This approach allows for the simultaneous deletion of the PDC gene and insertion of the functional gene. The vector may include a selection marker gene instead of or in addition to the structural gene. Again, the selection marker gene is positioned on the vector between the 5' and 3' flanking portions of the PDC gene being targeted, and becomes inserted in the locus of the functional PDC gene. The use of a selection marker gene has the advantage of introducing a means of selecting for successful transformants. However, it may be possible to select for successful transformants based on their reduced or eliminated ability to produce ethanol, especially in transformants having disruptions or deletions of multiple PDC genes (such as both the IoPDC1A and IoPDC1B genes of *I. orientalis*).

In *I. orientalis*, it is possible to eliminate both IoPDC1A and IoPDC1B in a single step by transforming the host strain with a single vector containing the 5' flank of either target gene, a functional gene cassette including associated promoters and terminators, and/or a selection marker gene cassette including associated promoters and terminators, and the 3' flank of either target gene. An example of such a vector is that designated pMI356 in Example 2B. Transformations of *I. orientalis* with such a vector produces transformants having a single PDC allele deleted and transformants having a deletion of both the IoPDC1A and IoPDC1B alleles. Typically, at least one of the PDC alleles is replaced by a functional LDH gene (or other structural gene). Again, analogous methods are applicable with respect to other host cells having multiple PDC alleles.

Alternatively, it is possible in *I. orientalis* to delete IoPDC1A and IoPDC1B in a two-step process. For example, *I. orientalis* can be transformed with a vector as described above, and single PDC deletion strains transformed a second time with a like or similar vector to eliminate the second PDC allele. Examples 2D and 3B below illustrate such an approach.

The genetically modified yeast cell of the invention may include additional genetic modifications that provide some desired attribute to the cells. Additional modification(s) of particular interest confer to the cell the ability to ferment pentose sugars to desirable fermentation products. Among such modifications are (1) insertion of a functional exogenous xylose isomerase gene, (2) a deletion or disruption of a native gene that produces an enzyme that catalyzes the conversion of xylose to xylitol, (3) a deletion or disruption of a functional xylitol dehydrogenase gene and/or (4) modifications that cause the cell to overexpress a functional xylulokinase. Methods for introducing such modifications into yeast cells are described, for example, in WO 04/099381, incorporated herein by reference.

Genetically modified yeast cells of certain aspects of the invention include a functional, exogenous xylose isomerase (XI) gene that is preferably integrated into the genome of the host cell. In this context, "exogenous" means (1) the XI gene is not native to the host cell, (2) the XI gene is native to the host cell, but the genome of the host cell has been modified to provide additional functional copies of the native XI gene, or (3) both (1) and (2). Examples of suitable XI genes include XI genes native to *Piromyces* species E2 (such as the *Piromyces* sp. E2 xylA encoding gene sequence in Genbank (Assession #AJ249909)) and *Cyllamyces aberensis* as well as those obtained from other anaerobic fungi. Nucleotide sequences for the *Piromyces* species E2 and *Cyllamyces Aberensis* XI genes are identified as SEQ. ID. NOs. 58 and 151, respectively. Deduced amino acid sequences for proteins produced by these XI genes are identified as SEQ. ID. No. 59 and 152, respectively. A suitable bacterial XI gene is native to *Bacteroides thetaiotaomicron*. The nucleotide sequence for this *B. thetaiotamicron* XI gene is identified as SEQ. ID. NO. 162. The deduced amino acid sequence for the enzyme produced by this gene is identified as SEQ. ID. NO. 163. Suitable XI genes include those that are at least 60%, 80%, 90%, 95%, 98% or 99% homologous to SEQ. ID. NOs. 58 or 151. Suitable XI genes include those that encode for enzymes that are at least 60%, 80%, 90%, 95%, 98% or 99% homologous to SEQ. ID. NOs. 59 or 152. Some suitable xylose isomerase genes are no greater than 95% or no greater than 90% homologous to SEQ. ID. NO. 58 or encode an enzyme that is no greater than 95% or no greater than 90% homologous to SEQ. ID. NO. 59. Other suitable xylose isomerase genes are bacterial xylose isomerase genes that are at least 60, 80, 90, 95, 98 or 99% homologous to SEQ. ID. NO. 162 and/or produce an enzyme that is at least 60, 80, 90, 95, 98 or 99% homologous to SEQ. ID. NO. 163.

Percent homology of amino acid sequences can conveniently computed using BLAST version 2.2.1 software with default parameters. Sequences having an identities score and a positives score of at least XX %, using the BLAST version 2.2.1 algorithm with default parameters are considered at least XX % homologous. Particularly suitable xylose isomerase genes include those that encode for an enzyme that has an identities score of at least 60%, compared with SEQ. ID. NO. 163, an identities score of less than 95%, compared with SEQ. ID. NO. 59, and a positives score of less than 97%, compared with SEQ. ID. NO. 59.

The exogenous XI gene is under the control of a promoter and a terminator, both of which are functional in the modified yeast cell. As used herein, the term "promoter" refers to an untranscribed sequence located upstream (i.e., 5') to the translation start codon of a structural gene (generally within about 1 to 1000 bp, preferably 1-500 bp, especially 1-100 bp) and which controls the start of transcription of the structural gene. Similarly, the term "terminator" refers to an untranscribed sequence located downstream (i.e., 3') to the translation finish codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene such that the promoter or terminator, as the case may be, performs its transcriptional control function.

Promoters and terminator sequences may be native to the yeast cell or exogenous. Promoter and terminator sequences that are highly homologous (i.e., 90% or more, especially 95% or more, most preferably 99% or more homologous) in their functional portions to functional portions of promoter and terminator sequences, respectively, that are native to the cell are useful as well, particularly when the insertion of the exogenous gene is targeted at a specific site in the cell's genome.

A suitable promoter is at least 90%, 95% or 99% homologous to a promoter that is native to a yeast gene. A more suitable promoter is at least 90%, 95% or 99% homologous to a promoter for a gene that is native of the host cell. Particularly useful promoters include promoters for yeast pyruvate decarboxylase (PDC), phosphoglycerate kinase (PGK), xylose reductase, (XR), xylitol dehydrogenase (XDH) and transcription enhancer factor-1 (TEF-1) genes, especially from such genes as are native to the host cell.

A suitable terminator is at least 90%, 95% or 99% homologous to a terminator that is native to a yeast gene. The terminator may be at least 90%, 95% or 99% homologous to a terminator for a gene that is native of the host cell. Particularly useful terminators include terminators for yeast pyruvate decarboxylase (PDC), xylose reductase, (XR), xylitol dehydrogenase (XDH) or iso-2-cytochrome c (CYC) genes, or a terminator from the galactose family of genes in yeast, particularly the so-called GAL10 terminator. A S. cerevisiae GAL10 terminator and a S. cerevisiae CYC1 terminator have been shown to be effective terminators for exogenous XI genes in yeast.

The use of native (to the host cell) promoters and terminators, together with respective upstream and downstream flanking regions, can permit the targeted integration of the XI gene into specific loci of the host cell's genome, and for simultaneous integration the XI gene and deletion of another native gene, such as, for example, an XR, XDH or PDC gene.

A poly-his(tidine) tail may be present at the 3' end of the XI gene. A method for accomplishing this is described in Example 3 below. The presence of the poly-his tail may diminish the performance of the XI gene, however. The poly-his tail is not critical to the invention and may be omitted if desired.

The exogenous XI gene may be integrated randomly into the host cell's genome or inserted at one or more targeted locations. Examples of targeted locations include the loci of a gene that is desirably deleted or disrupted, such as an XR, XDH or PDC gene. In some embodiments, integration of the XI gene adjacent to the site of a native PDC gene appears to be related to improved performance of the modified yeast cell in producing fermentation products. Integration at the PDC locus may be accomplished with or without deletion or disruption of the native PDC gene, but it is preferred to maintain the native PDC gene intact and functional, particularly when a desired fermentation product is ethanol or other product that is a pyruvate metabolite.

Targeted integration can be accomplished by designing a vector having regions that are homologous to the upstream (5'-) and downstream (3'-) flanks of the target gene. Either of both of these regions may include a portion of the coding region of the target gene. The XI cassette (including associated promoters and terminators if different from those of the target gene) and selection markers (with associated promoters and terminators as may be needed) will reside on the vector between the regions that are homologous to the upstream and downstream flanks of the target gene.

The genetically modified yeast cell may contain a single copy or multiple copies of the exogenous XI gene. If multiple copies of the exogenous XI gene are present, from 2 to 10 or more copies may be present, such as from about 2-8 or from about 2-5 copies. Multiple copies of the exogenous XI gene may be integrated at a single locus (so they are adjacent each other), or at several loci within the host cell's genome. In an embodiment of particular interest, multiple copies of the exogenous XI gene are incorporated at or adjacent to the locus of a native PDC gene, with or without deletion or disruption of the native PDC gene. It is possible for different exogenous XI genes to be under the control of different types of promoters and/or terminators.

If the host cell contains one or more aldose reductase genes that produce enzymes that catalyze the conversion of xylose to xylitol, one or more of these genes is suitably disrupted or deleted. In general, the gene(s) selected for disruption or deletion are those which individually or collectively (1) account for at least 40%, preferably at least 50% of the host cell's xylose→xylitol reduction activity, and/or (2) are xylose reductase (XR) genes, i.e., genes that encode an enzyme specific to the xylose→xylitol reduction. It is generally preferred to delete or disrupt at least one XR gene. Deletion or disruption preferably achieves at least a 50% reduction in enzyme activity, and more preferably reduced xylose reductase activity to below 10 mU/mg or 5 mU/mg.

By "delete or disrupt", it is meant that the entire coding region of the gene is eliminated (deletion), or the gene or its promoter and/or terminator region is modified (such as by deletion, insertion, or mutation) so that the gene no longer produces an active enzyme, or produces an enzyme with severely reduced activity. The deletion or disruption can be accomplished by genetic engineering methods, forced evolution or mutagenesis and/or selection or screening. In the case of the XR or non-specific aldose reductase gene, a suitable method for accomplishing this is to clone the upstream and downstream flanking regions for the gene (which may include a portion of the coding region for the gene), produce a vector containing the cloned upstream and downstream flanks, and transform the host cell with the vector. The vector may contain other genetic material such as a marker gene or other gene that is desirably inserted into the genome of the host cell at the locus of the native XR or non-specific aldose gene (such as an XI gene, XK gene or a gene that enables the cell to produce a desired fermentation product, as an L- or D-LDH gene).

One method of deleting the XR or non-specific aldose reductase gene is to transform the host cell with a vector containing regions that are homologous to the upstream (5'-) and downstream (3'-) flanks of the target gene. Such flanking sequences can be obtained, for example, by amplifying the appropriate regions by PCR using suitably designed primers and genomic DNA as the template. Either of both of these regions may include a portion of the coding region of the target gene, although the vector should not contain the entire functional portion of the gene. Such flanking sequences are generally sequences of at least 50 base pairs, or at least 100 or at least 500 base pairs. Although there is in theory no upper limit to the length of the flanking sequence, it is preferably up to about 4000 base pairs, more preferably up to about 1200 base pairs in length. The flanking sequences are each at least 90%, preferably at least 95%, more preferably at least 98% and even more preferably at least 99% homologous to the corresponding sequences in the cell's genome. These flanking sequences may include the promoter and terminator sequences, respectively, of the target gene. The vector may in addition contain one or more selection marker cassettes (with associated promoters and terminators as may be needed) that advantageously reside between the regions that are homologous to the upstream and downstream flanks of the target gene. Such a vector can delete the target gene in a homologous recombination, inserting the selection marker gene at the locus of the deleted target gene. The vector may instead of or in addition to the selection marker cassette include another expression cassette, such as an XI expression cassette, and L- or D-LDH cassette or a xylulokinase expression cassette, all of which may include associated promoters and terminators. Vectors can also be designed to take advantage of spontaneous loopout events, such as are described in WO 03/102152.

If the host cell contains one or more xylitol dehydrogenase genes, one or more of these genes is suitably disrupted or deleted. XDH gene deletion or disruption can be performed in a way analogous to described before with respect to aldose reductase deletion or disruption. Deletion can be performed by incorporating upstream and downstream flanks of the XDH gene into a transformation vector, instead of the flanks of the XR or non-specific aldose reductase gene. As before, the vector may include one or more selection marker cassettes and/or one or more other expression cassettes. Deletion or disruption preferably achieves at least a 50% reduction in enzyme activity, and more preferably reduced xylitol dehydrogenase activity to below 2 mU/mg or 1 mU/mg.

The modified cell preferably expresses a xylulokinase enzyme having an activity of at least 100 mU/mg, such as at least 300 mU/mg or at least 500 mU/mg, measured as described in Example 5E below. The xylulokinase enzyme is referred to variously as EC 2.7.1.17 and systematically as ATP:D-xylulose 5-phosphotransferase. Its activity is generally ATP+D-xylulose=ADP+D-xylulose 5-phosphateXylulokinase (XK). Overexpression can be achieved, for example, by forced evolution (under conditions that favor selection of mutants that overexpress the enzyme), mutagenesis or by integrating one or more functional exogenous xylulokinase genes into the genome of the host cell. In this context, "exogenous" means (1) the XK gene is not native to the host cell, (2) the XK gene is native to the host cell, but the genome of the host cell has been modified to provide additional functional copies of the native XK gene, or (3) both (1) and (2). Suitable xylulokinase genes include yeast xylulokinase genes. A preferred example of a suitable XK gene is the *S. cerevisiae* XK gene (ScXKS1). A nucleotide sequence for the ScXKS1 gene is identified as SEQ. ID. NO. 83. The deduced amino acid sequence for the enzymes produced by the ScXKS1 gene is identified as SEQ. ID. NO. 84. Suitable XK genes include those that are at least 70%, 80%, 90%, 95%, 98% or 99% homologous to SEQ. ID. NO. 83. Suitable XK genes include those that encode for enzymes that are at least 70%, 80%, 90%, 95%, 98% or 99% homologous to SEQ. ID. NO. 84. Other suitable XK genes are native to *K. marxianus* or *C. sonorensis*, or are at least 70%, 80%, 80%, 95%, 98% or 99% homologous to either of these.

The exogenous XK gene is under the control of a promoter and a terminator, both of which are functional in the modified yeast cell. Suitable promoters and terminator sequences may be native to the host cell or exhibit a high homology (i.e., 90% or greater, especially 95% or greater, most preferably 99% or greater homology) to a native promoters or terminator. Such promoters and terminators are particularly useful when the exogenous XK gene is targeted at a specific site in the host cell's genome. Other suitable promoters and terminators are native to the organism from which the XK gene was obtained or exhibit a similarly high homology to such native promoter and/or terminators. For example, suitable promoters and terminators for the ScXKS1 gene identified above include promoters and terminators for *S. cerevisiae* genes. The promoter and/or terminators may be those native to the particular XK gene or exhibit a similarly high homology to such promoter and/and terminator.

Particularly useful promoters for the ScXKS1 gene include *S. cerevisiae* pyruvate decarboxylase (PDC), phosphoglycerate kinase (PGK), xylose reductase, (XR), xylitol dehydrogenase (XDH) and transcription enhancer factor-1 (TEF-1) promoters. Particularly useful terminators for the ScXKS1 gene include *S. cerevisiae* pyruvate decarboxylase (PDC), xylose reductase, (XR), xylitol dehydrogenase (XDH) or iso-2-cytochrome c (CYC) terminators, or a terminator from the galactose family of genes in yeast, particularly the so-called GAL10 terminator. A *S. cerevisiae* GAL10 terminator and a *S. cerevisiae* CYC1 terminator have been shown to be effective terminators for exogenous XI genes in yeast.

The exogenous XK gene may be integrated randomly into the host cell's genome, or inserted at one or more targeted locations, using methods analogous to those for inserting the XR gene, as discussed above. Examples of targeted locations include the loci of a gene that is desirably deleted or disrupted, such as an XR, XDH or PDC gene. As before, targeted integration can be accomplished by designing a vector having regions that are homologous to the upstream (5'-) and downstream (3'-) flanks of the target gene. Either of both of these regions may include a portion of the coding region of the target gene. The XK cassette (including associated promoters and terminators if different from those of the target gene) and selection markers (with associated promoters and terminators as may be needed) will reside on the vector between the regions that are homologous to the upstream and downstream flanks of the target gene.

The genetically modified yeast cell may contain a single copy or multiple copies (such as from 2 to 10 or more copies, from 2 to 8 or from 2 to 5 copies) of the exogenous XK gene. Multiple copies of the exogenous XK gene may be integrated at a single locus (so they are adjacent each other), or at several loci within the host cell's genome. It is possible for different exogenous XK genes to be under the control of different types of promoters and/or terminators.

In the fermentation process of the invention, the cell of the invention is cultivated in a fermentation medium that includes a sugar that is fermentable by the transformed cell. The sugar may be a hexose sugar such as glucose, glycan or other polymer of glucose, glucose oligomers such as maltose, maltotriose and isomaltotriose, panose, fructose, and fructose oligomers. If the cell is modified to impart an ability to ferment pentose sugars, the fermentation medium may include a pentose sugar such as xylose, xylan or other oligomer of xylose. Such pentose sugars are suitably hydrolysates of a hemicelluose-containing biomass. In case of oligomeric sugars, it may be necessary to add enzymes to the fermentation broth in order to digest these to the corresponding monomeric sugar for fermentation by the cell.

The medium will typically contain nutrients as required by the particular cell, including a source of nitrogen (such as amino acids, proteins, inorganic nitrogen sources such as ammonia or ammonium salts, and the like), and various vitamins, minerals and the like. *I. orientalis* is capable of satisfying its needs for nitrogen, phosphorus and magnesium from inorganic sources and so is capable of growing and fermenting in a chemically defined medium containing inorganic sources of these elements. Thus, the cells of the invention can be cultured in such a chemically defined medium. However, it is also possible to culture the cells of the invention in a complex medium that is not chemically defined and which may contain organic nitrogen sources such as proteins, partially digested proteins, or amino acids.

Other fermentation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C. A preferred temperature, particularly during the production phase, is from about 30-45° C.

During the production phase, the concentration of cells in the fermentation medium is typically in the range of about 0.1-20, preferably about 0.1-5, even more preferably about 1-3 g dry cells/liter of fermentation medium.

The fermentation may be conducted aerobically, microaerobically or anaerobically. Quasi-anaerobic conditions, in which no oxygen is added during the fermentation but dissolved oxygen is present in the fermentation medium at the start of the fermentation, can also be used. If desired, specific oxygen uptake rate can be used as a process control, as described in WO 03/102200. The cells of the invention exhibit a good ability to ferment sugars to lactic acid or lactic acid/ethanol mixtures, at good volumetric and specific productivities under even anaerobic conditions.

When the fermentation product is an acid, the medium may be buffered during the production phase of the fermentation so that the pH is maintained in a range of about 5.0 to about 9.0, preferably about 5.5 to about 7.0. Suitable buffering agents are basic materials that neutralize lactic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In a buffered fermentation, acidic fermentation products such as lactic acid are neutralized to the corresponding salt as they are formed. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the acid. The acid is then recovered through techniques such as liquid-liquid extraction, distillation, absorption, etc., such as are described in T. B. Vickroy, Vol. 3, Chapter 38 of Comprehensive Biotechnology, (ed. M. Moo-Young), Pergamon, Oxford, 1985; R. Datta, et al., FEMS Microbiol. Rev., 1995; 16:221-231; U.S. Pat. Nos. 4,275,234, 4,771,001, 5,132,456, 5,420,304, 5,510,526, 5,641,406, and 5,831,122, and WO 93/00440.

It is preferred, however, to conduct the fermentation so that the pH of the medium at the end of the fermentation is at or below the pKa of the acid fermentation product. A suitable final pH is suitably in the range of about 1.5 to about 3.5, in the range of from about 1.5 to about 3.0, or in the range from about 1.5 to about 2.5. The starting pH may be somewhat higher, such as from about 3.5 to about 6.0, especially from about 3.5 to about 5.5, or may be adjusted to a more acidic pH of 1.5 to about 3.5. The cells of this invention have been shown to have an unexpected ability to grow and produce well even in acidic fermentation media where the pH is below 3.5, below 3.0, below 2.5, and even below 2.0. *I. orientalis* cells with only basic genetic modifications, such as the insertion of an LDH gene and deletion of IoPDC1A and IoPDC1B genes, have been found to produce from 15-20 g/L lactic acid under anaerobic conditions in an unbuffered medium originally containing 10% by weight glucose.

Recovery of lactic acid from a low pH fermentation medium can be conducted using methods such as those described in U.S. Pat. No. 6,229,046.

The process of the invention can be conducted continuously, batch-wise, or some combination thereof.

The following examples are provided to illustrate the invention, but are not intended to limit the scope thereof. All parts and percentages are by weight unless otherwise indicated.

EXAMPLE 1A

Cloning of *I. orientalis* PGK (IoPGK1) Promoter Region; Construction of a Plasmid (pMI318, FIG. 1) having the *E. coli* Hygromycin Gene Under the Control of the IoPGK1 Promoter and the *S. Cerevisiae* GAL10 Terminator A 920 bp probe fragment of the *C. sonorensis* PGK1 gene is obtained from the genomic DNA of *C. sonorensis* in the same manner as described in Example 22 of WO 02/042471, using primers identified as SEQ. ID. NO. 1 and SEQ. ID. NO. 2. Genomic DNA is isolated from a growing *I. orientalis* strain and resuspended in 10 mM Tris-HCl+1 mM EDTA (pH 8) (TE). The *I. orientalis* genomic DNA is cut with HindIII, a Southern blot is prepared and hybridized using standard methods with the *C. sonorensis* PGK1 gene as a probe. Fragments of ~2 kb size are isolated from agarose gel and cloned into a HindIII-cut plasmid. Colony hybridization of the *E. coli* transformants with the PGK1 probe result in isolation of a HindIII fragment containing most of the *I. orientalis* PGK1 (IoPGK1) protein coding sequences but no promoter sequences, as verified by sequencing.

Genomic fragments containing the IoPGK1 promoter region are obtained with ligation-mediated PCR amplification (Mueller, P. R. and Wold, B. 1989, "In vivo footprinting of a muscle specific enhancer by ligation mediated PCR." Science 246:780-786). A mixture of a linker identified as SEQ. ID. NO. 3 and a linker identified as SEQ. ID. NO. 4 is ligated to HaeIII-digested *I. orientalis* genomic DNA with T4 DNA ligase (New England BioLabs). Samples of the ligation mixtures are used as templates for 50 l PCR reactions containing 0.1 M of a primer identified as SEQ. ID. NO. 5 and 1 M of a primer identified as SEQ. ID. NO. 6. The reaction mixture is heated at 94° C. for 3 minutes after 2 U of Dynazyme EXT is added. The reactions are cycled 30 times as follows: 1 minute at 94° C., 2 minutes at 68° C. and 2 minutes at 72° C., with a final extension of 10 minutes at 72° C. A diluted sample of this first PCR-amplification is used as the template in a nested PCR reaction (50 l) containing 0.05

M of a primer identified as SEQ. ID. NO. 7 and 0.5 M of a primer identified as SEQ. ID. NO. 8. The reaction mixture is heated at 94° C. for 3 minutes after 2 U of Dynazyme EXT is added. The reactions are then cycled 30 times as follows: 1 minute at 94° C., 2 minutes at 67° C. and 2 minutes at 72° C., with a final extension of 10 minutes at 72° C.

A ~600 bp PCR fragment is isolated and sequenced. Nested primers identified as SEQ. ID. NO. 9 and SEQ. ID. NO. 10 are designed and used in a ligation-mediated PCR amplification together with oligonucleotides identified as SEQ. ID. NO. 11 and SEQ. ID. NO. 12 similarly as above except that digested *I. orientalis* DNA is used and the PCR is carried out using an annealing temperature of 65° C.

The *I. orientalis* PGK1 promoter is PCR amplified using primers identified as SEQ. ID. NO. 13 and SEQ. ID. NO. 14 and the *I. orientalis* genomic DNA as the template. The fragment is filled in using the Klenow enzyme and then cut with XbaI. A 633 bp fragment is gel isolated and ligated to a 4428 bp fragment obtained by digesting a plasmid designated as pMI270 (described in FIG. 4 of WO 03/049525) with XhoI, filling the fragment in using the Klenow enzyme and 0.1 mM dNTP, and digesting with XbaI. Plasmid pMI270 contains the *E. coli* hygromycin gene linked to a *C. sonorensis* PGK1 promoter and a *S. cerevisiae* GAL10 terminator. The resulting plasmid is designated pMI318 (FIG. 1). Plasmid pMI318 contains the *E. coli* hygromycin gene under the control of the *I. orientalis* PGK1 promoter and the *S. cerevisiae* GAL10 terminator.

EXAMPLE 1B

Construction of a Plasmid (pMI321, FIG. 3) Containing the Hygromycin Gene Under the Control of the IoPGK1 Promoter and the *S. cerevisiae* GAL10 Terminator, and the *L. helveticus* LDH Gene Under the Control of the IoPGK1 Promoter and *S. cerevisiae* CYC1 Terminator The *I. orientalis* PGK1 promoter from Example 1A is PCR amplified using primers identified as SEQ. ID. NO. 15 and SEQ. ID. NO. 16 and the *I. orientalis* genomic DNA as the template. The fragment is filled in using the Klenow enzyme and 0.1 mM dNTP, and then cut with NcaI. A 633 bp fragment is gel isolated.

Plasmid pVR1 (described in WO 03/102152 FIG. 7) contains the *L. helveticus* LDH gene under the control of the *S. cerevisiae* TEF1 promoter and the *S. cerevisiae* CYC1 terminator. Plasmid pVR1 is digested with XhoI, filled in using the Klenow enzyme, and cut with NcoI. A 7386 bp fragment from plasmid pVR1 is ligated to the 633 bp IoPGK1 promoter fragment. The resulting plasmid is designated pMI320 (FIG. 2). Plasmid pMI320 contains the *L. helveticus* LDH gene under the control of the IoPGK1 promoter and *S. cerevisiae* CYC1 terminator.

Plasmids pMI318 (Ex. 1A, FIG. 1) and pMI320 are digested with ApaI and NotI. A 5008 bp fragment from plasmid pMI318 is ligated to a 1995 bp fragment from plasmid pMI320 to form plasmid pMI321 (FIG. 3).

The hygromycin gene (and its terminator) is positioned on plasmid pMI321 between two copies of the IoPGK1 promoter. This construct can permit a cell transformed with plasmid pMI321 to engage in a homologous recombination to "loop out" the hygromycin gene and terminator, together with one copy of the IoPGK1 promoter.

EXAMPLE 1C

Generation of an *I. orientalis* Mutant (CD 990) with Integrated LDH Gene and Hygromycin Resistance Genes by Transforming Wild-Type *I. orientalis* with Partially Digested Plasmid pMI321 (FIG. 3, Ex. 1B)

Plasmid pMI321 is partially restricted with XhoI, and the resulting mixture of linear and circularized DNA is used to transform a wild-type *I. orientalis* strain designated as ATCC PTA-6658, using standard lithium acetate methods as described in Gietz et al. (1992, Nucleic Acids Rs. 20:1425). The transformed cells are screened for hygromycin resistance. Several hygromycin-resistant colonies are cultured and the culture medium analyzed for the production of lactic acid. A hygromycin-resistant colony that produces lactic acid is designated strain CD990.

EXAMPLE 1D

Generation of an *I. orientalis* Mutant with an Integrated LDH Gene and Hygromycin Resistance Gene by Transforming Wild-Type *I. orientalis* with Partially Digested Plasmid pMI321 (FIG. 3, Ex. 1B)

Plasmid pMI321 is partially restricted with XhoI, and the resulting mixture of linear and circularized DNA is used to transform wild-type *I. orientalis* strain ATCC 32196, using standard lithium acetate methods as described before. The transformed cells are screened for hygromycin resistance. Several hygromycin-resistant colonies are cultured and the culture medium analyzed for the production of lactic acid. Several colonies are found to produce lactic acid.

EXAMPLE 1E

Generation of an *I. orientalis* Mutant with an Integrated LDH Gene and Hygromycin Resistance Gene by Transforming Wild-Type *I. orientalis* with Partially Digested Plasmid pMI320 and Digested Plasmid pMI321 (FIGS. 2, 3, Ex. 1B)

Plasmid pMI320 is partially digested with XhoI. Plasmid pMI321 is digested with SmaI and SalI. The digested materials are combined and used to transform wild-type *I. orientalis* strain ATCC PTA-6658, using standard lithium acetate methods as described before. The transformed cells are screened for hygromycin resistance. Several hygromycin-resistant colonies are cultured and the culture medium analyzed for the production of lactic acid. Several colonies are found to produce lactic acid.

EXAMPLE 1F

Generation of an *I. orientalis* Mutant with an Integrated LDH Gene and Hygromycin Resistance Genes by Transforming Wild-Type *I. orientalis* with Partially Digested Plasmid pMI320 and Digested Plasmid pMI321 (FIGS. 2, 3, Ex. 1B)

Plasmid pMI320 is partially digested with XhoI. Plasmid pMI321 is digested with SmaI and SalI. The digested materials are combined and used to transform a wild-type *I. orientalis* strain designated as ATCC 32196, using standard lithium acetate methods as described before. The transformed cells are screened for hygromycin resistance. Several hygromycin-resistant colonies are cultured and the culture medium analyzed for the production of lactic acid. One colony is found to produce lactic acid.

EXAMPLE 2A

Cloning of *I. orientalis* PDC (IoPDC1A) Promoter Region; Construction of a Plasmid (pMI355, FIG. 4) Having the *E. coli* Hygromycin Gene Under the Control of the IoPGK1 Promoter and the *S. cerevisiae* GAL10 Terminator, the *L. helveticus* LDH Gene Under the Control of the IoPGK1 Promoter and *S. cerevisiae* CYC1 Terminator, and the IoPDC1A 5' Flanking Region A genomic library of the native *I. orientalis* strain ATCC PTA-6658 is constructed into the SuperCos1 (Stratagene) cosmid vector according to instructions provided by the manufacturer. PDC-like sequences are amplified by PCR from the genomic DNA of the strain with primers designated as SEQ. ID. NO. 17 and SEQ. ID. NO. 18. A 700 bp fragment of a PDC gene is amplified. The genomic library is screened using hybridization techniques with labeled PCR fragments as probes as described in WO 03/049525 and cosmid clones containing the PDC gene are isolated and sequenced. The *I. orientalis* PDC1A 5' region from 1000 bp to 167 bp upstream of the start of the open reading frame is PCR amplified using primers identified as SEQ. ID. NO. 19 and SEQ. ID. NO. 20 and the *I. orientalis* PDC cosmid DNA as the template. The amplified gene (from start to finish codons) has the sequence identified as SEQ. ID. NO. 97. The fragment is cut with SalI and SacI. An 836 bp fragment is gel isolated and ligated to a 6992 bp fragment obtained by digesting plasmid pMI321 (Example 1B, FIG. 3) with SalI and SacI. The resulting plasmid is named pMI355 (FIG. 4).

EXAMPLE 2B

Cloning of *I. orientalis* PDC (IoPDC1A) Terminator Region; Construction of Plasmids (pMI356 and pMI357, FIGS. 5 and 6) Having the IoPDC1A 5' Flanking Region, the *E. coli* Hygromycin Gene Under the Control of the IoPGK1 Promoter and the *S. cerevisiae* GAL10 Terminator, the *L. helveticus* LDH Gene Under the Control of the IoPGK1 Promoter and *S. cerevisiae* CYC1 Terminator, and the IoPDC1A 3' Flanking Region The *I. orientalis* PDC 3' region corresponding to sequences from 233 bp to 872 bp downstream of the PDC translation stop codon is PCR amplified using primers identified as SEQ. ID. NO. 21 and SEQ. ID. NO. 22 and the *I. orientalis* PDC1A cosmid DNA (Example 2A) as the template. The fragment is cut with ApaI and SmaI. A 630 bp fragment is gel isolated and ligated to a 7809 bp fragment obtained by digesting plasmid pMI355 (Ex. 2A, FIG. 4) with ApaI and SmaI. The resulting plasmid is named pMI356 (FIG. 5). It contains the hygromycin and LDH cassettes from plasmid pMI355 between the 5' flank and a portion of the 3' flank of the IoPDC1A gene.

The *I. orientalis* PDC1A 3' region corresponding to sequences from 524 bp upstream to 217 bp downstream of the PDC translation stop codon is PCR amplified using primers identified as SEQ. ID. NO. 23 and SEQ. ID. NO. 24 and the *I. orientalis* PDC cosmid DNA (Example 2A) as the template. The fragment is cut with ApaI and SmaI. A 764 bp fragment is gel isolated and ligated to a 7809 bp fragment obtained by digesting plasmid pMI355 with ApaI and SmaI. The resulting plasmid is named pMI357 (FIG. 6). It contains the hygromycin and LDH cassettes from plasmid pMI355 between the 5' flank of the IoPDC1A gene. Plasmid pMI357 differs from plasmid pMI356 with respect to the portion of the 3' IoPDC1A flank that is present.

EXAMPLE 2C

Generation of an *I. orientalis* Mutant (ATCC/357-5) with Deleted PDC Gene and Integrated *L. helveticus* LDH Gene and Hygromycin Resistance Gene by Transforming Wild-Type *I. orientalis* with Plasmid pMI357 (FIG. 6, Ex. 2B)

Plasmid pMI357 is restricted with SacI and ApaI and used to transform *I. orientalis* strain ATCC 32196, using standard chemical methods as described before.

Colonies that grow on the hygromycin media are subjected to Southern analysis to confirm the integration of the LDH gene from plasmid pMI357 and to confirm the deletion of the IoPDC1A and/or IoPDC1B allele. A transformant containing the LDH gene and a deletion of one of the IoPDC1A or IoPDC1B alleles is designated as ATCC/357-5.

EXAMPLE 2D

Generation of *I. orientalis* Mutants (CD1027 and CD1030) with Deleted PDC Gene and Integrated *L. helveticus* LDH Gene and Hygromycin Resistance Gene, by Transforming Wild-Type *I. orientalis* with Plasmid pMI356 (FIG. 5, Ex. 2A)

Plasmid pMI356 is restricted with SacI and ApaI and used to transform *I. orientalis* strain ATCC PTA-6658, using standard chemical methods as described before.

Colonies that grow on the hygromycin media are selected. Southern analysis of HindIII-XbaI cut genomic DNA hybridized with LhLDH and PDC 5' probes confirm the integration of the LDH gene from plasmid pMI356 and the deletion of the IoPDC1B gene in a transformant, which is designated as CD1030. A transformant having integrated LDH and a deletion of the IoPDC1A gene is designated as CD1027.

EXAMPLE 2E

Generation of an *I. orientalis* Mutant (ATCC/356-23) with Deleted IoPDC1A Gene and Integrated *L. helveticus* LDH Gene and Hygromycin Resistance Gene, by Transforming Wild-Type *I. orientalis* with Plasmid pMI356 (FIG. 5, Ex. 2A)

Plasmid pMI356 is restricted with SacI and ApaI and used to transform wild-type *I. orientalis* strain ATCC 32196, using standard chemical methods as described before.

Colonies that grow on the hygromycin media are selected. Southern analysis of HindIII-XbaI cut genomic DNA hybridized with LhLDH and PDC 5' probes confirm the integration of the LDH gene from plasmid pMI356 and the deletion of one of the IoPDC1A or IoPDC1B alleles in a transformant, which is designated as ATCC/356-23.

EXAMPLE 3A

Construction of Plasmid pMI433 (FIG. 8) Containing the IoPDC1A 5' Flanking Region, the ScMEL5 Gene Under the Control of the IoPGK1 Promoter, the *L. helveticus* LDH Gene Under the Control of the IoPGK1 Promoter and ScCYC1 Terminator, and the IoPDC1A 3' Flanking Region The *I. orientalis* PGK1 promoter is PCR amplified using primers identified as SEQ. ID. NO. 25 and SEQ. ID. NO. 26 and the *I. orientalis* genomic DNA as the template. The fragment is filled in using the Klenow enzyme and 0.1 mm dNTP, and then cut with SphI. A 669 bp fragment is gel isolated. A plasmid designated as pMI233 (described in FIG. 23C of WO 03/049525) is cut with XhoI. The fragment is filled in with the Klenow enzyme and cut with SphI. The 4534 bp and the 669 bp fragments are ligated and the resulting plasmid is named pMI319 (FIG. 7). Plasmid pMI319 contains the *S. cerevisiae* MEL5 (ScMEL5) gene and the IoPGK1 promoter region.

Plasmid pMI319 plasmid is cut with ApaI, made blunt ended with T4 polymerase, and cut with NotI. A 2317 bp fragment is gel isolated. It is ligated to a 6498 bp fragment obtained by digesting plasmid pMI357 (Example 2B, FIG. 6) with SalI, making it blunt ended with the Klenow enzyme and then cutting with NotI. The resulting plasmid contains the ScMEL5 gene (with its native terminator) in place of the hygromycin gene of plasmid pMI357. The resulting plasmid is designated pMI433 (FIG. 8).

EXAMPLE 3B

Generation of *I. orientalis* Mutants (C258/433-3 and C258/433-4) with Deleted IoPDC1A and IoPDC1B Genes and Integrated *L. helveticus* LDH Gene and ScMEL5 Gene by Transforming Mutant Strain CD1027 (Ex. 2B) with Plasmid pMI433 (FIG. 8, Ex. 3A)

Mutant strain CD1027 is transformed with a 5.9 kb SacI/ApaI fragment from plasmid pMI433 using standard chemical methods. Southern analysis is conducted on transformants that exhibit melibiase activity, using genomic DNA digested with various enzyme combinations and carried out with LhLDH and PDC 5' probes. Two transformants that have lost the IoPDC1B allele and gained a second copy of the LhLDH gene are designated C258/433-3 and C258/433-4, respectively. However, the integration occurs differently in the two transformants, in that the LhLDH 3' band corresponding to the LhLDH cassette of plasmid pMI433 appears differently in the two strains. It is not clear whether the inserted LhLDH expression cassette is intact in these transformants.

EXAMPLE 4

Generation of an *I. orientalis* Mutant (CD1184) with Deleted IoPDC1A and IoPDC1B Alleles and Integrated LhLDH Gene in One Step by Transforming Wild-Type *I. orientalis* Strain with Plasmid pMI356 (FIG. 5, Ex. 2B)

*I. orientalis* strain ATCC PTA-6658 is transformed with plasmid pMI356 using the general method described in Example 3B. Transformed strains that grow on hygromycin plates are cultured. A transformant that does not produce ethanol is selected for Southern analysis, which confirms the deletion of both the IoPDC1A and IoPDC1B alleles and insertion of at least one copy of the LhLDH gene. This strain is designated CD1184.

EXAMPLE 5

Generation of an *I. orientalis* Mutant (CD 1270) with Deleted IoPDC1A and IoPDC1B Alleles and Integrated LhLDH Gene in One Step by Transforming Wild-Type *I. orientalis* Strain ATCC32196 with Plasmid pMI356 (FIG. 5, Ex. 2B)

*I. orientalis* strain ATCC 32196 is transformed with plasmid pMI356 using the general method described in Example 3B. Transformed strains that grow on hygromycin plates are cultured. A transformant that does not produce ethanol is selected for Southern analysis, which confirms the deletion of both the IoPDC1A and IoPDC1B alleles and the insertion of a copy of the LhLDH gene. This strain is designated CD1270.

EXAMPLE 6

Microaerobic Shake Flask Characterizations of Strains CD 990 (Ex. 1C) ATCC/357-5 (Ex. 2C), ATCC 356-23 (Ex. 2E), CD1030 (Ex. 2D), CD1184 (Ex. 4) and CD1270 (Ex. 5) in Non-Buffered Defined Medium Transformants CD990, ATCC/357-5, ATCC 356-23, CD1030, CD1184 and CD1270 are separately cultivated in 50 mL yeast nitrogen base (YNB) without amino acids, supplemented with 100 g/L glucose in a 250 mL baffled flask. The cultivations are not buffered, so pH within the medium falls as lactic acid is produced, to a final pH of 2.0±0.1 in each instance. Each flask is inoculated to an $OD_{600}$ of 0.2 with cells grown on yeast peptone plus glucose plates. The cultivations are maintained at a temperature of 30° C. with shaking at 100 rpm. Samples are withdrawn periodically during cultivation, and $OD_{600}$ is measured. Cells are recovered from each sample by centrifugation and the supernatant analyzed by HPLC for lactic acid, glucose and ethanol.

HPLC analyses are conducted with a Waters 2690 Separation Module and Water System Interfase Module liquid chromatography coupled with a Waters 2414 differential refractometer and Waters 2487 dual absorbance detector. The liquid chromatography columns are a 50×7.8 mm Fast Juice column from Phenomenex and a 100×7.8 mm Fast Acid Analysis column from Bio-Rad. The columns are equilibrated with 2.5 mM H2SO4 in water at 60° C. and samples are eluted with 2.5 mM H2SO4 in water at 0.5 ml/min flow rate. Data acquisition is done using Waters Millennium software.

The single PDC deletant strains (ATCC/357-5, ATCC/356-23 and CD1030) all produce both ethanol and lactic acid. Glucose consumption for these three strains is nearly linear throughout the 168 hour cultivation, with each consuming about 50% of the glucose after about 72 hours and essentially all of the glucose after about 168 hours. Each of these strains produces about 20-24 g/L of ethanol after 168 hours. Lactic acid production peaks after about 96 hours at a level of 15-20 g/L for each of these strains. The strains thereafter consume a small amount of lactic acid. Lactic acid yields for these strains peak at about 35% after 48 hours, and decline thereafter due to lactic acid consumption and continued production of ethanol.

Strain CD990, which has no PDC deletion, performs similarly to the single PDC deletant strains.

The double PDC deletant strains (CD1184 and CD1270) produce lactic acid but no ethanol. These strains consume glucose more slowly than do the others, with approximately 48-55% of the glucose being unconsumed after 168 hours. Strain CD1270 produces lactic acid through the first 96 hours of cultivation, after which lactic acid titers increase only slightly. Strain CD1270 produces a peak lactic acid yield of about 56%. Strain CD1184 continues to produce lactic acid through the entire cultivation period, with lactic acid titer at the end of the cultivation being about 31 g/L. Lactic acid yield for this strain is about 55%.

EXAMPLE 7

Microaerobic Two-Stage Shake Flask Characterizations of Strains CD990 (Ex. 1C), CD1030 (Ex. 2D), CD1184 (Ex. 4) and CD1270 (Ex. 5) in Buffered Defined Medium Transformants CD 990, CD1030, CD1184 and CD1270 are separately grown on yeast peptone plus 5% glucose. The cells are used to inoculate separate flasks containing YNB+ 5% glucose+0.5 M MES, pH 5.5 media to $OD_{600=0.1}$. The flasks are incubated overnight at 30° C. and 250 rpm shaking. The cells are then transferred to separate flasks containing 50 ml YNB+10% glucose+4 g $CaCO_3$ to $OD_{600}$=12, and incubated for 5 days at 30° C. and 100 rpm shaking. Samples are withdrawn periodically during cultivation, and $OD_{600}$ is measured. Cells are recovered from each sample by centrifugation and the supernatant analyzed by HPLC for lactic acid, glucose and ethanol as described in Example 6.

The single PDC deletant strain CD1030 produces both ethanol and lactic acid. It consumes all of the glucose within 48 hours and produces about 56 g/L lactic acid. Lactic acid yield for this strain is just under 60%. This strain also produces about 13 g/L of ethanol. This performance is very similar to that of CD990, which has the LhLDH gene without either PDC deletion.

The double PDC deletant strains (CD1184 and CD1270) again produce lactic acid but no ethanol. Strain CD1270 consumes glucose slightly faster than strain CD1184, but at about the same rate as strain CD1030. Lactic acid titer for strain CD1270 peaks at about 85 g/L after 50 hours, and declines slightly thereafter as the strain begins to consume lactic acid when glucose becomes depleted. Lactic acid yield for this strain is about 85% after 50 hours. Strain CD1184 consumes about 90% of the glucose after 50 hours, and consumes the remainder over the next 72 hours. It produces a maximum lactic acid titer of about 73 g/L and a maximum lactic acid yield of about 80%.

EXAMPLE 8

Quasi-Anaerobic Two-Stage Shake Flask Characterizations of Strains CD990 (Ex. 1C), CD1030 (Ex. 2D), CD1184 (Ex. 4) and CD1270 (Ex. 5) in Buffered Defined Medium Transformants CD 990, CD1030, CD1184 and CD1270 are separately grown on yeast peptone plus 2% glucose. The cells are used to inoculate separate flasks containing yeast peptone+10% glucose and incubated overnight at 30° C. and 250 rpm shaking. The cells are then transferred to separate flasks containing 50 ml yeast peptone+10% glucose to $OD_{600}$=13. The flasks are sealed with water locks and incubated for about 6 days at 30° C. and 100 rpm shaking in yeast peptone+10% glucose. However, residual air is not removed from the head space of the flask and no measures are taken to remove dissolved oxygen. These cultivations are therefore not strictly anaerobic, as some oxygen is available at least at the beginning of the cultivation.

The pH of the broths falls to 3.2±0.1 during the cultivations due to the production of lactic acid.

Samples are withdrawn periodically during cultivation, and $OD_{600}$ is measured. Cells are recovered from each sample by centrifugation and the supernatant analyzed by HPLC for lactic acid, glucose and ethanol as described in Example 6.

The single PDC deletant strain CD1030 produces about 19 g/L lactic acid after 24 hours, about 24 g/L lactic acid after 72 hours and slightly more than 25 g/L lactic acid after 141 hours. Strain CD990, which has no PDC deletion, produces about 20 g/L lactic acid after 24 hours and about 22 g/L lactic acid after 141 hours. Strains CD990 and CD1030 both produce ethanol as well as lactic acid.

The double PDC deletant strain CD1184 produces about 15 g/L lactic acid after 24 hours and about 18 g/L lactic acid after 72 hours. The double PDC deletant strain CD1270 produces about 15.5 g/L lactic acid after 24 hours, about 14.5 g/L lactic acid after 72 hours and about 19.5 g/L lactic acid after 141 hours.

EXAMPLE 9A

Microaerobic Batch Culture Cultivation of Strain CD1184 (Ex. 4) at pH 3

Duplicate single-stage batch culture reactors containing a defined medium that includes ammonium sulphate, potassium dihydrogen phosphate and magnesium sulphate, trace elements, vitamins and 83 g/L glucose are inoculated with 1 mL strain CD1184. pH of the medium is adjusted to 3.3 prior to adding the cells. The cells are cultured at 30° C. under 380 rpm agitation and 0.1 vvm aeration. These conditions lead to an oxygen uptake rate (see WO 03/102200) of 2.9-3.1 mmol/L/h. The pH of the culture is allowed to drop to 3.0 as cells grow and begin to produce lactic acid. Afterward, pH is maintained at 3.0 by addition of potassium hydroxide.

HPLC analyses are conducted as described above. Under these conditions, the organism produces 67 g/L lactic acid after ~120 hours fermentation. The lactate production rate is 0.62 g/L/hr and the yield of lactate on glucose is 0.76 g/g.

EXAMPLE 9B

Aerobic Batch Culture Cultivation of Strain CD1184 (Ex. 4) at pH 3

A single-stage batch culture reactor containing a defined medium that includes ammonium sulphate, potassium dihydrogen phosphate and magnesium sulphate, trace elements, vitamins, defoaming agent, and 90 g/L glucose are inoculated with 1 mL strain CD1184. The pH of the medium is adjusted to about 3.3 prior to adding the cells. The pH of the culture is allowed to drop to 3.0 as cells grow and begin to produce lactic acid. Afterward, pH is maintained at about 3.0 by addition of potassium hydroxide. The cells are cultured at 30° C. under 490 rpm agitation and 0.1 vvm aeration. These conditions lead to an oxygen uptake rate (see WO 03/102200) of about 8 mmol/L/hr. An additional 40 g/L glucose is added to the fermentation after about 50 hours of fermentation HPLC analyses are conducted as described above. Under these conditions, the organism produces 80 g/L lactic acid after ~90 hours fermentation (including a lag phase of about 18 hours during which little fermentation occurs). Over the entire batch fermentation, the lactate production rate is 1.0 g/L/hr and the yield of lactate on glucose is 0.71 g/g. Over the period of time between the end of the lag phase (18 hours) and a titer of 70 g/L lactate is reached (69 hours), the lactate production rate is 1.5 g/L/hr and the yield of lactate on glucose is 0.75 g/g after accounting for dilution effects from the addition of glucose and potassium hydroxide.

EXAMPLE 10A

Construction of a Plasmid (pMI445, FIG. 11) Containing the S. cerevisiae MEL5 Gene Cassette Between Identical K. thermotolerans Repeats The entire K. marxianus CYB2 (KmCYB2) gene cassette, including promoter and terminator regions, is PCR amplified from the genomic DNA of a native *K. marxianus* strain, with introduction of BamHI and SalI restriction sites, by PCR using primers identified as SEQ. ID. NO. 27 and SEQ. ID. NO. 28. The PCR product is ligated to a commercial vector designated as pUC18 (from Invitrogen Corp., Carlsbad, Calif.) that is digested with BamHI and SalI. The resulting plasmid is designated as pMM25 (FIG. 9).

A 705 bp sequence identified as SEQ. ID. NO. 29 is PCR-amplified from the genomic DNA of *K. thermotolerans*, with introduction of SphI and SalI restriction sites, using primers identified as SEQ. ID. NO. 30 and SEQ. ID. NO. 31. This *K. thermotolerans* sequence does not encode for any active protein. Plasmid pMM25 is digested with SphI and SalI and the *K. thermotolerans* sequence is ligated to it upstream (5') to the KmCYB2 cassette to form a plasmid designated as pMM27.

An identical *K. thermotolerans* sequence is PCR-amplified with addition of BamHI and XmaI restriction sites, using primers identified as SEQ. ID. NO. 32 and SEQ. ID. NO. 33. Plasmid pMM27 is digested with BamHI and XmaI and the *K. thermotolerans* sequence is ligated to it downstream (3') from the KmCYB2 cassette to form a plasmid designated as pMM28 (FIG. 10). Plasmid pMM28 contains the KmCYB2 cassette flanked by identical *K. thermotolerans* sequences, both oriented in the same direction.

Plasmid pMM28 is digested with BamHI, filled in with the Klenow enzyme, and digested with SalI. A 4077 bp fragment so obtained is ligated to a 2317 bp fragment obtained by digesting pMI433 (FIG. 8, Ex. 3A) with NatI, filling the overhangs in with the Klenow enzyme, and digesting with SalI. The resulting plasmid is designated pMI445 (FIG. 11).

EXAMPLE 10B

Isolation of CYB2 Homologues from *I. orientalis*

The KmCYB2 gene is used as a probe to isolate homologous genes from a library of genomic DNA obtained from a growing *I. orientalis* strain. The probe is synthesized by PCR using oligonucleotides SEQ. ID. NO. 34 and SEQ. ID. NO. 35 as primers and *K. marxianus* genomic DNA as the template, and labeled with $^{32}$P. The KmCYB2 gene so obtained is used to isolate *I. orientalis* CYB2 genes from a genomic library of *I. orientalis*. A Southern blot containing EcoRI-digested DNA from six *I. orientalis* cosmid clones and genomic DNA from a wild-type *I. orientalis* strain are prepared and hybridized with the KmCYB2 gene. ~1.5 kbp bands are detected, isolated from gel and cloned into an EcoRI-digested pBluescript SK(-) plasmid. The bands are sequenced using M13 reverse and forward primers. Sequence-specific primers are designed based on the sequences so obtained. Two CYB2 genes are identified, which are designated IoCYB2A and IoCYB2B. The coding region and approximately 1 kbp of the 5' and 3' flanking regions of each of the clones are sequenced. The sequences are identified as SEQ. ID. NO. 36 and SEQ. ID. NO. 37, respectively.

EXAMPLE 10C

Construction of a Plasmid (pMI447, FIG. 14) Containing the *I. orientalis* PDC1A Promoter, *K. thermotolerans* Sequence, ScMEL1 Cassette, Second Identical *K. Thermotolerans* Sequence, LhLDH Gene Cassette and *I. orientalis* PDC1A Terminator A vector designated as pNC16 is obtained from the National Research Energy Laboratories in Golden, Colo. This plasmid contains the *S. cerevisiae* MEL1 gene under the control of the *S. cerevisiae* PDC1 promoter and *S. cerevisiae* GAL10 terminator. The MEL1 gene cassette is PCR-amplified with addition of BglII and SacI restriction sites using primers designated as SEQ. ID. NO. 38 and SEQ. ID. NO. 39. Plasmid pMM28 (Ex. 10A. FIG. 10) is digested with BglII and SacI and ligated to the MEL1 cassette. This simultaneously deletes the KmCYB2 cassette of plasmid pMM28 and replaces it with the MEL1 cassette. The resulting plasmid is designated pMM31. It contains the MEL1 cassette flanked by the repeating *K. thermotolerans* sequences.

A ~2 kbp flanking region directly 3' of the KmCYB2 coding region is amplified with introduction of XmaI and SacI restriction sites by PCR using primers identified as SEQ. ID. NO. 40 and SEQ. ID. NO. 41 and genomic DNA as the template. The resulting fragment is ligated to XmaI/SacI-digested plasmid pMM31 to insert the 3' CYB2 flank downstream (3') of the *K. thermotolerans* sequence that is itself downstream of the MEL1 cassette. The resulting plasmid is designated as pMM32.

A ~2 kbp flanking region directly 5' of the KmCYB2 coding region is amplified with introduction of AatII and NarI restriction sites by PCR using primers identified as SEQ. ID. NO. 42 and SEQ. ID. NO. 43 and genomic DNA as the template. The resulting fragment is ligated to the AatII/NarI-digested plasmid pMM32. The resulting plasmid (designated pMM35, FIG. 12) contains, in order, the 5' KmCYB2 flanking region, a first identical *K. thermotolerans* sequence, the MEL1 cassette, the second identical *K. thermotolerans* sequences and the 3' KmCYB2 flanking region.

The *K. thermotolerans* sequence is amplified by PCR using primers identified as SEQ. ID. NO. 44 and SEQ. ID. NO. 45, with plasmid pMM35 as the template. The PCR product is digested with NotI and SpeI. The resulting 712 bp fragment is ligated to an 8798 bp fragment obtained by digesting pMI433 (Ex. 3A, FIG. 8) with SpeI and NotI. The resulting plasmid is designated pMI446 (FIG. 13). It contains, in order, the *I. orientalis* PDC promoter, ScMEL5 gene cassette, the *K. thermotolerans* sequence, the LhLDH cassette, and *I. orientalis* PDC1A terminator.

The *K. thermotolerans* sequence is amplified by PCR using primers identified as SEQ. ID. NO. 46 and SEQ. ID. NO. 47, using plasmid pMM35 as the template. The PCR product is digested with SalI. The resulting 711 bp fragment is ligated to a 9510 bp SalI fragment of plasmid pMI446. The resulting plasmid is designated pMI447 (FIG. 14). It contains, in order, the *I. orientalis* PDC promoter, first *K. thermotolerans* repeating sequence, ScMEL5 cassette, second *K. thermotolerans* repeating sequence, LhLDH gene cassette and *I. orientalis* PDC terminator.

EXAMPLE 10D

Construction of a Plasmid (pMI448, FIG. 15) Containing a *K. thermotolerans* Sequence, ScMEL5 Gene Cassette, Second Identical *K. thermotolerans* Sequence and IoCYB2A Terminator The 3' flanking region of the IoCYB2A gene from ~90-676 bp downstream of the open reading frame is amplified by PCR using primers identified as SEQ. ID. NO. 48 and SEQ. ID. NO. 49 and a cosmid clone containing the *I. orientalis* CYB2A gene as the template. The PCR product is digested with SacI and SmaI. A 607 bp fragment is obtained and ligated to a 6386 fragment obtained by digesting plasmid pMI445 (Example 10A, FIG. 11) with SacI and SmaI. The resulting plasmid is designated pMI448 (FIG. 15).

EXAMPLE 10E

Isolation of URA3 Gene from *I. orientalis*

A fragment of the *I. orientalis* URA3 gene (IoURA3) is amplified by PCR from genomic DNA of a native strain of *I. orientalis* using primers identified as SEQ. ID. NO. 50 and SEQ. ID. NO. 51. A ~650 bp fragment is obtained, which is sequenced to confirm close homology to the URA3 genes of other yeasts. This ~650 bp fragment is then used as a probe for isolating the full length gene from a genomic cosmid library of the *I. orientalis* native strain. A clone is obtained, which is purified and sequenced. The clone includes the IoURA3 functional gene and flanking regions, and includes a sequence identified as SEQ. ID. NO. 52. The open reading frame of this gene encodes for a protein having 262 amino acids. This amino acid sequence is identified as SEQ. ID. NO. 53.

EXAMPLE 10F

Construction of Transformation Plasmid pMI457 (FIG. 16) Containing the IoURA3 Promoter, ScMEL5 Gene Cassette Between Identical *K. thermotolerans* Sequences, LhLDH Gene Cassette and IoURA3 Terminator and Transformation Plasmid pMI458 (FIG. 17) Containing the IoURA3 Promoter, ScMEL5 Gene Cassette Between Identical *K. thermotolerans* Sequences, and IoURA3 Terminator The IoURA3 3' flanking sequence of *I. orientalis* is amplified with primers identified as SEQ. ID. NO. 54 and SEQ. ID. NO. 55 with an *I. orientalis* cosmid clone containing the URA3 gene as the template. A 630 bp fragment is obtained, which is cut with SmaI and ApaI and ligated to a SmaI/ApaI fragment of plasmid pMI447 (Ex. 10C, FIG. 14) to produce a plasmid designated pMI455. Plasmid pMI455 contains the *I. orientalis* PDC promoter, ScMEL5 gene cassette between repeating *K. thermotolerans* sequences, LhLDH gene cassette and IoURA3 3' flank.

The IoURA3 5' flanking sequence of *I. orientalis* is amplified with primers identified as SEQ. ID. NO. 56 and SEQ. ID. NO. 57 with the *I. orientalis* cosmid clone containing the URA3 gene as the template. A 554 bp fragment is obtained, which is cut with SphI and ligated to a 6994 bp SphI-cut fragment of plasmid pMI448 (Ex 10C, FIG. 15) to produce plasmid pMI456. Plasmid pMI456 contains the IoURA3 promoter, the ScMEL5 gene cassette between repeating *K. thermotolerans* sequences and the *I. orientalis* CYB2A terminator.

Plasmid pMI455 is cut with Sac/and SalI. The resulting 8542 bp fragment is ligated to a 1264 bp SacI-XhoI fragment of plasmid pMI456 to produce plasmid pMI457 (FIG. 16).

Plasmid pMI457 is cut with Not/and SmaI, filled in using the Klenow enzyme and the resulting 7834 bp fragment religated to form plasmid pMI458 (FIG. 17).

EXAMPLE 10G

Generation of *I. orientalis* Mutants (CD1439 and CD1440) with Two (CD1439) and One (CD1440) Copies of LhLDH Gene and ScMEL5 Cassette Inserted at Locus of Native URA3 Gene (and URA3 Deletion) by Transforming Mutant Strain CD1184 (Ex. 4) with Plasmids pMI457 (Ex. 10F, FIG. 16) and pMI458 (Ex. 10F, FIG. 17)

Mutant stain CD1184 is transformed with plasmid pMI457 using the general method described in Example 3B and plated onto YPD+X-gal plates. Transformants containing the ScMEL5 gene are identified based on blue color. Those transformants are screened via PCR using primers identified as SEQ. ID. NO. 58 and SEQ. ID. NO. 59 to identify URA3 integrants. Positive transformants are further identified by Southern analysis of EcoRV-HindIII and NcoI-BsmI-digested DNA. A digoxigenin-labeled URA3 probe is synthesized using primers identified as SEQ. ID. NO. 56 and SEQ. ID. NO. 55 and the cosmid clone containing the *I. orientalis* URA3 gene as the template. A transformant that produces the expected bands is identified as strain CD1439. Strain CD1439 has the same genetic background as strain CD1184, except it has an extra copy of the LhLDH cassette and ScMEL5 cassette at the locus of a native URA3 gene.

Strain CD1440 is produced in the same manner, except it is transformed with plasmid pMI458. Plasmid pMI458 lacks the LhLDH cassette, but otherwise effects the same transformation as plasmid pMI457. Strains CD1439 and CD1440 therefore have the same genetic background except for the number of LhLDH cassettes.

EXAMPLE 11

Microaerobic Shake Flask Characterizations of Strains CD 1184 (Ex. 4), CD1439 (Ex. 10F) and CD1440 (Ex. 10F).

Strains CD1439 and CD1440 are separately inoculated to an initial OD600 of 0.15 into 50 ml of YP+100 g/L glucose in non-baffled flasks. The flasks are incubated at 30° C. with 100 rpm shaking and assayed after 22, 47, 62, 91, 119 and 143 hours.

Samples for enzyme activity measurements (5 mL) are collected periodically by centrifugation. The cell pellets are washed with 1 mL of cold 10 mM $K_2HPO_4/KH_2PO_4$ (pH 7.5) supplemented with 2 mM EDTA. The washed pellets are resuspended in 1 mL of the same buffer and stored at −70° C. Samples are thawed at room temperature and washed in homogenization buffer (100 mM $K_2HPO_4/KH_2PO_4$ (pH 7.5) supplemented with 2 mM $MgCl_2$, 1 mM DTT and Protease Inhibitor (EDTA-free, Roche). Washed samples are resuspended in 0.5 mL of homogenization buffer and twice homogenized for 30 seconds with 0.5 mL glass beads using a Bead Beater homogenizer. Samples are then centrifuged at 14,000 rpm for 30 minutes at 4° C. LDH activity is determined by analyzing the supernatant spectrophotometrically (A340) using a Cobas MIRA automated analyzer at 30° C. in sodium acetate buffer containing 0.4 mM NADH, 5 mM fructose-1,6-diphosphate and 2 mM pyruvate. 1 U of activity is defined as the amount of activity converting 1 mol of NADH to $NAD^\pm$/minute. Protein concentrations are determined using the Bio-Rad method, with bovine gamma-globulin used as a protein standard.

Strains CD1184, CD1439 and CD1440 all consume glucose at approximately the same rate, and all produce approximately 55-60 g/L of lactate. Each produces approximately 0.6 g/L pyruvate and 6 g/L glycerol. The LDH activity of strain CD1439 is approximately 40% higher than that of CD1440 throughout the cultivation, due to the presence of the second copy of the LhLDH cassette.

EXAMPLE 12A

Cloning of *I. orientalis* Native GPD1 Gene Together with Upstream and Downstream Flanking Region Known glycerol-3-phosphate dehydrogenase genes from several yeast species (*S. cerevisiae, K. marxianus, Y. lipoly-*

*tica, P. jadinii, D. hansenii* and *C. glabrata*) are aligned and regions which are highly conserved among the various genes are identified. Two sets of degenerate primers were designed in these regions of high homology. These sets are identified as SEQ. ID. NO. 60 and SEQ. ID. NO. 61, and SEQ. ID. NO. 62 and SEQ. ID. NO. 63, respectively. PCR is performed using the first set of primers and *I. orientalis* genomic DNA as the template, and a ~200 bp product is obtained as expected. PCR is again performed using the second set of primers and *I. orientalis* genomic DNA as the template, and a ~400 bp product is obtained as expected. The two PCR products are gel purified and sequenced using the same primers. Using the partial sequence so obtained, primers are designed for genome walking. Genome walking is performed using the BD Clontech Genome Walking Kit according to the manufacturer's instructions using primary PCR primers identified as SEQ. ID. NO. 64 and SEQ. ID. NO. 65 and nested PCR primers identified as SEQ. ID. NO. 66 and SEQ. ID. NO. 67. Sequences obtained from both upstream and downstream genome walks are aligned and merged with the previously obtained partial sequence to construct the *I. orientalis* glycerol-3-phosphate dehydrogenase gene.

EXAMPLE 12B

Construction of Plasmids pMI449 (FIG. 18) and pMI454 (FIG. 19) Containing *I. orientalis* CYB2 5' Flanking Region, ScMEL5 Gene Cassette Between *K. thermotolerans* Direct Repeat Sequences and *I. Orientalis* CYB2 3' Flanking Region Plasmid pMM28 (FIG. 10, Ex. 10A) is digested with BamHI, filled in with the Klenow enzyme, and digested with SalI. The 4077 bp fragment so obtained is ligated to a 2317 bp NotI (filled in with Klenow enzyme)-SalI fragment of pMI433 (FIG. 8, Ex. 3A). The resulting plasmid is designated pMI445.

The 3' flanking region of the *I. orientalis* L-lactate:ferricytochrome c oxidoreductase (IoCYB2A) gene (corresponding to sequences from 90 to 676 bp downstream of the predicted open reading frame) is amplified by PCR using primers identified as SEQ. ID. NO. 68 and SEQ. ID. NO. 69, using a CYB2-2 cosmid clone as a template. The PCR product is digested with SacI and SmaI and the 607 bp fragment is ligated to the 6386 bp SacI—SmaI fragment of plasmid pMI445. The resulting plasmid is designated pMI448.

The IoCYB2A 5' flanking region (corresponding to sequences from 913 to 487 bp upstream of the predicted open reading frame) is amplified by PCR using primers identified as SEQ. ID. NO. 70 and SEQ. ID. NO. 71, again using the CYB2-2 cosmid clone as a template. The PCR product is digested with SphI and the 454 bp fragment is ligated to the 6993 bp SphI fragment obtained by partially digesting pMI448. The resulting plasmid is designated pMI449 (FIG. 18).

The IoCYB2A 5' flanking region (corresponding to sequences from 466 to 7 bp upstream of the predicted open reading frame) is amplified by PCR using primers identified as SEQ. ID. NO. 72 and SEQ. ID. NO. 73, once again using the CYB2-2 cosmid clone as the template. The PCR product is digested with SphI and the 493 bp fragment is ligated to the 6993 bp SphI fragment obtained by partially digesting plasmid pMI448. The resulting plasmid is designated pMI453.

The IoCYB2A 3' flanking region (corresponding to sequences from 402 bp upstream to 77 bp downstream of the predicted stop codon) is amplified by PCR using primers identified as SEQ. ID. NO. 74 and SEQ. ID. NO. 75, using the CYB2-2 cosmid as a template. The PCR product is digested with ApaI and SmaI and the 506 bp fragment is ligated to the 6886 bp ApaI—SmaI fragment of plasmid pMI453. The resulting plasmid is designated pMI454 (FIG. 19).

EXAMPLE 12C

Construction of a Plasmid (pBH165, FIG. 20) Containing an Upstream Fragment of the IoGPD1 Gene, a First *K. thermotolerans* Direct Repeat Section, a MEL5 Gene Cassette, a Second *K. thermotolerans* Direct Repeat Section, and a Downstream Fragment of the IoGPD1 Gene Plasmid pMI449 (FIG. 18, Ex. 12B) is digested with NdeI and SbfI to excise the 5' CYB2A flanking homology. A 6.8 kbp fragment is gel purified and dephosphorylated. A 302 bp fragment of the IoGPDJ gene from Example 12A (corresponding to base pairs 1-302 from the start codon of the gene) is amplified by PCR using primers identified as SEQ. ID. NO. 76 and SEQ. ID. NO. 77. The PCR product is gel purified, digested with NdeI and SbfI, and ligated to the 6.8 kbp fragment from plasmid pMI449 to produce plasmid pBH164. Plasmid pBH164 is then digested with XmaI and EcoRI to excise the 3' CYB2A flanking homology. A 6.5 kbp fragment is gel purified and dephosphorylated. A 346 bp fragment of the IoGPDJ gene from Example 12A (corresponding to base pairs 322-668 from the start codon) is amplified by PCR using primers identified as SEQ. ID. NO. 78 and SEQ. ID. NO. 79. The PCR product is gel purified, digested with XmaI and EcoRI, and ligated to the 6.5 kbp fragment obtained from pBH164 to produce pBH165 (FIG. 20).

Plasmid pBH165 contains, in order of transcription, the 302 bp fragment of the IoGPD1 gene, a first *K. thermotolerans* direct repeat section, a MEL5 gene cassette, a second *K. thermotolerans* direct repeat section, and the 346 bp fragment of the IoGPD1 gene. It is designed for insertion at the locus of the native IoGPD1 gene (with disruption of the gene), followed by a loop-out of the MEL5 gene cassette.

EXAMPLE 12D

Generation of *I. orientalis* Mutant Strain (CD1496) by Successively Transforming Strain CD1184 (Ex. 4) with Plasmids pMI449 (Ex. 12B, FIG. 18) and pMI454 (Ex. 12B, FIG. 19), Followed by Mutagenesis Strain CD1184 is transformed with plasmid pMI449 using the lithium acetate method and transformants (blue colonies) are selected based on melibiase activity on YPD X-gal plates. The replacement of the IoCYB2A gene of strain CD1184 is confirmed by colony PCR and Southern analysis in some of the transformants. The MEL5 marker is looped out from one of those transformants via a homologous recombination event through the *K. thermotolerans* repeat sequences, as confirmed by Southern analysis. The second CYB2A allele is then deleted from this transformant using plasmid pMI454. Transformants are analyzed by colony PCR for the absence of a 1000 bp CYB2A-specific PCR product. The MEL5 marker from plasmid pMI454 is looped out of a transformant having a deletion of the second CYB2A allele via recombination as before. This transformant is designated strain CD1436. Strain CD1436 has a deletion of both PDC1 alleles (with replacement by a functional L-LDH gene cassette), and a deletion of each of its two native IoCYB2 genes.

Cells of strain CD1436 from a fresh YPD plate are resuspended in 2 mL phosphate-buffered saline to an approximate $OD_{600}$ of 6. Twelve 2000 aliquots of this cell suspension are pipeted into twelve 14 mL snap-cap tubes, and 8 µL of ethyl methanesulfonate (EMS, Sigma Chemical Co., St. Louis, Mo., catalog #M0880, 1.17 g/mL solution) is added to ten of the twelve tubes. The remaining two tubes serve as mock-treated controls. The tubes are then incubated at 30° C. with agitation (225 rpm) for 60 minutes, to kill 90-99% of the cells. Following exposure to EMS, the cells from the twelve tubes are pelleted, washed twice with 5.0% $Na_2S_2O_3$ to neutralize the EMS and washed once with water. Mutagenized cells are allowed to recover for 6 hours in 2004 of YP+20 g/L glucose media and then plated onto PDA+35 g/L lactic acid plates and incubated for one week at 30° C. A strain that produces more lactate and less glycerol than strain CD1436 is designated as strain CD1496.

EXAMPLE 12E

Transformation of Strain CD 1496 (Ex. 12D) with Plasmid pBH165 (Ex. 12C, FIG. 20), Followed by Loop-Out of the Selection Marker to Produce Transformant Strain CD1671 which has a Single GPD1 Allele Deleted Strain CD1496 is grown and transformed with 5 g of the 4.4 kbp fragment obtained by digesting plasmid pBH165 with NdeI and EcoRI. Transformants are selected on yeast nitrogen base (YNB)+2% melibiose plates overlaid with x-α-gal (5-bromo-4-chloro-3-indolyl-aD-galactoside). Blue-colored transformants are visible after ~4 days of growth at 30° C. Eight transformants are picked and plated for single colonies on YP+20 g/L glucose plates containing x-α-gal. A single blue colony for each transformant is picked and restreaked to YP+20 g/L glucose plates. Genomic DNA is isolated from the transformants. Disruption of one allele of the IoGPDJ gene is verified by PCR using primers identified as SEQ. ID. NO. 80 and SEQ. ID. NO. 81. One transformant that exhibits the expected ~2 kb product is designated as strain CD1657. Disruption of one copy of the native IoGPDJ gene is further verified by PCR using primers designated as SEQ. ID. NO. 82 and SEQ. ID. NO. 83.

Strain CD1657 is grown for several rounds in YP+100 g/L glucose at 30° C. A dilution series is plated onto YP+20 g/L plates overlaid with x-1-gal, and grown overnight at 30° C. A white colony (indicative of the loop-out of the MEL 5 marker cassette) is selected and restreaked to YP+20 g/L glucose+x-1-gal plates. A white colony is selected. Disruption of one allele of the native IoGPDJ gene is verified by PCR using primers identified as SEQ. ID. NO. 84 and SEQ. ID. NO. 85. This transformant is designated as strain CD1671.

EXAMPLE 12F

Transformation of Strains CD1671 (Ex. 12E) with Plasmid pBH165 (Ex. 12C, FIG. 20) to Produce Transformant Strain CD1690 with Both IoGPD1 Alleles Deleted Strain CD1671 is transformed with 5 g of a 4.4 kbp fragment obtained by digesting plasmid pBH165 with NdeI and EcoRI. Transformants are selected on YNB+2% melibiose plates overlaid with x-α-gal. Blue-colored transformants are visible after ~4 days of growth at 30° C. Ten transformants are picked and plated for single colonies on YP+20 g/L glucose plates containing x-α-gal. A single blue colony for each transformant is picked and restreaked to YP+20 g/L glucose. Genomic DNA is isolated from the transformants. Disruption of the second allele of the IoGPDJ gene is verified in a transformant by PCR using primers identified as SEQ. ID. NO 86 and SEQ. ID. NO. 86. This transformant is designated as strain CD1690.

EXAMPLE 12G

Microaerobic Shake Flask Characterizations of Strain CD1690 (Ex. 12F)

Strain CD1690 is inoculated to an initial OD600 of 0.2 into YP+100 g/L glucose in 3-liter batch fermenter. The flasks are incubated for 40 hours at 38-40° C. with 100 rpm shaking. The cultivation is buffered to pH 5.5 throughout the cultivation. Under these conditions, strain CD1690 produces a yield of 88 grams of L-lactic acid/100 grams of glucose that is consumed. L-lactic acid productivity is 2.6 g/L/hr. Yields for by-products are $CO_2$: 8%; biomass: 2.4%, and pyruvate: 1%. The final OD600 is 6.3.

EXAMPLE 13A

Cloning of P. membranifaciens Native PDC1 Gene Fragment

A pair of degenerate primers is designed to clone a portion of the PDC1 gene in P. membranifaciens. These primers are identified as SEQ. ID. NO. 88 and SEQ. ID. NO. 89. PCR is performed using the primers and P. membranifaciens genomic DNA as the template, and a ~700 bp product is obtained. The fragment is cloned onto a commercial TOPO vector to produce a plasmid designated as plasmid PDC-7 clone. The fragment is sequenced using primers identified as SEQ. ID. NO. 90 and SEQ. ID. NO. 91. The nucleotide sequence of the fragment is identified as SEQ. ID. NO. 92. The fragment has high identify with other known yeast PDC gene sequences.

EXAMPLE 13B

Construction of Plasmid pMI464 (FIG. 21) Containing P. membranifaciens PDC1 Gene Fragment, Hygromycin Expression Cassette and LhLDH Expression Cassette Plasmid pMI357 (FIG. 6, Ex. 2B) is digested with SacI and SalI to form a ~7735 bp fragment. Plasmid PDC-y clone is digested with SacI and XhoI to produce a ~700 bp fragment. The two fragments are ligated together to form a plasmid designated as plasmid pMI464.

EXAMPLE 13C

Generation of Strain CD1598 by Transformation of a Wild-Type P. membranifaciens Strain with Plasmid pMI464 to Integrate the LhLDH Gene Cassette A wild-type P. membranifaciens strain designated as NCYC2696 is transformed with a fragment obtained by digesting plasmid pMI464 with AgeI. Transformants are selected on YDP+hygromycin plates and streaked onto YDP+200 µg/mL hygromycin. One colony is designated as strain CD1598. The presence of the LhLDH gene cassette in the strain is verified by PCR.

EXAMPLE 13D

Microaerobic Shake Flask Characterization of Strain CD1598 (Ex. 13C)

Strain CD1598 is inoculated to an initial OD600 of 0.2 into 50 ml of non-buffered YP+10% glucose medium in a shake flask. The flask is incubated for 7 days at 30° C. with 100 rpm shaking. Strain CD1598 produces lactic acid to a titer of 47 g/L. Lactic acid yield is 70% based on glucose consumed. Lactic acid production rate is 0.41 g/L/hr. The strain does not produce ethanol.

---

We claim:

1. A yeast cell of a species of the *Issatchenkia orientalis/P. fermentans* clade having at least one genetic modification selected from (1) an insertion of a functional exogenous xylose isomerase gene, (2) a deletion or a disruption of a native xylose reductase gene, (3) a deletion or a disruption of a native xylitol dehydrogenase gene and/or (4) an insertion of an exogenous xylulokinase gene.

2. The yeast cell of claim 1 which is of the species *Issatchenkia orientalis, Pichia galeiformis, Candida ethanolica, P. deserticola, P. membranifaciens* or *P. fermentans*.

* * * * *